(12) United States Patent
Basi et al.

(10) Patent No.: US 7,256,273 B2
(45) Date of Patent: Aug. 14, 2007

(54) HUMANIZED ANTIBODIES THAT RECOGNIZE BETA AMYLOID PEPTIDE

(75) Inventors: Guriq Basi, Palo Alto, CA (US); Jose Saldanha, Enfield (GB)

(73) Assignees: Elan Pharma International Limited (IE); Wyeth, Madison, NJ (US)

( * ) Notice: Subject to any disclaimer, the term of this patent is extended or adjusted under 35 U.S.C. 154(b) by 63 days.

(21) Appl. No.: 10/388,214

(22) Filed: Mar. 12, 2003

(65) Prior Publication Data

US 2004/0082762 A1    Apr. 29, 2004

Related U.S. Application Data

(60) Provisional application No. 60/363,751, filed on Mar. 12, 2002.

(51) Int. Cl.
| | |
|---|---|
| C12P 21/08 | (2006.01) |
| C07K 16/00 | (2006.01) |
| A61K 39/395 | (2006.01) |
| C12P 21/04 | (2006.01) |
| C12P 21/06 | (2006.01) |
| G01N 33/53 | (2006.01) |
| C12N 15/00 | (2006.01) |
| C07H 21/04 | (2006.01) |

(52) U.S. Cl. ............... 530/387.3; 530/387.9; 530/388.1; 530/388.24; 424/133.1; 424/139.1; 424/141.1; 424/145.1; 435/69.1; 435/69.6; 435/70.21

(58) Field of Classification Search ............. 530/387.3, 530/388.1, 388.24, 387.9; 424/133.1, 139.1, 424/141.1; 435/69.1, 69.6, 70.21, 449
See application file for complete search history.

(56) References Cited

U.S. PATENT DOCUMENTS

| | | | |
|---|---|---|---|
| 4,666,829 A | 5/1987 | Glenner et al. |
| 4,713,366 A | 12/1987 | Stevens |
| 4,816,397 A | 3/1989 | Boss et al. |
| 4,816,567 A | 3/1989 | Cabilly et al. |
| 4,883,666 A | 11/1989 | Sabel et al. |
| 4,912,206 A | 3/1990 | Goldgaber et al. |
| 5,004,697 A | 4/1991 | Pardridge |
| 5,057,540 A | 10/1991 | Kensil et al. |
| 5,096,706 A | 3/1992 | Flint |
| 5,187,153 A | 2/1993 | Cordell et al. |
| 5,192,753 A | 3/1993 | McGeer et al. |
| 5,208,036 A | 5/1993 | Eppstein et al. |
| 5,220,013 A | 6/1993 | Ponte et al. |
| 5,225,539 A | 7/1993 | Winter |
| 5,227,159 A | 7/1993 | Miller |
| 5,231,000 A | 7/1993 | Majocha et al. |
| 5,231,170 A | 7/1993 | Averback |
| 5,258,498 A | 11/1993 | Huston et al. |
| 5,270,165 A | 12/1993 | Van Nostrand et al. |
| 5,278,049 A | 1/1994 | Baker et al. |
| 5,385,887 A | 1/1995 | Yim et al. |
| 5,387,742 A | 2/1995 | Cordell |
| 5,434,170 A | 7/1995 | Andrulis, Jr. |
| 5,441,870 A | 8/1995 | Seubert et al. |
| 5,464,823 A | 11/1995 | Lehrer et al. |
| 5,470,951 A | 11/1995 | Roberts |
| 5,514,548 A | 5/1996 | Krebber et al. |
| 5,571,499 A | 11/1996 | Hafler et al. |
| 5,571,500 A | 11/1996 | Hafler et al. |
| 5,576,184 A | 11/1996 | Better et al. |
| 5,583,112 A | 12/1996 | Kensil et al. |
| 5,585,089 A | 12/1996 | Queen et al. |
| 5,585,100 A | 12/1996 | Mond et al. |
| 5,589,154 A | 12/1996 | Anderson |
| 5,593,846 A | 1/1997 | Schenk et al. |
| 5,601,827 A | 2/1997 | Collier et al. |
| 5,605,811 A | 2/1997 | Seubert et al. |
| 5,612,486 A | 3/1997 | McConlogue et al. |
| 5,618,920 A | 4/1997 | Robinson et al. |
| 5,622,701 A | 4/1997 | Berg |
| 5,624,821 A | 4/1997 | Winter et al. |
| 5,641,473 A | 6/1997 | Hafler et al. |
| 5,641,474 A | 6/1997 | Hafler et al. |
| 5,645,820 A | 7/1997 | Hafler et al. |
| 5,648,260 A | 7/1997 | Winter et al. |
| 5,652,334 A | 7/1997 | Roberts |
| 5,677,425 A | 10/1997 | Bodmer et al. |
| 5,679,348 A | 10/1997 | Nesburn et al. |
| 5,688,651 A | 11/1997 | Solomon |
| 5,693,761 A | 12/1997 | Queen et al. |
| 5,693,762 A | 12/1997 | Queen et al. |
| 5,702,906 A | 12/1997 | Rosenthal |
| 5,721,130 A | 2/1998 | Seubert et al. |
| 5,733,547 A | 3/1998 | Weiner et al. |
| 5,733,548 A | 3/1998 | Restifo et al. |

(Continued)

FOREIGN PATENT DOCUMENTS

AU    707083    7/1999

(Continued)

OTHER PUBLICATIONS

Elgert K. D. Immunology, Understanding the Immune System, p. 59, 1996.*

(Continued)

Primary Examiner—David J. Blanchard
(74) Attorney, Agent, or Firm—Lahive & Cockfield, LLP; Amy E. Mandragouras, Esq.; Debra J. Milasincic, Esq.

(57) ABSTRACT

The invention provides improved agents and methods for treatment of diseases associated with amyloid deposits of Aβ in the brain of a patient. Preferred agents include humanized antibodies.

55 Claims, 18 Drawing Sheets

U.S. PATENT DOCUMENTS

| | | |
|---|---|---|
| 5,736,142 A | 4/1998 | Sette et al. |
| 5,744,132 A | 4/1998 | Warne et al. |
| 5,744,368 A | 4/1998 | Goldgaber et al. |
| 5,750,349 A | 5/1998 | Suzuki et al. |
| 5,750,361 A | 5/1998 | Prusiner et al. |
| 5,753,624 A | 5/1998 | McMichael et al. |
| 5,766,846 A | 6/1998 | Schlossmacher et al. |
| 5,770,700 A | 6/1998 | Webb et al. |
| 5,776,468 A | 7/1998 | Hauser et al. |
| 5,780,587 A | 7/1998 | Potter |
| 5,786,180 A | 7/1998 | Konig et al. |
| 5,817,626 A | 10/1998 | Findeis et al. |
| 5,824,322 A | 10/1998 | Balasubramanian |
| 5,837,268 A | 11/1998 | Potter et al. |
| 5,837,473 A | 11/1998 | Maggio et al. |
| 5,837,672 A | 11/1998 | Schenk et al. |
| 5,846,533 A | 12/1998 | Prusiner |
| 5,849,298 A | 12/1998 | Weiner et al. |
| 5,851,996 A | 12/1998 | Kline |
| 5,854,204 A | 12/1998 | Findeis et al. |
| 5,854,215 A | 12/1998 | Findeis et al. |
| 5,859,205 A | 1/1999 | Adair et al. |
| 5,869,046 A | 2/1999 | Presta et al. |
| 5,869,054 A | 2/1999 | Weiner et al. |
| 5,869,093 A | 2/1999 | Weiner et al. |
| 5,877,399 A | 3/1999 | Hsiao et al. |
| 5,891,991 A | 4/1999 | Wasco et al. |
| 5,935,927 A | 8/1999 | Vitek et al. |
| 5,955,079 A | 9/1999 | Mond et al. |
| 5,955,317 A | 9/1999 | Suzuki et al. |
| 5,958,883 A | 9/1999 | Snow |
| 5,985,242 A | 11/1999 | Findeis et al. |
| 5,989,566 A | 11/1999 | Cobb et al. |
| 6,022,859 A | 2/2000 | Kiessling et al. |
| 6,054,297 A | 4/2000 | Carter et al. |
| 6,057,367 A | 5/2000 | Stamler et al. |
| 6,114,133 A | 9/2000 | Seubert et al. |
| 6,121,022 A | 9/2000 | Presta et al. |
| 6,150,091 A | 11/2000 | Pandolfo et al. |
| 6,165,745 A | 12/2000 | Ward et al. |
| 6,175,057 B1 | 1/2001 | Mucke et al. |
| 6,180,370 B1 | 1/2001 | Queen et al. |
| 6,194,551 B1 | 2/2001 | Idusogie et al. |
| 6,210,671 B1 | 4/2001 | Co |
| 6,218,506 B1 | 4/2001 | Krafft et al. |
| 6,261,569 B1 | 7/2001 | Comis et al. |
| 6,262,335 B1 | 7/2001 | Hsiao et al. |
| 6,267,958 B1 | 7/2001 | Andya et al. |
| 6,270,757 B1 | 8/2001 | Warne |
| 6,277,375 B1 | 8/2001 | Ward |
| 6,284,221 B1 | 9/2001 | Schenk et al. |
| 6,284,533 B1 | 9/2001 | Thomas |
| 6,294,171 B2 | 9/2001 | McMichael |
| 6,303,567 B1 | 10/2001 | Findeis et al. |
| 6,331,440 B1 | 12/2001 | Nordstedt et al. |
| 6,372,716 B1 | 4/2002 | Bush et al. |
| 6,399,314 B1 | 6/2002 | Krishnamurthy |
| 6,407,213 B1 | 6/2002 | Carter et al. |
| 6,417,178 B1 | 7/2002 | Klunk et al. |
| 6,528,624 B1 | 3/2003 | Idusogie et al. |
| 6,538,124 B1 | 3/2003 | Idusogie et al. |
| 6,548,640 B1 | 4/2003 | Winter |
| 6,562,341 B2 | 5/2003 | Prusiner et al. |
| 6,610,493 B1 | 8/2003 | Citron et al. |
| 6,632,927 B2 | 10/2003 | Adair et al. |
| 6,639,055 B1 | 10/2003 | Carter et al. |
| 6,710,226 B1 | 3/2004 | Schenk |
| 6,713,450 B2 | 3/2004 | Frangione et al. |
| 6,743,427 B1 | 6/2004 | Schenk |
| 6,750,324 B1 | 6/2004 | Schenk et al. |
| 6,761,888 B1 | 7/2004 | Schenk |
| 6,787,138 B1 | 9/2004 | Schenk |
| 6,787,139 B1 | 9/2004 | Schenk |
| 6,787,140 B1 | 9/2004 | Schenk |
| 6,787,143 B1 | 9/2004 | Schenk |
| 6,787,144 B1 | 9/2004 | Schenk |
| 6,787,523 B1 | 9/2004 | Schenk |
| 6,787,637 B1 | 9/2004 | Schenk et al. |
| 6,808,712 B2 | 10/2004 | Schenk |
| 6,818,218 B2 | 11/2004 | Schenk |
| 6,866,849 B2 | 3/2005 | Schenk |
| 6,866,850 B2 | 3/2005 | Schenk |
| 6,875,434 B1 | 4/2005 | Schenk |
| 6,890,535 B1 | 5/2005 | Schenk |
| 6,905,686 B1 | 6/2005 | Schenk |
| 6,913,745 B1 | 7/2005 | Schenk |
| 6,933,368 B2 | 8/2005 | Co et al. |
| 6,936,698 B2 | 8/2005 | Taylor |
| 6,946,135 B2 | 9/2005 | Schenk |
| 6,962,707 B2 | 11/2005 | Schenk |
| 6,972,127 B2 | 12/2005 | Schenk |
| 2001/0018053 A1 | 8/2001 | McMichael |
| 2001/0021769 A1 | 9/2001 | Prusiner |
| 2002/0009445 A1 | 1/2002 | Du et al. |
| 2002/0058267 A1 | 5/2002 | Ozenberger et al. |
| 2002/0077288 A1 | 6/2002 | Frangione |
| 2002/0086847 A1 | 7/2002 | Chain |
| 2002/0094335 A1 | 7/2002 | Chalifour et al. |
| 2002/0102261 A1 | 8/2002 | Raso |
| 2002/0132268 A1 | 9/2002 | Chang et al. |
| 2002/0133001 A1 | 9/2002 | Gefter et al. |
| 2002/0136718 A1 | 9/2002 | Raso |
| 2002/0160394 A1 | 10/2002 | Wu |
| 2002/0162129 A1 | 10/2002 | Lannfelt |
| 2002/0168377 A1 | 11/2002 | Schaetzl |
| 2002/0187157 A1 | 12/2002 | Jensen et al. |
| 2002/0197258 A1 | 12/2002 | Ghanbari et al. |
| 2003/0039645 A1 | 2/2003 | Adair et al. |
| 2003/0068316 A1 | 4/2003 | Klein et al. |
| 2003/0068325 A1 | 4/2003 | Wang |
| 2003/0073655 A1 | 4/2003 | Chain |
| 2003/0147882 A1 | 8/2003 | Solomon et al. |
| 2003/0165496 A1 | 9/2003 | Basi et al. |
| 2003/0166557 A1 | 9/2003 | Minna et al. |
| 2003/0166558 A1 | 9/2003 | Frangione et al. |
| 2003/0202972 A1 | 10/2003 | James et al. |
| 2004/0043418 A1 | 3/2004 | Holtzman et al. |
| 2004/0082762 A1 | 4/2004 | Basi et al. |
| 2004/0087777 A1 | 5/2004 | Basi et al. |
| 2004/0171815 A1 | 9/2004 | Schenk et al. |
| 2004/0197324 A1 | 10/2004 | Jun et al. |
| 2004/0241164 A1 | 12/2004 | Bales et al. |
| 2004/0247612 A1 | 12/2004 | Wang |
| 2004/0265919 A1 | 12/2004 | Vanderstichele et al. |
| 2005/0009150 A1 | 1/2005 | Basi et al. |
| 2005/0059591 A1 | 3/2005 | Schenk et al. |
| 2005/0059802 A1 | 3/2005 | Schenk et al. |
| 2005/0118651 A1 | 6/2005 | Basi et al. |
| 2005/0123534 A1 | 6/2005 | Adair et al. |
| 2005/0136054 A1 | 6/2005 | Adair et al. |
| 2005/0163788 A1 | 7/2005 | Schenk |
| 2005/0169925 A1 | 8/2005 | Bardroff et al. |
| 2005/0191314 A1 | 9/2005 | Schenk |
| 2005/0249725 A1 | 11/2005 | Schenk et al. |
| 2005/0249727 A1 | 11/2005 | Schenk |
| 2005/0255122 A1 | 11/2005 | Schenk |

FOREIGN PATENT DOCUMENTS

| | | | |
|---|---|---|---|
| EP | 285 159 | A1 | 10/1988 |
| EP | 451 700 | A1 | 10/1991 |
| EP | 276 723 | B1 | 12/1993 |
| EP | 597 101 | A1 | 5/1994 |
| EP | 613 007 | A2 | 8/1994 |

| | | | | | | |
|---|---|---|---|---|---|---|
| EP | 620 276 | A1 | 10/1994 | WO | WO 97/03192 A3 | 1/1997 |
| EP | 626 390 | A1 | 11/1994 | WO | WO 97/08320 A1 | 3/1997 |
| EP | 666 080 | A1 | 8/1995 | WO | WO 97/10505 A1 | 3/1997 |
| EP | 359 783 | B1 | 11/1995 | WO | WO 97/17613 A1 | 5/1997 |
| EP | 683 234 | A1 | 11/1995 | WO | WO 97/21728 A1 | 6/1997 |
| EP | 440 619 | B1 | 1/1996 | WO | WO 97/32017 A1 | 9/1997 |
| EP | 758 248 | B1 | 2/1997 | WO | WO 98/02462 A1 | 1/1998 |
| EP | 758 901 | B1 | 2/1997 | WO | WO 98/05350 A1 | 2/1998 |
| EP | 526 511 | B1 | 5/1997 | WO | WO 98/07850 A1 | 2/1998 |
| EP | 782 859 | A1 | 7/1997 | WO | WO 98/08868 A1 | 3/1998 |
| EP | 783 104 | A1 | 7/1997 | WO | WO 98/22120 A1 | 5/1998 |
| EP | 594 607 | B1 | 8/1997 | WO | WO 98/33815 A1 | 8/1998 |
| EP | 752 886 | B1 | 1/1998 | WO | WO 98/44955 A1 | 10/1998 |
| EP | 845 270 | A1 | 6/1998 | WO | WO 99/00150 A2 | 1/1999 |
| EP | 863 211 | A1 | 9/1998 | WO | WO 99/06066 A2 | 2/1999 |
| EP | 868 918 | A2 | 10/1998 | WO | WO 99/06587 A2 | 2/1999 |
| EP | 652 962 | B1 | 12/1998 | WO | WO 99/10008 A1 | 3/1999 |
| EP | 911 036 | A2 | 4/1999 | WO | WO 99/27911 A1 | 6/1999 |
| EP | 561 087 | B1 | 8/1999 | WO | WO 99/27944 A1 | 6/1999 |
| EP | 639 081 | B1 | 11/1999 | WO | WO 99/27949 A1 | 6/1999 |
| EP | 506 785 | B1 | 3/2000 | WO | WO 99/06545 A2 | 11/1999 |
| EP | 1 172 378 | A1 | 1/2002 | WO | WO 99/58564 A1 | 11/1999 |
| GB | 2 220 211 | A | 1/1990 | WO | WO 99/60021 A1 | 11/1999 |
| GB | 2 335 192 | A | 9/1999 | WO | WO 99/60024 A1 | 11/1999 |
| JP | 62-267297 | A | 11/1987 | WO | WO 00/20027 A2 | 4/2000 |
| JP | 7-132033 | A | 5/1995 | WO | WO 00/23082 A1 | 4/2000 |
| JP | 7-165799 | A | 6/1995 | WO | WO 00/26238 A2 | 5/2000 |
| WO | WO 88/10120 | A1 | 12/1988 | WO | WO 00/43039 A1 | 7/2000 |
| WO | WO 89/01343 | A1 | 2/1989 | WO | WO 00/43049 A1 | 7/2000 |
| WO | WO 89/03687 | A1 | 5/1989 | WO | WO 00/68263 A2 | 11/2000 |
| WO | WO 89/06242 | A1 | 7/1989 | WO | WO 00/72870 A1 | 12/2000 |
| WO | WO 89/06689 | A1 | 7/1989 | WO | WO 00/72876 A2 | 12/2000 |
| WO | WO 90/12870 | A1 | 11/1990 | WO | WO 00/72876 A3 | 12/2000 |
| WO | WO 90/12871 | A1 | 11/1990 | WO | WO 00/72880 A2 | 12/2000 |
| WO | WO 91/08760 | A1 | 6/1991 | WO | WO 00/72880 A3 | 12/2000 |
| WO | WO 91/09967 | A1 | 7/1991 | WO | WO 00/77178 A1 | 12/2000 |
| WO | WO 91/12816 | A1 | 9/1991 | WO | WO 01/05355 A2 | 1/2001 |
| WO | WO 91/16819 | A1 | 11/1991 | WO | WO 01/10900 A2 | 2/2001 |
| WO | WO 91/16928 | A1 | 11/1991 | WO | WO 01/18169 A3 | 3/2001 |
| WO | WO 91/19810 | A1 | 12/1991 | WO | WO 01/39796 A2 | 6/2001 |
| WO | WO 92/06187 | A1 | 4/1992 | WO | WO 01/42306 A2 | 6/2001 |
| WO | WO 92/06708 | A1 | 4/1992 | WO | WO 01/62284 A2 | 8/2001 |
| WO | WO 92/13069 | A1 | 8/1992 | WO | WO 01/62801 A2 | 8/2001 |
| WO | WO 93/02189 | A1 | 2/1993 | WO | WO 01/77167 A2 | 10/2001 |
| WO | WO 93/04194 | A1 | 3/1993 | WO | WO 01/90182 A2 | 11/2001 |
| WO | WO 93/14200 | A1 | 7/1993 | WO | WO 02/03911 A2 | 1/2002 |
| WO | WO 93/15760 | A1 | 8/1993 | WO | WO 02/21141 A2 | 3/2002 |
| WO | WO 93/16724 | A1 | 9/1993 | WO | WO 02/34777 A1 | 5/2002 |
| WO | WO 93/21950 | A1 | 11/1993 | WO | WO 02/34878 A2 | 5/2002 |
| WO | WO 94/00153 | A1 | 1/1994 | WO | WO 02/046237 A1 | 6/2002 |
| WO | WO 94/01772 | A1 | 1/1994 | WO | WO 02/060481 A2 | 8/2002 |
| WO | WO 94/03615 | A1 | 2/1994 | WO | WO 02/088306 A2 | 11/2002 |
| WO | WO 94/05311 | A1 | 3/1994 | WO | WO 02/088307 A2 | 11/2002 |
| WO | WO 94/10569 | A1 | 5/1994 | WO | WO 02/096937 A2 | 12/2002 |
| WO | WO 94/28412 | A1 | 12/1994 | WO | WO 03/009817 A2 | 2/2003 |
| WO | WO 95/04151 | A2 | 2/1995 | WO | WO 03/015691 A2 | 2/2003 |
| WO | WO 95/05393 | A2 | 2/1995 | WO | WO 03/016466 A2 | 2/2003 |
| WO | WO 95/05853 | A1 | 3/1995 | WO | WO 03/016467 A2 | 2/2003 |
| WO | WO 95/06407 | A1 | 3/1995 | WO | WO 03/016467 A3 | 2/2003 |
| WO | WO 95/08999 | A1 | 4/1995 | WO | WO 03/020212 A2 | 3/2003 |
| WO | WO 95/11008 | A2 | 4/1995 | WO | WO 03/039485 A2 | 5/2003 |
| WO | WO 95/11311 | A1 | 4/1995 | WO | WO 03/051374 A2 | 6/2003 |
| WO | WO 95/11994 | A1 | 5/1995 | WO | WO 03/074081 A1 | 9/2003 |
| WO | WO 95/12815 | A1 | 5/1995 | WO | WO 03/077858 A2 | 9/2003 |
| WO | WO 95/17085 | A1 | 6/1995 | WO | WO 03/077858 A3 | 9/2003 |
| WO | WO 95/23166 | A1 | 8/1995 | WO | WO 03/104437 A2 | 12/2003 |
| WO | WO 95/31996 | A1 | 11/1995 | WO | WO 03/105894 A1 | 12/2003 |
| WO | WO 96/08565 | A2 | 3/1996 | WO | WO 2004/013172 A2 | 2/2004 |
| WO | WO 96/18900 | A1 | 6/1996 | WO | WO 2004/013172 A3 | 2/2004 |
| WO | WO 96/25435 | A1 | 8/1996 | WO | WO 2004/031400 A2 | 4/2004 |
| WO | WO 96/28471 | A1 | 9/1996 | WO | WO 2004/055164 A2 | 7/2004 |
| WO | WO 96/37621 | A2 | 11/1996 | WO | WO 2004/080419 A2 | 9/2004 |
| WO | WO 96/39176 | A1 | 12/1996 | WO | WO 2004/108895 A2 | 12/2004 |

| WO | WO 2004/108895 A3 | 12/2004 |
| WO | WO 2005/014041 A2 | 2/2005 |

OTHER PUBLICATIONS

Paul W. E. Fundamental Immunology, 3rd Edition, pp. 292-295, 1993.*
Rudikoff et al. Proc. Natl. Acad. Sci. USA 79:1979-1983, 1982.*
Coleman P. M. Research in Immunology, 145:33-36, 1994.*
U.S. Appl. No. 60/254,465, filed Dec. 8, 2000, Holtzman et al.
U.S. Appl. No. 60/254,498, filed Dec. 8, 2000, Holtzman et al.
U.S. Appl. No. 09/724,842, filed Nov. 28, 2000, Chalifour et al.
U.S. Appl. No. 60/186,295, filed Mar. 1, 2000, Rasmussen et al.
U.S. Appl. No. 60/184,601, filed Feb. 24, 2000, Holtzman et al.
U.S. Appl. No. 60/169,687, filed Dec. 8, 1999, Chain.
U.S. Appl. No. 60/168,594, filed Nov. 29, 1999, Chalifour et al.
U.S. Appl. No. 09/441,140, filed Nov. 16, 1999, Solomon et al.
Aguzzi et al., "Prion research: the next frontiers," *Nature*, 389:795-798 (1997).
Akiyama et al., "Occurrence of the Diffuse Amyloid β-Protein (Aβ) Deposits With Numerous Aβ-Containing Glial Cells in the Cerebral Cortex of Patients With Alzheimer's Disease," *Glia*, 25:324-331 (1999).
Akiyama et al., "Inflammation and Alzheimer's disease," *Neurobiology of Aging*, 21:383-421 (2000).
Andersen et al., "Do nonsteroidal anti-inflammatory drugs decrease the risk for Alzheimer's disease?", *Neurology*, 45:1441-1445 (1995).
Anderson, J. P., "Exact cleavage site of Alzheimer amyloid precursor in neuronal PC-12 cells," *Neuroscience Letters*, 128(1):126-128 (1991).
Anderson, M. W., "Amending the amyloid hypothesis," *The Scientist*, 18(20):28-29 (2004).
Andrew et al., *Current Protocols in Immunology*, 2.7.1-2.9.8, John Wiley & Sons, Inc. (1997).
Arendiash et al., "Behavioral assessment of Alzheimer's transgenic mice following long-term Aβ vaccination: Task specificity and correlations between Aβ deposition and spatial memory," *DNA and Cell Biology*, 20(11):737-744 (2001).
Associated Press, "Immune cells may promote Alzheimer's, a study finds," *The Boston Globe* (Apr. 13, 1995).
Bacskai et al., "Imaging of amyloid-β deposits in brains of living mice permits direct observation of clearance of plaques with immunotherapy," *Nature Medicine*, 7(3):369-372 (2001).
Bacskai et al., "Non-Fc-mediated mechanisms are involved in clearance of amyloid-β in vivo by immunotherapy," *J. Neurosci.*, 22(18):7873-7878 (2002).
Balbach et al., "Amyloid fibril formation by Aβ$_{16-22}$, a seven-residue fragment of the Alzheimer's β-amyloid peptide, and structural characterization by solid state NMR," *Biochemistry*, 39:13748-13759 (2000).
Bard et al., "Peripherally administered antibodies against amyloid β-peptide enter the central nervous system and reduce pathology in a mouse model of Alzheimer disease," *Nature Medicine*, 6(8):916-919 (2000).
Bard et al., "Epitope and isotype specificities of antibodies to β-amyloid peptide for protection against Alzheimer's disease-like neuropathology," *PNAS*, 100(4):2023-2028 (2003).
Barrow et al., "Solution Conformations and aggregational Properties of Synthetic Amyloid Beta-Peptides of Alzheimer's Disease. Analysis of Circular Dichroism Spectra," *J. Mol. Biol.*, 225(4):1075-1093 (1992).
Bauer et al., "Interleukin-6 and α-2-macroglobulin indicate an acute-phase state in Alzheimer's disease cortices," *FEBS Letters*, 285(1):111-114 (1991).
Beasley, "Alzheimer's traced to proteins caused by aging," Reuters, Apr. 20, 2001 7:56 PM ET.
Bellotti et al., "Application of Monoclonal Anti-idiotypes in the Study of AL Amyloidosi: Therapeutic Implications," *Renal Failure*, 15(3):365-371 (1993).
Benjamini et al., from *Immunology A Short Course*, Second Edition, Chapter 4, Antibody Structure, pp. 49-65, 1991, published by Wiley-Liss, Inc., New York, New York.

Benjamini et al., from *Immunology A Short Course*, Second Edition, pp. 136-138, 143, 73-74, 372-373, and 400-401, 1991, published by Wiley-Liss, Inc., New York, New York.
Benkirane, et al, "Antigenicity and Immunogenicity of Modifed Synthetic Peptides Containing D-Amino Acid Residues," *J. Biol. Chem.*, 268(23):26279-26285 (1993).
Bercovici et al., "Chronic Intravenous Injections of Antigen Induce and Maintain Tolerance in T Cell Receptor-Transgenic Mice," *Eur. J. Immunol.*, 29:345-354 (1999).
Bickel et al., "Site Protected, Cationized Monoclonal Antibody Against Beta Amyloid as a Potential Diagnostic Imaging Technique for Alzheimer's Diseases," *Soc. for Neuroscience Abstracts*, 18:764 (1992).
Blass, "Immunologic Treatment of Alzheimer's Disease," *New England J. Medicine*, 341(22):1694 (1999).
Bodmer et al., "Transforming Growth Factor-Beta Bound to Soluble Derivatives of the Beta Amyloid Precursor Protein of Alzheimer's Disease," *Biochem. Biophys. Res. Comm.*, 171(2):890-897 (1990).
Borchelt et al., "Accelerated Amyloid Deposition in the Brains of Transgenic Mice Coexpressing Mutant Presenilin 1 and Amyloid Precursor Proteins," *Neuron*, 19:939-945 (1997).
Boris-Lawrie et al., "Recent advances in retrovirus vector technology," *Cur. Opin. Genetic Develop.*, 3:102-109 (1993).
Bork et al., "Go hunting in sequence databases but watch out for the traps," *Trends in Genetics*, 12(10):425-427 (1996).
Bork, P., "Powers and Pitfalls in Sequence Analysis: The 70% Hurdle," *Genome Research*, 10:398-400 (2000).
Brenner, S. E., "Errors in genome annotation," *Trends in Genetics*, 15(4):132-133 (1999).
Brice et al., "Absence of the amyloid precursor protein gene mutation (APP717 : Val->Ile) in 85 cases of early onset Alzheimer's disease," *J. Neurology, Neurosurg. Psychiatry*, 56:112-115 (1993).
Burdick et al., "Assembly and aggregation properties of synthetic Alzheimer's A4/β amyloid peptide antigens," *J. Biol. Chem.*, 267:546-555 (1992).
Cameron, "Recent Advances in Transgenic Technology," *Molecular Biotechnology*, 7:253-265 (1997).
Caputo et al., "Therapeutic approaches targeted at the amyloid proteins in Alzheimer's disease," *Clin. Neuropharm.*, 15:414A-414B (1992).
Castillo et al., "Amylin / Islet Amyloid Polypeptide: Biochemistry, Physiology, Patho-Physiology," *Diabete & Metabolisme* (Paris), 21:3-25 (1995).
Center for Biologics Evaluation and Research, U.S. Food and Drug Administration, Thimerosal in Vaccines (Mercury in Plasma-Derived Products), web site contents found at : http://www.fda.gov/cber/vaccine/thimerosal.htm, last updated May 16, 2002.
Chao et al., "Transforming Growth Factor-β Protects human Neurons Against β-Amyloid-Induced Injury," *Soc. Neurosci. Abstracts*, 19:513-7 (1993).
Chapman, "Model behavior," *Nature*, 408:915-916 (2000).
Check, "Battle of the Mind," *Nature*, 422:370-372 (2003).
Chemical Abstract database, Abstract of "Injection of Newborn Mice with Seven Chemical Adjuvants to Help Determine Their Safety in Use in Biologicals," Chemical Abstract database. (Publication date unknown).
Chen et al., "Neurodegenerative Alzheimer-like pathology in PDAPP 717V→F transgenic mice," *Progress in Brain Research*, 117:327-337 (1998).
Chen et al., "A learning deficit related to age and beta-amyloid plaques in a mouse model of Alzheimer's disease," *Nature*, 408(6815):975-979 (2000).
Chen et al., "An Antibody to β Amyloid Precursor Protein Inhibits Cell-substratum Adhesion in Many Mammalian Cell Types," *Neuroscience Letters*, 125:223-226 (1991).
Chishti et al., "Early-onset Amyloid Deposition and Cognitive Deficits in Transgenic Mice Expressing a Double Mutant Form of Amyloid Precursor Protein 695," *J. Biol. Chem.*, 276(24):21562-70 (2001).
Chothia et al., "Domain Association in Immunoglobulin Molecules," *J. Mol. Biol.*, 186:651-663 (1985).
Chromy et al., "Self-assembly of Aβ(1-42) into globular neurotoxins," *Biochemistry*, 42(44):127419-12760 (2003).

Chung et al., "Uptake, Degradation, and Release of Fibrillar and Soluble Forms of Alzheimer's Amyloid β-Peptide by Microglial Cells," *J. Biol. Chem.*, 274(45):32301-32308 (1999).

Cirrito et al., "Amyloid β and Alzheimer disease therapeutics: the devil may be in the details," *J. Clin. Invest.*, 112:321-323 (2000).

Citron et al., "Evidence that the 42- and 40- amino acid forms of amyloid-β protein are generated from the β-amyloid precursor protein by different protease activities," *PNAS*, 93(23):13170-13175 (1996).

Citron, M., "Alzheimer's disease: treatments in discovery and development," *Nat. Neurosci.*, 5:1055-1057 (2002).

Co et al., "Chimeric and humanized antibodies with specificity for the CD33 antigen," *J. Immunol.*, 148:1148-1154 (1992).

Coloma et al., "Transport Across the Primate Blood-Brain Barrier of a Genetically Engineered Chimeric Monoclonal Antibody to the Human Insulin Receptor," *Pharm. Res.*, 17:266-274 (2000).

Conway et al., "Acceleration of oligomerization, not fibrillization, is a shared property of both α-synuclein mutations linked to early-onset Parkinson's disease: Implications for pathogenesis and therapy," *PNAS*, 97(2):571-576 (2000).

Cordell, B., "β-Amyloid formation as a potential therapeutic target for Alzheimer's disease," *Ann. Rev. Pharmacol. Toxicol.*, 34:69-89 (1994).

Costa et al., "Immunoassay for transthyretin variants associated with amyloid neuropathy," *Scand. J. Immunol.*, 38:177-182 (1993).

Cribbs et al, "All-D-Erantiomers of Beta-Amyloid Exhibit Similar Biological Properties to All-L-Beta-Amyloids," *J. Biol. Chem.*, 272:7431-7436 (1997).

Daly, et al., "Detection of the membrane-retained carboxy-terminal tail containing polypeptides of the amyloid precursor protein in tissue from Alzheimer's Disease brain," *Life Sci.*, 63:2121-2131 (1998).

Das et al., "Amyloid-β Immunization Effectively Reduces Amyloid Deposition in FcRy Knock-Out-Mice," *J. Neuroscience*, 23(24):8532-8538 (2003).

DeMattos et al., "Peripheral anti-Aβ antibody alters CNS and plasma clearance and decreases Aβ burden in a mouse model of Alzheimer's disease," *PNAS*, 98(15):8850-8855 (2001).

DeMattos et al., "Peripheral Anti Aβ Antibody Alters CNS And Plasma Aβ Clearance and Decreases Brain Aβ Burden in a Mouse Model of Alzheimer's Disease," *PNAS early edition, 10.1073/pnas. 151261398* (2001).

DeMattos et al., "Plaque-associated disruption of CSF and plasma amyloid-β (Aβ) equilibrium in a mouse model of Alzheimer's disease," *J. Neurochem.*, 81:229-236 (2002).

DeMattos et al., "Brain to plasma amyloid-β efflux: a measure of brain amyoid burden in a mouse model of Alzheimer's disease," *Science*, 295(5563):2264-2267 (2002).

Dialog/Derwent, Abstract of WPI Acc No. 1997-054436/199706: Stable vaccine compsns.—comprise a macrocyclic lactone, a milbemycin, an avermectin, an antigen, a dispersing agent, an adjuvant, a water sol. organic solvent and saline or water, Derwent File 351: Derwent WPI database. (Publication date unknown).

Dickey et al., "Duration and specificity of humoral immune response in mice vaccinated with the Alzheimer's disease-associated β-amyloid 1-42 peptide," *DNA and Cell Biology*, 20(11):723-729 (2001).

Dickson et al., "Neuroimmunology of Alzheimer's disease: a conference report," *Neurobiology of Aging*, 13(6):793-798 (1992), abstract only.

Diomede et al., "Activation effects of a prion protein fragment [PrP-(106-126)] on human leucocytes," *Biochem. J.*, 320:563-570 (1996).

Dodart, "Immunotherapy for Alzheimer's disease: will vaccination work?," *Trends in Molecular Medicine*, 9(3):85-87 (2003).

Dodart et al., "Immunization reverses memory deficits without reducing brain Aβ burden in Alzheimer's disease model," *Nat. Neurosci.*, 5(5):452-457 (2002).

Dodel et al., "Immunotherapy for Alzheimer's disease," *Lancet Neurol.*, 2(4):215-220 (2003).

Doerks et al., "Protein annotation: detective work for function prediction," *Trends in Genetics*, 14(6):248-250 (1998).

Dovey et al., "Functional gamma-secretase inhibitors reduce beta-amyloid peptide levels in brain," *J. Neurochem.*, 76(1):173-181 (2001).

Du et al., "Reduced levels of amyloid beta-peptide antibody in Alzheimer disease," *Neurology*, 57(5):801-5 (2001).

Duff et al., "Mouse model made," *Nature*, 373:476-477 (1995).

Duff et al., "Increased amyloid-β42(43) in brains of mice expressing mutant presenilin 1," *Nature*, 383(6602):710-713 (1996).

Dumery et al., "β-Amyloid protein aggregation: its implication in the physiopathology of Alzheimer's disease," *Pathol. Biol.*, 49:72-85 (2001).

Eck et al., *Goodman and Gilman's The pharmacological basis of therapeutics*, Chapter 5, pp. 77-101 (1996).

El-Agnaf et al., "The influence of the central region containing residues 19-25 on the aggregation properties and secondary structure of Alzheimer's beta-amyloid peptide," *Eur. J. Biochem.*, 256(3):560-569 (1998).

Elan, "Elan and AHP Provide an Update on the Phase 2A Clinical Trial of AN-1792," Press Release. (Jan. 18, 2002).

Elan, "Elan and Wyeth Provide Update on Status of Alzheimer's Collaboration," Press Release (Mar. 1, 2002).

Elizan et al., "Antineurofilament antibodies in a postencephalitic and idiopathic Parkinson's disease," *J. Neurol. Sciences*, 59:341-347 (1983).

Eriksen et al., "NSAID and enantiomers of flurbiprofen target γ-secretase and lower Aβ42 in vivo," *J. Clin. Invest.*, 112(3):440-449 (2003).

Esiri, "Is an effective immune intervention for Alzheimer's disease in prospect?", *Trends in Pharm. Sci.*, 22:2-3 (2001).

Esler et al., "Point substitution in the central hydrophobic cluster of a human β-amyloid congener disrupts peptide folding and abolishes plaque competence," *Biochemistry*, 35:13914-13921 (1996).

Felsenstein et al., "Processing of the β-amyloid precursor protein carrying the familial, Dutch-type, and a novel recombinant C-terminal mutation," *Neuroscience Letters*, 152:185-189 (1993).

Felsenstein et al., "Transgenic Rat and In-Vitro Studies of B-Amyloid Precursor Protein Processing;" *Alzheimer's and Parkinson's Diseases*, Hanin et al. Ed., pp. 401-409, Plenum Press, New York, (1995).

Finch et al., "Evolutionary Perspectives on Amyloid and Inflammatory Features of Alzheimer Disease," *Neurobiology of Aging*, 17(5):809-815 (1996).

Findeis et al, "Modified peptide inhibitors of amyloid B-peptide polymerization," *Biochemistry*, 38:6791-6800 (1999).

Findeis, M. A., "Approaches to discovery and characterization of inhibitors of amyloid β-peptide polymerization," *Biochem. Biophys. Acta*, 1502(1):76-84 (2000).

Fisher et al., "Expression of the amyloid precursor protein gene in mouse oocytes and embryos," *PNAS*, 88:1779-1782 (1991).

Flanders et al., "Altered expression of transforming growth factor-β in Alzheimer's disease," *Neurology*, 45:1561-1569 (1995).

Flood et al., "An amyloid β-Protein fragment, A β 12-28J, equipotently impairs post-training memory processing when injected into different limbic system structures," *Brain Res.* 663(2):271-276 (1994).

Flood, et al, "Topography of a binding site for small amnestic peptides deduced from structure-activity studies: Relation to amnestic effect of amyloid B protein," *PNAS*, 91:380-384 (1994).

Fonseca et al., "The Presence of Isoaspartic Acid in β-Amyloid Plaques Indicates Plaque Age," *Experimental Neurology*, 157(2):277-288 (1999).

Frautschy et al., "Effects of injected Alzheimer β-amyloid cores in rat brain," *PNAS*, 88:8362-8366 (1991).

Frazer et al., "Immunoglobulins: Structure and Function," chapter 3, pp. 37-74 from *Fundamental Immunology, fourth edition*, W.E. Paul, eds., Lippincott-Raven publishers, Philadelphia (1999).

Frenkel et al., "Generation of auto-antibodies towards Alzheimer's disease vaccination," *Vaccine*, 19:2615-2619 (2001).

Frenkel et al., "High affinity binding monoclonal antibodies to the sequential epitope EFRH of β-amyloid peptide is essential for modulation of fibrillar aggregation," *J. of Neuroimmunology*, 95:136-142 (1999).

Frenkel et al., "Immunization against Alzheimer's β-amyloid plaques via EFRH phage administration," *PNAS*, 97:11455-11459 (2000).

Frenkel et al., "N-terminal EFRH sequence of Alzheimer's β-amyloid peptide represents the epitope of its anti-aggregating antibodies," *J. of Neuroimmunology*, 88:85-90 (1998).

Frenkel, et al., "Modulation of Alzheimer's β-amyloid neurotoxicity by site-directed single chain antibody," *J. of Neuroimmunology*, 106:23-31 (2000).

Frenkel et al., "Reduction of β-amyloid plaques in brain of transgenic mouse model of Alzheimer's disease by EFRH-phage immunization," *Vaccine*, 21(11-12):1060-1065 (2003).

Frenkel et al., "Towards Alzheimer's β-amyloid vaccination," *Biologicals*, 29(3-4):243-247 (2001).

Friedland et al., "Development of an anti-Aβ monoclonal antibody for in vivo imaging of amyloid angiopathy in Alzheimer's disease," *Mol. Neurology*, 9:107-113 (1994).

Friedland, et al., "Neuroimaging of Vessel Amyloid in Alzheimer's Disease," in *Cerebrovascular Pathology in Alzheimer's Disease*, eds. de la Torre and Hachinski, New York Academy of Sciences, New York, New York (1997).

Furlan et al., "Vaccination with amyloid-β peptide induces autoimmune encephalomyelitis in C57/BL6 mice," *Brain*, 126:285-291 (2003).

Games et al., "Alzheimer-type neuropathology in transgenic mice overexpressing V717F β-amyloid precursor protein," *Nature*, 373(6514):523-527 (1995).

Games et al., "Prevention and Reduction of AD-type Pathology in PDAPP Mice Immunized with $A\beta_{1-42}$," *Annals of the New York Academy of Science*, 920:274-284 (2000).

Gandy et al., "Amyloidogenesis in Alzheimer's disease: some possible therapeutic opportunities," *TiPS*, 13:108-113 (1992).

Gardella et al., "Intact Alzheimer amyloid precursor protein (APP) is present in platelet membranes and is encoded by platelet mRNA," *Biochem. Biophys. Res. Comm.*, 173:1292-1298 (1990).

Gaskin et al., "Human antibodies reactive with beta-amyloid protein in Alzheimer's disease," *J. Exp, Med.*, 177:1181-1186 (1993).

Geddes, "N-terminus truncated β-amyloid peptides and C-terminus truncated secreted forms of amyloid precursor protein: distinct roles in the pathogenesis of Alzheimer's disease," *Neurobiology of Aging*, 20:75-79 (1999).

Gelinas et al., "Immunotherapy for Alzheimer's disease," *PNAS*, 101(supp. 2):14657-14662 (2004).

Ghiso et al., "Epitope map of two polyclonal antibodies that recognize amyloid lesions in patients with Alzheimer's disease," *Biochem. J.*, 282 (Pt 2):517-522 (1992).

Giulian et al., "Specific domains of β-amyloid from Alzheimer plaque elicit neuron killing in human microglia," *J. Neurosci.*, 16 (19):6021-6037 (1996).

Giulian, et al., "The HHQK Domain of b-Amyloid Provides a Structural Basis for the Immunopathology of Alzheimer's Disease," *J. Biol. Chem.*, 273:29719-29726 (1998).

Glenn et al., "Skin immunization made possible by cholers toxin," *Nature*, 391:851 (1998).

Glenner et al., "Alzheimer Disease and Downs Syndrome: Sharing of A Unique Cerebrovascular Amyloid Fibril Protein," *Biochem. Biophys. Res. Comm.*, 122(3): 1131-1135 (1984).

Glenner et al., "Alzheimer's Disease: Initial Report of the Purification and Characterization of a Novel Cerebrovascular Amyloid Protein," *Biochem. Biophys. Res. Comm.*, 120(3): 885-890 (1994).

Goate et al., "Segregation of a missense mutation in the amyloid precursor protein gene with familial Alzheimer's disease," *Nature*, 349:704-706 (1991).

Goldfarb et al., "The Transmissible Spongiforms Encephalopathies," *Ann. Rev. Med.*, 46:57-65 (1995).

Goldsby et al., "Vaccines," Chapter 18 from *Immunology, 4th Edition*, W.H. Freeman and Company, New York, pp. 449-465 (2000).

Goldsteins et al., "Goldsteins et al., Exposure of cryptic epitopes on transthyretin only in amypoid and in amyloidogenic mutants," *PNAS*, 96:3108-3113 (1999).

Gong et al., "Alzheimer's disease-affected brain: presence of oligomeric Aβligands (ADDLs) suggests a molecular basis for reversible memory loss," *PNAS*, 100(18):10417-10422 (2003).

Gonzales-Fernandez et al., "Low antigen dose favors selection of somatic mutants with hallmarks of antibody affinity maturation," *Immunology*, 93:149-153 (1998).

Gorevic et al., "Ten to fourteen residue peptides of Alzheimer's disease protein are sufficient for amyloid fibril formation and its characteristic X ray diffraction pattern" *Biochem. and Biophy. Res. Commun.*, 147(2):854-862 (1987).

Gortner, *Outlines of Biochemistry*, pp. 322-323, John Wiley & Sons, Inc., New York (1949).

Gozes et al., "Neuroprotective strategy for Alzheimer disease: Intranasal administration of a fatty neuropeptide," *PNAS*, 93:427-432 (1996).

Gravina et al., "Amyloid β Protein (Aβ) in Alzheimer's Disease," *J. Biol. Chem.*, 270(13):7013-7016 (1995).

Greenberg et al., "Alzheimer disease's double-edged vaccine," *Nat. Med.*, 9(4):389-390 (2003).

Grubeck-Loebenstein, et al., "Immunization with β-amyloid: could T-cell activation have a harmful effect?", *TINS*, 23:114 (2000).

Gupta et al., "Differences in the immunogenicity of native and formalized cross reacting material (CRM197) of diptheria toxin in mice and guinea pigs and their implications on the development and control of diphtheria vaccine based on CRMs," *Vaccine*, 15(12/13): 1341-1343 (1997).

Haass et al. "Amyloid beta-peptide is produced by cultured cells during normal metabolism," *Nature*, 359(6393):322-325 (1992).

Haass et al., "Protofibrils, the unifying toxic molecule of neurodegenerative disorders?," *Nature Neuroscience*, 4(9):859-860 (2001).

Haass, C., "New hope for Alzheimer disease vaccine," *Nat Med.*, 8(11):1195-1196 (2002).

Haga et al., "Synthetic Alzheimer amyloid β/A4 peptides enhance production of complement C3 componenet by cultured microglial cells," *Brain Research*, 601:88-94 (1993).

Hanan and Solomon, "Inhibitory effect of monoclonal antibodies on Alzheimer's β-amyloid peptide aggregation," *Int. J. Exp. Clin. Invest.*, 3:130-133 (1996).

Hanes et al., "New advances in microsphere-based single-dose vaccines," *Advanced Drug Delivery Reviews*, 28: 97-119 (1997).

Hardy, "Amyloid, the presenilins and Alzheimer's disease," *TINS*, 20(4): 154-159 (1997).

Hardy, John, "New Insights into the Genetics of Alzheimer's Disease," *Annals of Med.*, 28:255-258 (1996).

Harigaya, et al., "Modified amyloid β protein ending at 42 or 40 with different solubility accumulates in the brain of Alzheimer's disease," *Biochem. Biophys. Res. Comm.*, 211:1015-1022 (1995).

Harrington et al., "Characterization of an epitope specific to the neuron-specific isoform of human enolase recognized by a monoclonal antibody raised against a synthetic peptide corresponding to the C-terminus of β / A4-protein," *Biochimica Biophysica Acta*, 1158:120-128 (1993).

Hazama, et al., "Intranasal Immunization Against Herpes Simplex Virus Infection by Using a Recombinant Glycoprotein D Fused With Immunomodulating Proteins, the B Subunit of *Escherichia coli* Heat-Labile Enterotoxin and Interleukin-2," *Immunology*, 78:643-649 (1993).

He et al., "Humanization and pharmacokinetics of a monoclonal antibody with specificity for both E- and P- selectin," *J. Immunol.* 160:1029-1035 (1998).

Helmuth, "Further Progress on a β-Amyloid Vaccine," *Science*, 289:375 (2000).

Herlyn et al., "Monoclonal antibodies in cell-mediated cytotoxicity against human melanoma and colorectal carcinoma*," *Eur. J. Immunol.*, 9:657-659 (1979).

Hilbich et al., "Aggregation and secondary structure of synthetic amyloid βA4 peptides of Alzheimer's disease," *J. Mol. Biol.*, 218:149-163 (1991).

Hilbich et al., "Substitutions of hydrophobic amino acid reduce the amyloidogenicity of Alzheimer's disease βA4 peptides" *J. Mol. Biol.*, 228:460-473 (1992).

Hilbich et al., "Human and rodent sequence analogs of Alzheimer's amyloid βA4 share similar properties and can be solubilized in buffers of pH 7.4," *Eur. J. Biochem.*, 201:61-69 (1991).

Hock et al., "Antibodies against β-Amyloid Slow Cognitive Decline in Alzheimer's Disease," *Neuron.* 38:542-554 (2003).

Hock et al., "Generation of antibodies specific for β-amyloid by vaccination of patients with Alzheimer disease," *Nat. Med.*, 8(11):1270-1275 (2002).

Holtzman et al., "Aβ immunization and anti-Aβ antibodies: potential therapies for the prevention and treatment of Alzheimer's disease," *Advanced Drug Delivery Reviews*, 54(12):1603-1613 (2002).

Hsiao et al., "Correlative Memory Deficits, Aβ Elevation, and Amyloid Plaques in Transgenic Mice," *Science*, 274: 99-102 (1996).

Huberman et al., "Correlation of cytokine secretion by mononuclear cells of Alzheimer's patients and their disease stage," *J. Neuroimmunology*, 52:147-152 (1994).

Human Immunology & Cancer Program brochure, from The University of Tennessee Medical Center/ Graduate School of Medicine, Knoxville, Tennessee (publication date unkown).

Hyman et al., "Molecular Epidemiology of Alzheimer's Disease," *N. E. J. Medicine*, 333(19):1283-1284 (1995).

Ikeda, et al., "Immunogold labeling of cerebrovascular and neuritic plaque amyloid fibrils in Alzheimer's disease with an anti-β protein monoclonal antibody," *Lab. Invest.*, 57:446-449 (1987).

Irizarry et al., "Aβ Deposition Is Associated with Neuropil Changes, but not with Overt Neuronal Loss in the Human Amyloid Precursor Protein V717F (PDAPP) Transgenic Mouse," *J. Neuroscience*, 17(18):7053-7059 (1997).

Irizarry et al., "Alzheimer disease therapeutics," *J. Neuropathol. Exo. Neurol.*, 60(10):923-928 (2001).

Itagaki et al., "Relationship of microglia and astrocytes to amyloid deposits of Alzheimer's disease," *J. Neuroimmunology*, 24:173-182 (1989).

Iwatsubo et al., "Visualization of Aβ42(43) and Aβ40 in Senile Plaques with End-Specific Aβ Monoclonals: Evidence That an Initially Deposited Species is Aβ 42(43)," *Neuron.* 13:45-53 (1994).

Jahrling et al., "Opsonization of Alphaviruses in Hamsters," *J. Medical Virology*, 12:1-16 (1983).

Jakes et al., "Characterisation of an Antibody Relevant to the Neuropathology of Alzheimer Disease," *Alzheimer Disease and Associated Disorders*, 9(1):47-51 (1995).

Jansen et al., "Immunotoxins: Hybrid Molecules Combining High Specificity and Potent Cytotoxicity," *Immun. Rev.*, 62: 185-216 (1982).

Janus et al., "A beta peptide immunization reduces behavioural impairment and plaques in a model of Alzheimer's disease," *Nature*, 408(6815):979-982 (2000).

Janus et al., "Transgenic mouse models of Alzheimer's Disease," *Physiol. Behav.*, 73(5):873-886 (2001).

Jen, et al., "Preparation and purification of antisera against different regions or isoforms of b-amyloid precursor protein," *Brain Research Protocols*, 2:23-30 (1997).

Joachim et al., "Antibodies to Non-beta Regions of the Beta-amyloid Precursor Protein Detect a Subset of Senile Plaques," *Am. J. of Pathology*, 138:373-384 (1991).

Jobling et al., "Analysis of structure and function of the B subunit of cholera toxin by the use of site-directed mutagenesis," *Molecular Microbiology*, 5(7):1755-1767 (1991).

Johnson-Wood et al., "Amyloid precursor protein processing and $A\beta_{42}$ deposition in a transgenic mouse model of Alzheimer disease," *PNAS*, 94:1550-1555 (1997).

Johnstone et al., Nuclear and Cytoplasmic Localization of the β-Amyloid Peptide (1-43) in Transfected 293 Cells, *Biochem. Biophys. Res. Comm.*, 220:710-718 (1996).

Jorbeck et al., "Artificial *Salmonella* Vaccines: *Salmonella typhimurium* O-antigen-Specific Oligosaccharide-Protein Conjugates Elicit Opsonizing Antibodies that Enhance Phagocytosis," *Infection and Immunity*, 32(2):497-502 (1981).

Kalaria, R. N., "Serum amyloid P and related molecules associated with the acute-phase response in Alzheimer's disease," *Res. Immunology*, 143:637-641 (1992).

Katzav-Gozansky et al., "Effect of monoclonal antibodies in preventing carboxypeptidase A aggregation," *Biotechnol. Appl. Biochem.*, 23:227-230 (1996).

Kawabata et al., "Amyloid plaques, neurofibrillary tangles and neuronal loss in brains of transgenic mice overexpressing a C-terminal fragment of human amyloid precursor protein," *Nature*, 354:476-478 (1991).

Kayed et al., "Conformational Transitions of Islet Amyloid Polypeptide (IAPP) in Amyloid Formation In Vitro," *J. Mol. Biol.*, 287:781-796 (1999).

Kelly, J. W., "Alternative conformations of amyloidogenic proteins govern their behavior," *Current Opinion in Structural Biology*, 6:11-17 (1996).

Kettleborough et al., "Humanization of a mouse monoclonal antibody by CDR-grafting: the importance of framework residues on loop conformation," *Protein Engineering*, 4(7):773-783 (1991).

Kida, et al., "Early amyloid-β deposits show different immunoreactivity to the amino- and carboxy- terminal regions of b-peptide in Alzheimer's disease and Down's syndrome brain," *Neuroscience Letters*, 193:105-108 (1995).

Klein et al., "Targeting small Aβ oligomers: the solution to an Alzheimer's disease conundrum?," *Trends in Neurosciences*, 24(4):219-224 (2001).

Kofler et al. "Mechanism of allergic cross-reactions-III. cDNA cloning and variable-region sequence analysis of two IgE antibodies specific for trinitrophenyl." *Mol Immunol.* 29(2):161-6 (1992).

Kofler et al., "IgE antibody light chain (VJ) [*Mus musculus*]." GenBank Accession No. CAA46659. Retrieved from the internet at http://www.ncbi.nlm.nih.gov/entrez/viewer.fcgi?db=protein &val=1870480 on Aug. 26, 2005.

Kofler et al. "*M.musculus* DNA for IgE antibody light chain (VJ)." GenBank Accession No. X65775. Retrieved from the internet at http://www.ncbi.nlm.nih.gov/entrez/viewer.fcgi?db=nucleotide &val=312078 on Aug. 26, 2005.

Konig et al., "Development and Characterization of a Monoclonal Antibody 369.2B Specific for the Carboxyl-Terminus of the βA4 Peptide," *Annals of NY Acad. Sci.* 777:344-355 (1996).

Kotilinek et al., "Reversible memory loss in a mouse transgenic model of Alzheimer's disease," *J. Neurosci.*, 22(15):6331-6335 (2002).

Koudinov et al., "The soluble form of Alzheimer's amyloid beta protein is complexed to high density lipoprotein 3 and very high density lipoprotein in normal human plasma," *Biochem. & Biophys. Res. Comm.* 205:1164-1171 (1994).

Kovács et al., "Mutations of the Prion Protein Gene Phenotypic Spectrum," *J. Neurol.*, 249:1567-1582 (2002).

Krishnan et al.., "Correlation between the amino acid position of arginine in VH-CDR3 and specificity for native DNA among autoimmune antibodies." *J Immunol.* 157(6):2430-9 (1996).

Krishnan et al. "anti-DNA immunoglobulin light chain IgG [*Mus musculus*]." GenBank Accession No. AAB488000. Retrieved from the internet at http://www.ncbi.nlm.nih.gov/entrez/viewer. fcgi?db=protein&val=1870480 on Aug. 26, 2005.

Kuo et al., "High levels of circulating Abeta42 are sequestered by plasma proteins in Alzheimer's disease," *Biochem. Biophys. Res. Comm.*, 257 (3):787-791 (1999).

Lambert et al., "Diffusible, nonfibrillar ligands derived from Aβ1-42 are potent central nervous system neurotoxins," *PNAS*, 95:6448-6453 (1998).

Lambert et al., "Vaccination with soluble Aβ oligomers generates toxicity-neutralizing antibodies," *J. Neurochem.*, 79:595-605 (2001).

Lampert-Etchells et al., "Regional Localization of Cells Containing Complement C1q and C4 mRNAs in the Frontal Cortex During Alzheimer's Disease," *Neurodegeneration*, 2:111-121 (1993).

Langer, "New Methods of Drug Delivery," *Science*, 249:1527-1532 (1990).

Lannfelt et al., "Alzheimer's disease: molecular genetics and transgenic animal models," *Behavioural Brain Res.*, 57:207-213 (1993).

Lansbury, Peter T., "Inhibition of amyloid formation: a strategy to delay the onset of Alzheimer's disease," *Curr. Ops. in Chemical Biology*, 1:260-267 (1997).

Lee et al., "Aβ immunization: Moving Aβ peptide from brain to blood," *PNAS*, 98(16):8931-8932 (2001).

Lemere et al., "Mucosal Administration of Aβ Peptide Decreases Cerebral Amyloid Burden In Pd-App Transgenic Mice," *Society for Neuroscience Abstracts*, 25(part)I, Abstract 519.6, 29th Annual Meeting, (Oct. 23-28, 1999).

Lemere, et al., "Nasal Aβ treatment induces anti-Aβ antibody production and decreases cerebral amyloid burden in PD-APP mice," *Annals of the NY Acad. Sci.*, 920:328-331 (2000).

Lemere et al., "Intranasal immunotherapy for the treatment of Alzheimer's disease: *Escherichia coli* LT and LT(R192G) as mucosal adjuvants," *Neurobiology of Aging*, 23(6):991-1000 (2002).

Leverone et al., "Aβ1-15 is less immunogenic than Aβ1-40/42 for intranasal immunization of wild-type mice but may be effective for 'boosting'," *Vaccine*, 21:2197-2206 (2003).

Levitt, M., "Molecular dynamics of native protein," *J. Mol. Biol.*, 168:595-620 (1983).

Levy et al., "Immunization for Alzheimer's disease: A shot in the arm or a whiff?," *American Neurological Assoc*, 48:553-554 (2000).

Li et al., "Thermal Stabilization of Carboxypeptidase A as a Function of PH and Ionic Milieu," *Biochem. Mol. Biol. Int.*, 43(3):601-611 (1997).

Livingston et al., "The Hepatitis B Virus-Specific CTL Responses Induced in Humans by Lipopeptide Vaccination Are Comparable to Those Elicited by Acute Viral Infection," *J. Immunol.*, 159:1383-1392 (1997).

Lopez et al., "Serum auto-antibodies in Alzheimer's disease," *Acta. Neurol. Scand.*, 84:441-444 (1991).

Lue et al., "Soluble β-amyloid Peptide Concentration as a Predictor of Synaptic Change in Alzheimer's Disease," *Am. J. Pathol.*, 155:853-562 (1999).

Maggio et al., "Brain Amyloid—A Physicochemical Perspective," *Brain Pathology*, 6:147-162 (1996).

Majocha et al., "Development of a Monoclonal Antibody Specific for β/A4 Amyloid in Alzheimer's Disease Brain for Application to In Vitro Imaging of Amyloid Angiopathy," *The J. of Nuclear Med.*, 33:2184-2189 (1992).

Mak, et al., "Polyclonals to b-amyloid (1-42) identify most plaque and vascular deposits in Alzheimer cortex, but not striatum," *Brain Research*, 667:138-142 (1994).

Mann, et al., "Amyloid β protein (Aβ) deposition in chromosome 14-linked Alzheimer's disease: Predominance of $A\beta_{42(43)}$," *Annals of Neurology*, 40:149-156 (1996).

Mann, et al., "The extent of amyloid deposition in brain in patients with Down's syndrome does not depend upon the apolipoprotein E genotype," *Neuroscience Letters*, 196:105-108 (1995).

Marshall, E., "Gene Therapy'S Growing Pains," *Science*, 269:1050-1055 (1995).

Masliah et al., "β-Amyloid peptides enhance α-synuclein accumulation and neuronal deficits in a transgenic mouse model linking Alzheimer's disease and Parkinson's disease," *PNAS*, 98(21):12245-12250 (2001).

Masliah et al., "Comparison of Neurodegenerative Pathology in Transgenic Mice Overexpressing V717F β-Amyloid Precursor Protein and Alzheimer's Disease," *J. Neuroscience*, 16(18):5795-5811 (1996).

Masters et al., "Amyloid Plaque core protein in Alzheimer Disease and Down Syndrome," *PNAS*, 82:4245-4249 (1985).

Mattson, "Cellular actions of beta-amyloid precursor protein and its soluble and fibrillogenic derivatives," *Physiol. Rev.*, 77(4):1081-132 (1997).

Mattson et al., "Good and bad amyloid antibodies," *Science*, 301(5641):1845-1849 (2003).

McGee et al., "The encapsulation of a model protein in poly (D, L lactide-co-glycolide) microparticles of various sizes: an evaluation of process reproducibility," *J. Micro. Encap.*, 14(2):197-210 (1997).

McGeer, et al., "Immunohistochemical localization of beta-amyloid precursor protein sequences in Alzheimer and normal brain tissue by light and electron microscopy," *J. of Neuroscience Res.*, 31:428-442 (1992).

McLaurin et al., "Therapeuticaly effective antibodies against amyloid-β peptide target amyloid-β residues and 4-10 and inhibit cytotoxicity and fibrillogenesis," *Nat. Med.*, 8(11):1263-1269 (2002).

McLean et al., "Soluble pool of Aβ amyloid as a determinant of severity of neurodegeneration in Alzheimer's disease," *Amer. Neurological Assoc.* 46:860-866 (1999).

McNeal et al., "Stimulation of local immunity and protection in mice by intramuscular immunization with triple- or double-layered rotavirus particles and QS-21," *Virology*, 243:158-166 (1998).

Meda et al., "Activation of microglial cells by β-amyloid protein and interferon-γ," *Nature*, 374:674-650 (1995).

Mena, et al., "Monitoring pathological assembly of tau and β-amyloid proteins in Alzheimer's disease," *Acta Neuropathol.*, 89:50-56 (1995).

Merluzzi, et al., "Humanized antibodies as potential drugs for therapeutic use," *Adv Clin Path.*, 4(2):77-85 (2000).

Miller et al., "Antigen-driven Bystander Suppression after Oral Administration of Antigens," *J. Exp. Med.*, 174:791-798 (1991).

Monsonego et al., "Immune hyporesponsiveness to amyloid β-peptide in amyloid precursor protein transgenic mice: Implications for the pathogenesis and treatment of Alzheimer's disease," *PNAS*, 98(18):10273-10278 (2001).

Monsonego et al., "Increased T cell reactivity to amyloid β protein in older humans and patients with Alzheimer's disease," *J. Clin. Invest.*, 112(3):415-422 (2003).

Monsonego et al., "Immunotherapeutic approaches to Alzheimer's disease," *Science*, 302(5646):834-838 (2003).

Morgan, et al., "A beta peptide vaccination prevents memory loss in an animal model of Alzheimer's disease," *Nature*, 408(6815):982-985 (2000).

Mori et al., "Mass Spectrometry of Purified Amyloid β Protein in Alzheimer's Disease," *J. Biol. Chem.*, 267(24):17082-17088 (1992).

Morris, et al., "The Consortium to Establish a registry for Alzheimer's Disease (CERAD)," *Neurology*, 39:1159-1165 (1989).

Munch et al., "Potentional neurotoxic inflammatory response to Aβ vaccination in humans," *J. Neural Transm.*, 109:1081-1087 (2002).

Munson eds., *Principals of Pharmacology: Basic Concepts & Clinical Applications*, pp. 47-48, Chapman & Hall, New York, New York (1995).

Murphy et al., "Development of a Monoclonal Antibody Specific for the COOH-Terminal of β-Amyloid 1-42 and Its Immunohistochemical Reactivity in Alzheimer's Disease and Related Disorders," *Am. J. Pathology*, 144(5):1082-1088 (1994).

Mutschler et al., *Drug Actions: Basic Principles and Therapeutic Aspects* pp. 7, 11-12, Medpharm Scientific Publishers, Stuttgart, Germany (1995).

Nakamura et al., "Histopathological studies on senile plaques and cerebral amyloid angiopathy in aged cynomologus monkeys," *Exp. Anim.*, 43:711-718 (1995).

Nakamura, et al., "Carboxyl end-specific monoclonal antibodies to amyloid β protein (Aβ) subtypes (Aβ40 and Aβ42(43) differentiate Ab in senile plaques and amyloid angiopathy in brains of aged cynomolgus monkeys," *Neuroscience Letters*, 201:151-154 (1995).

Nakayama, et al., "Histopathological studies of senile plaques and cerebral amyloidosis in cynomolgus monkeys," *J. of Med. Primatology*, 27:244-252 (1998).

Nalbantoglu, J., "Beta-amyloid protein in Alzheimer's disease," *Can. J. Neurol. Sci.*, 18(3 suppl.):424-427 (1991), abstract only.

Naslund et al., "Correlation between elevated levels of amyloid β peptide in the brain and cognitive decline," *J. Am. Med. Assoc.*, 283:1571 (2000).

Nathanson et al., "Bovine Spongiform Encephalopathy (BSE): Causes and Consequences of a Common Source Epidemic," *Am. J. Epidemiol.*, 145(11):959-969 (1997).

New York Times National, "Anti-Inflammatory Drugs May Impede Alzheimer's," (Feb. 20, 1994).

Newcombe et al., "Solubility characteristics of isolated amyloid fibrils," *Biochim. Biophys. Acta*, 104:480-486 (1965).

Ngo et al., "Computational Complexity, Protein Structure Prediction, and the Levinthal Paradox," pp. 492-495 from Chapter 14 of

*The Protein Folding Problem and Tertiary Structure Prediction*, Merz et al., eds., Birkhauser Boston (1994).
Nicoll et al., "Neuropathology of human Alzheimer's disease after immunization with amyloid-β peptide: a case report," *Nature Medicine*, 9(4):448-452 (2003).
Niemann, "Transgenic farm animals get off the ground," *Transgenic Research*, 7:73-75 (1998).
Novotny et al., "Structural invariants of antigen binding: Comparison of immunoglobulin $V_L$-$V_H$ and $V_L$-$V_L$ domain dimmers," *PNAS*, 82:4592-4596 (1985).
Orkin et al., *Report and Recommendations of the Panel to Assess the NIH Investment in Research on Gene Therapy*, Dec. 7, 1995.
Paganetti et al., "Amyloid precursor protein truncated at any of the γ-secretase sites is not cleaved to β-amyloid," *J. Neurosci. Res.*, 46(3):283-293 (1996).
Palha et al., "Antibody recognition of amyloidogenic transthyretin variants in serum of patients with familial amyloidiotic polyneuropathy," *J. Mol. Med.*, 7:703-707 (2001).
Pallitto et al., "Recognition sequence design for peptidyl modulators of β-amyloid aggregation and toxicity," *Biochemistry*, 38(12):3570-3578 (1999).
Pan et al., "Antibodies to β-Amyloid Decrease the Blood-to-Brain Transfer of β-Amyloid Peptide," *Exp. Biol. Med.*, 227(8):609-615 (2002).
Pardridge et al., "Chimeric peptides as a vehicle for peptide pharmaceutical delivery through the blood-brain barrier," *Biochem. Biophys. Res. Comm.*, 146:307-313 (1987).
Paresce et al., "Microglial cells influence aggregates of the Alzheimer's disease amyloid beta-protein via a scavenger receptor," *Neuron*, 17:553-565 (Sep. 1996).
Paul et al., "Transdermal immunization with large proteins by means of ultradeformable drug carriers," *Eur. J. Immunol.*, 25: 3521-3524 (1995).
PCT Search Report of Dec. 14, 2004 for application PCT/US04/02856.
Persson et al., "IgG subclass-associated affinity differences of specific antibodies in humans," *J. Immunology*, 140(11):3875-3879 (1988), abstract only.
Perutz et al., "Amyloid fibers are water-filed nanotubes," *PNAS*, 99(8):5591-5595 (2002).
Peterson, et al., "Recombinant Antibodies: Alternative Strategies for Developing and Manipulating Murine-Derived Monoclonal Antibodies," *Laboratory Animal Science*, 46(1):8-14 (1996).
Pfeifer et al., "Cerebral hemorrhage after passive anti-Aβ immunotherapy," *Science*, 298(5597):1379 (2002).
Philippe, et al. "Generation of a monoclonal antibody to the carboxy-terminal domain of tau by immunization with the amino-terminal domain of the amyloid precursor protein," *J. of Neuroscience Res.*, 46:709-719 (1996).
Poduslo et al., "Permeability of proteins at the blood-brain barrier in the normal adult mouse and double transgenic mouse model of Alzheimer's disease," *Neurobiol. Dis.*, 8(4):555-567 (2001).
Prieels et al., "Synergistic adjuvants for vaccines," *Chemical Abstracts*, 120(8):652, col. 1, abstract 86406t (1994).
Prusiner et al., "Ablation of the prion protein (PrP) gene in mice prevents scrapie and facilitates production of anti-PrP antibodies," *PNAS*, 90:10608-10612 (1993).
Queen et al., "A humanized antibody that binds to the interleukin 2 receptor," *PNAS*, 86:10029-10033 (1989).
Quon et al., "Formation of β-Amyloid protein deposits in brains of transgenic mice," *Nature*, 352:239-241 (1991).
Ragusi et al., "Redistribution of Imipramine from Regions of the Brain Under the Influence of Circulating Specific Antibodies," *J. Neurochem.*, 70(5):2099-2105 (1998).
Raso, "Immunotherapy of Alzheimer's Disease," *Immunotherapy Weekly*, Abstract (Apr. 2, 1998).
Raso, V.A., Grant application # R43 AGI 5746-01 (non-redacted version), "Immunotherapy of Alzheimer's Disease" (publication date unknown).
Raso, V.A., Grant application # R43 AGI 5746-01 (redacted version), "Immunotherapy of Alzheimer's Disease" (publication date unknown).

"Researchers Develop Blood Test to Diagnose Alzheimer's- Type Changes in Mice," downloaded from www.businesswire.com on Dec. 15, 2004.
Rogers et al., "Complement activation by β-amyloid in Alzheimer Disease," *PNAS*, 89:1-5 (1992).
Rossor et al., "Alzheimer's Disease Families with Amyloid Precursor Protein Mutations," *Annals of New York Academy of Sciences*, 695:198-202 (1993).
Rudinger, "Characteristics of the Amino Acids as Components of a Peptide Hormone Sequence," in *Peptide Hormones*, J.A. Parson, ed. University Park Press, Baltimore, pp. 1-7 (1976).
Saido et al., "Spatial Resolution of Fodrin Proteolysis in Postichemic Brain," *J. Biol. Chem.*, 268(33):25239-25243 (1993).
Saido et al., "Spatial Resolution of the Primary β-Amyloidogenic Process Induced in Postischemic Hippocampus," *J. Biol. Chem.*, 269(21):15253-15257 (1994).
Saito et al., "Vector-mediated delivery of $^{125}$I-labeled β-amyloid peptide $Ab^{1-40}$ through the blood-brain barrier and binding to Alzheimer's disease amyloid of the $Aβ^{1-40}$ vector complex," *PNAS*, 92:10227-10231 (1995).
Saitoh, N. et al., "Immunological analysis of Alzheimer's disease using anti- β-protein monoclonal antibodies," *Sapporo Med. J.*, 60:309-320 (1991).
Sasaki et al., "Human choroid plexus is an uniquely involved area of the brain in amyloidosis: a histochemical, immunohistochemical and ultrastructural study," *Brain Res.*, 755:193-201 (1997).
Schenk et al., "Immunization with amyloid-β attenuates Alzheimer-disease-like pathology in the PDAPP mouse," *Nature*, 400:173-177 (1999).
Schenk et al., "Therapeutic Approaches Related to Amyloid-β Peptide and Alzheimer's Disease," *J. Med. Chem.*, 38(21):4141-4154 (1995).
Schenk et al., "β-peptide immunization," *Arch. Neurol.*, 57:934-936 (2000).
Schenk et al., "Immunotherapy with beta-amyloid for Alzheimer's disease: a new frontier," *DNA Cell Biol.*, 20(11):679-81 (2001).
Schenk, D., "Amyloid-β immunotherapy for Alzheimer's disease: the end of the beginning," *Nature Reviews*, 3:824-828 (2002).
Schmid, R. E., "Study suggest Alzheimer vaccine fix," from www.msnbc.com/news, pp. 1-5 (2002).
Schwarzman et al., "Transthyretin sequesters amyloid β protein and prevents amyloid formation," *PNAS*, 91:8368-8372 (1994).
Seidl, K.J. et al. "Predominant VH genes expressed in innate antibodies are associated with distinctive antigen-binding sites." *Proc Natl Acad Sci U S A*. 96(5):2262-7 (1999).
Seidl, K.J. et al., "Immunoglobulin heavy chain VH3609-JH3 region [*Mus musculus*]." GenBank Accession No. AAD26773. Retrieved from the internet at http://www.ncbi.nlm.nih.gov/entrez/viewer.fcgi?db=protein&val=4633434 on Aug. 26, 2005.
Sela et al, "Different roles of D-amino acids in immune phenomena," *FASEB J*, 11(6):449-456 (1999).
Selkoe, "Alzheimer's Disease: A Central Role for Amyloid," *J. Neuropathol. Exp. Neurol.*, 53(5): 438-447 (1994).
Selkoe, "Physiological production of the β-amyloid protein and the mechanism of Alzheimer's disease," *Trends in Neurosciences*, 16(10): 403-409 (1993).
Selkoe, "The cell biology of beta-amyloid precursor protein and presenilin in Alzheimer's disease," *Trends Cell Biol.*, 8(11):447-53 (1998).
Selkoe, D.J., "Imaging Alzheimer's Amyloid," *Nat. Biotech.*, 18:823-824 (2000).
Selkoe, Dennis J., "Alzheimer's Disease: Genotypes, Phenotype, and Treatments," *Science*, 275:630-631 (1997).
Selkoe, Dennis J., "Amyloid Protein and Alzheimer's Disease . . . ," *Scientific American*, pp. 68-78 (1991).
Selkoe, Dennis J., "In the Beginning . . . ," *Nature*, 354:432-433 (1991).
Selkoe, Dennis J., "The Molecular pathology of Alzheimer's Disease," *Neuron*, 6:487-498 (1991).
Selkoe, D. J., "Alzheimer's disease is a synaptic failure," *Science*, 298(5594):789-791 (2002).

Sergeant et al., "Truncated beta-amyloid peptide species in pre-clinical Alzheimer's disease as new targets for the vaccination approach," *J. Neurochem.*, 85(6):1581-1591 (2003).
Seubert et al., "Isolation and quantification of soluble Alzheimer's β-peptide from biological fluids," *Nature*, 359: 325-327 (1992).
Shiosaka, S., "Attempts to make models for Alzheimer's disease," *Neuroscience Res.*, 13:237-255 (1992).
Sigmund, "Viewpoint: Are Studies in Genetically Altered Mice Out of Control,"*Arterioscler Thromb Vasc Biol.*, 20:1425-1429 (2000).
Sigurdsson et al., "A safer vaccine for Alzheimer's disease?," *Neurobiology of Aging*, 23:1001-1008 (2002).
Sigurdsson et al., "Anti-priori antibodies for prophylaxis following prion exposure in mice," *Neurosciences Letters*, 336:185-187 (2003).
Sigurdsson et al., "Immunization Delays the Onset of Prion Disease in Mice," *American Journal of Pathology*, 161:13-17 (2002).
Sigurdsson, et al., "In vivo reversal of amyloid-beta lesions in rat brain," *J Neuropathol Exp Neurol.*, 59(1):11-17 (2000).
Sigurdsson et al., "Immunization with a Nontoxic/Nonfibrillar Amyloid-β Homologous Peptide Reduces Alzheimer's Disease-Associated Pathology in Trasngenic Mice," *Am. J. Pathology*, 159(2):439-447 (2001).
Sigurdsson et al., "Immunization with a nontoxic/nonfibrillar amyloid-β homologous peptide reduces Alzheimer's disease-associated pathology in transgenic mice," *Am. J. Pathol.*, 159(2):439-447 (2001).
Simmons, L., "Secondary structure of amyloid β peptide correlates with neurotoxic activity in vitro," *Molecular Pharmacology*, 45:373-379 (1994).
Singh, K. S., "Neuroautoimmunity: Pathogenic Implications for Alzheimer's Disease," *Gerontology*, 43:79-94 (1997).
Singh, V. K., "Studies of neuroimmune markers in Alzheimer's disease," *Mol. Neurobiology*, 9(1-3):73-81 (1994), abstract only.
Sinha, et al., "Recent advances in the understanding of the processing of APP to beta amyloid peptide," *Ann N Y Acad Sci.*, 920:206-8 (2000).
Sipe, "Amyloidosis," *Annu. Rev. Biochem.*, 61:947-975 (1992).
Skolnick and Fetrow, "From genes to protein structure and function: novel applications of computational approaches in the genomic era," *Trends in Biotech*, 18(1):34-39 (2000).
Small et al., "Alzheimer's disease and Abeta toxicity: from top to bottom," *Nat Rev Neurosci.*, 2(8):595-598 (2001).
Smith et al., "The challenges of genome sequence annotation of 'The devil is in the details,'" *Nature Biotechnology*, 15:1222-1223 (1997).
Smits et al., "Prion Protein and Scrapie Susceptibility," *Vet. Quart.*, 19(3):101-105 (1997).
Solomon and et al., "Modulation of The Catalytic Pathway of Carboxypeptidase A by Conjugation with Polyvinyl Alcohols," *Adv. Mol. Cell Biology*, 15A:33-45 (1996).
Solomon et al., "Activity of monoclonal antibodies in prevention of in vitro aggregation of their antigens," abstract from Department of Molecular Microbiology and Biotechnology, Tel Aviv University, Tel Aviv, Israel (publication date unknown).
Solomon et al., "Disaggregation of Alzheimer β-amyloid by site-directed mAb," *PNAS*, 94:4109-4112 (1997).
Solomon et al., "Monoclonal antibodies inhibit in vitro fibrillar aggregation of the Alzheimer β-amyloid peptide," *PNAS*, 93:452-455 (1996).
Solomon et al., "The Amino Terminus of the β-Amyloid Peptide Contains an Essential Epitope for Maintaining Its Solubility," from *Progress in Alzheimer's and Parkinson's Diseases*, edited by Fisher et al., Plenum Press, New York, pp. 205-211 (1995).
Solomon, A., "Pro-Rx (Protein Therapeutics)," University of Tennessee Medical Center (publication date unknown).
Solomon, B., "New Approach Towards Fast Induction of Anti β-Amyloid Peptide Immune Response," Department of Molecular Microbiology & Biotechnology, Tel-Aviv University, Ramat Aviv, Tel-Aviv, Israel (publication date unknown).
Solomon, B., "Immunological approaches as therapy for Alzheimer's disease," *Expert Opin. Biol. Ther.*, 2(8):907-917 (2002).
Solomon, B., "Generation and brain delivery of anti-aggregating antibodies against β-amyloid plaques using phage display technology," *J. Neural Transm. Suppl.*, 62:321-325 (2002).
Solomon, B., "Immunotherapeutic strategies for prevention and treatment of Alzheimer's disease," *DNA and Cell Biology*, 20(11):697-703 (2001).
Soto et al., "Beta sheet breaker peptides inhibit fibrillogenesis in a rat brain model of amyloidosis: implications for Alzheimer's therapy," *Nature Medicine*, 4(7):822-826 (1998).
Soto et al., "The α-helical to β-strand transition in the amino-terminal fragment of the amyloid β-peptide modulates amyloid formation," *J. Biol. Chem.*, 270(7):3063-3067 (1995).
Southwick et al., "Assessment of Amyloid β protein in Cerebrospinal fluid as an Aid in the Diagnosis of Alzheimer's Disease," *J. Neurochemistry*, 66:259-265 (1996).
Spooner et al., "The generation and characterization of potentially therapeutic Aβ antibodies in mice: differences according to strain and immunization protocol," *Vaccine*, 21:290-297 (2002).
St. George-Hyslop et al., "Antibody clears senile plaques," *Nature*, 40:116-117 (1999).
Stein et al., "Lack of Neurodegeneration in Transgenic Mice Overexpressing Mutant Amyloid Precursor Protein is Associated with Increased Levels of Transthyretin and Activation of Cell Survival Pathways," *The Journal of Neuroscience*, 22(17):7380-7388 (2002).
Stern et al., "Antibodies to the β-amyloid peptide cross-react with conformational epitopes in human fibrinogen subunits from peripheral blood," *FEBS Letters*, 264(1):43-47 (1990).
Stoute et al., "A Preliminary Evaluation of a Recombinant Circumsporozoite Protein Vaccine Against *Plasmodium Falciparum* malaria", *N. Engl. J. Med.*, 336(2):86-91 (1997).
Strbak et al., "Passive Immunization and Hypothalamic Peptide Secretion", *Neuroendocrinology*, 58:210-217 (1993).
Sturchler-Pierrat et al., "Two amyloid precursor protein transgenic mouse models with Alzheimer disease-like pathology," *PNAS*, 94: 13287-13292 (1997).
Su et al., "Intravascular infusions of soluble β-amyloid compromise the blood-brain barrier, activate CNS Glial cells and induce peripheral hemorrhage," *Brain Research*, 818:105-107 (1999).
Suo et al., "Soluble Alzheimers β-amyloid constricts the cerebral vasculature in vivo" *Neuroscience Letters*, 257:77-80 (1998).
Szendrei, et al., "The effects of aspartic acid-bond isomerization on in vitro properties of the amyloid β-peptide as modeled with N-terminal decapeptide fragments," *Int. J. Peptide Protein Res.*, 47:289-296 (1996).
Tabaton et al., "Soluble amyloid β-protein is a marker of Alzheimer amyloid in brain but not in cerebrospinal fluid," *Biochem. and Biophys. Res. Comm.*, 200(3):1598-1603 (1994).
Tal et al., "Complete Freund's Adjuvant Immunization Prolongs Survival in Experimental Prion Disease in Mice," *Journal of Neuroscience Research*, 71:286-290 (2003).
Tan et al., "Amyloidosis," *Histopatholog*, 25:403-414 (1994).
Tanaka et al., "NC-1900, an active fragment analog of arginine vasopressin, improves learning and memory deficits induced by beta-amyloid protein in rats," *European J. Pharmacology*, 352:135-142 (1998).
Teller et al., "Presence of soluble amyloid β-peptide precedes amyloid plaque formation in Down's syndrome" *Nature Medicine*, 2(1):93-95 (1996).
Tennent et al., "Serum amyloid P component prevents proteolysis of the amyloid fibrils of Alzheimer's disease and systemic amyloidosis," *PNAS*, 92:4299-4303 (1995).
Thorsett, E.D. et al., "Therapeutic approaches to Alzheimer's disease," *Curr. Op. in Chem. Biology*, 4:377-382 (2000).
Tjernberg et al., "A molecular model for Alzheimer amyloid β-peptide fibril formation," *J. Biol. Chem.*, 274(18):12619-12625 (1999).
Tjernberg et al., "Arrest of β-amyloid fibril formation by a pentapeptide ligand," *J. Biol. Chem.*, 271:8545-8548 (1996).
Tjernberg, et al, "Controlling amyloid beta-peptide fibril formation with protease-stable ligands," *J. Biol Chem.*, 272(19):12601-12605 (1997).

Town et al., "Characterization of murine immunoglobulin G antibodies against human amyloid-$\beta_{1-42}$" *Neurosci. Lett.* 307:101-104 (2001).

Trieb et al., "Is Alzheimer beta amyloid precursor protein (APP) an autoantigen? Peptides corresponding to parts of the APP sequence stimulate T lymphocytes in normals, but not in patients with Alzheimer's disease," *Immunobiology*, 191(2-3):114-115 Abstract C.37, (1994).

Tsuzuki et al., "Amyloid β protein in rat soleus in choroquine-induced myopthy using end-specific antibodies for Aβ40 and Aβ42: immunohistochemical evidence for amyloid β protein," *Neuroscience Letters*, 2002:77-80 (1995).

Van Gool et al., "Concentrations of amyloid-β protein in cerebrospinal fluid increase with age in patients free from neurodegenerative disease," *Neuroscience Letters*, 172:122-124 (1994).

Van Regenmortel et al, "D-peptides as immunogens and diagnostic reagents," *Curr. Opin. Biotechnol.*, 9(4):377-382 (1998).

Vehmas et al., "beta-Amyloid peptide vaccination results in marked changes in serum and brain Abeta levels in APPswe/PS1 DeltaE9 mice, as detected by SELDI-TOF-based ProteinChip® technology," *DNA Cell Biol.*, (11):713-721 (2001).

Velazquez et al., "Aspartate residue 7 in amyloid β-protein is critical for classical complement pathway activation: Implications for Alzheimer's disease pathogenesis," *Nature Medicine*, 3(1):77-79 (1997).

Verbeek et al., "Accumulation of Intercellular Adhesion Molecule-1 in Senile Plaques in Brain Tissue of patients with Alzheimer's Disease," *Amer. Journ. Pathology*, 144(1):104-116 (1994).

Verma et al., "Gene therapy—promises, problems and prospects," *Nature*, 389:239-242 (1997).

Vershigora A. E. *Obshchaya Immynologiya*, pp. 35, 229-231 and 152-153.

Walker et al., "Labeling of Cerebral Amyloid In Vivo with a Monoclonal Antibody," *J. Neuropath. Exp. Neurology*, 53(4):377-383 (1994).

Walsh et al., "Naturally secreted oligomers of amyloid β protein potently inhibit hippocampal long-term potentiation in vivo," *Nature*, 416(6880):535-539 (2002).

Wang et al., "The levels of soluble versus insoluble brain Aβ distinguish Alzheimer's disease from normal and pathologic aging," *Experimental Neurology*, 158:328-337 (1999).

Wang et al., "Soluble oligomers of β amyloid (1-42) inhibit long-term potentiation but not long-term depression in rate dentate gyrus," *Brain Research*, 924:133-140 (2002).

Washington University in St. Louis School of Medicine, "Study gives Clues to Working of Anti-Alzheimer Antibody," downloaded from www.medicine.wustl.edu/~wumpa/news on Dec. 15, 2004.

Weiner et al., "Nasal administration of amyloid-β peptide decreases cerebral amyloid burden in a mouse model of Alzheimer's disease," *Annals of Neurology*, 48:567-579 (2000).

Weiner et al., "Oral Tolerance: Immunologic Mechanisms and Treatment of Animal and Human Organ-Specific Autoimmune Diseases by Oral Administration of Autoantigens," *Annu. Rev. Immunol.*, 12:809-837 (1994).

Weissmann et al., "Bovine spongiform encephalopathy and early onset varian Creutzfeldt-Jakob disease," *Curr. Opin. Neurobiol.*, 7:695-700 (1997).

Weldon et al., "Neurotoxicity of Aβ Peptide: Confocal Imaging of Cellular Changes Induced by—Amyloid in Rat CNS In Vivo," *Society for Neuroscience Abstracts*, 22(Part 1) (1996).

Wells, J. A., "Additivity of Mutational Effects in Proteins," *Biochemistry*, 29(37):8509-8517 (1990).

Wen, G.Y., "Alzheimer's Disease and Risk Factors," *J. Food Drug Analysis*, 6(2):465-476 (1998).

Wengenack et al., "Targeting Alzheimer amyloid plaques in vivo," *Nature Biotech.*, 18:868-872 (2000).

White et al., "Immunotherapy as a therapeutic treatment for neurodegenerative disorders," *J. Neurochem.*, 87(4):801-808 (2003).

Winter et al., "Humanized antibodies" *Immunology Today*, 14(6):243-246 (1996).

Wisconsin Alumni Research Foundation, "Injection of Newborn Mice with Seven Chemical Adjuvants to Help Determine Their Safety in Use in Biologicals", U.S. Govt. Res. Develop. Rep., 70(24), 56. (Publication date unknown).

Wisniewski et al., "Alzheimer's disease and soluble A beta," *Neurobiol. Aging*, 15(2):143-52 (1994).

Wisniewski et al., "Therapeutics in Alzheimer's and Prion Diseases," *Biochemical Society Transactions*, 30(4):574-587 (2002).

Wong et al., "Neuritic Plaques and Cerebrovascular Amyloid in Alzheimer Disease are Antigenically Related," *PNAS*, 82:8729-8732 (1985).

Wood et al., "Amyloid precursor protein processing and Aβ42 deposition in a transgenic mouse model of Alzheimer disease," *PNAS*, 94: 1550-1555 (1997).

Wood et al., "Prolines and amyloidogenicity in fragments of the Alzheimer's peptide β/A4" *Biochemistry*, 34:724-730 (1995).

Wu, et al., "Drug targeting of a peptide radiopharmaceutical through the primate blood-brain barrier in vivo with a monoclonal antibody to the human insulin receptor," *J. Clin. Invest.*, 100:1804-1812 (1997).

Wu et al., "An Analysis of the Sequences of the Variable Regions of Bence Jones Proteins and Myeloma Light Chains and their Implications for Antibody Complementarity*," *J. Exp. Med.*, 132:211-250 (1970).

Xu et al., "Increased incidence of anti-βamyloid autoantibodies secreted by Epstein-Barr virus transformed B cell lines from patients with Alzheimer's disease," *Mechanisms of Ageing and Development*, 94:213-222 (1997).

Yamaguchi et al., Diffuse plaques associated with astroglial amyloid β protein, possibly showing a disappearing stage of senile plaques, *Acta Neuropathol.*, 95:217-222 (1998).

Yang et al., "Effects of Racemization on the Aggregational Properties of the Amyloid β-Peptide in Alzheimer'Disease," abstract # 255 from American Chemical Society 214th National Meeting (1997).

Younkin, "Amyloid β vaccination: reduced plaques and improved cognition," *Nature Medicine*, 7:18-19 (2001).

Zlokovic et al., "Clearance of amyloid β-peptide from brain: transport or metabolism?," *Nature Medicine*, 6(7):718-719 (2000).

Zlokovic et al., "Glycoprotein 330/megalin: probable role in receptor-mediated transport of apolipoprotein J alone and in a complex with Alzheimer disease amyloid beta at the blood-brain and blood-cerebrospinal fluid barriers," *PNAS*, 93(9):4229-4334 (1996) abstract only.

U.S. Appl. No. 11/245,524, filed Oct. 7, 2005, Schenk.
U.S. Appl. No. 11/245,916, filed Oct. 7, 2005, Schenk.
U.S. Appl. No. 60/067,740, filed Dec. 2, 1997, Schenk.
U.S. Appl. No. 60/067,219, filed Dec. 3, 1997, Weiner et al.
U.S. Appl. No. 60/079,697, filed Mar. 27, 1998, Weiner et al.
U.S. Appl. No. 60/080,970, filed Jan. 11, 1999, Schenk.

Alberts et al., eds. *Molecular Biology of The Cell, Third Edition*, chapter 23, pp. 1208-1209 (1994).

Alberts et al., *Molecular Biology of the Cell, 2nd Edition*, pp. 266-267, Garland Publishing Inc., New York (1989).

Amit et al., "Three-Dimensional Structure of an Antigen-Antibody Complex at 2.8 Å Resolution," *Science*, 233:747-753 (1986).

Ankarcrona et al., "Biomarkers for apoptosis in Alzheimer's disease," *Int. J. Geriatric Psychiatry*, 20:101-105 (2005).

Auld et al., "Alzheimer's disease and the basal forebrain cholinergic system: relations to β-amyloid peptides, cognition, and treatment strategies," *Progress in Neurobiol.*, 68:209-245 (2002).

Bales et al., "Administration of an Anti-Aβ Fab Fragment to $APP^{V717F}$ Transgenic Mice Reduces Neuritic Plaque," Abstract P$-396, p. S587, presented at Poster Session P4: Therapeutics and Therapeutic Strategies-Therapeutic Strategies, Amyloid-Based.

Bickel et al., "Development and in Vitro Characterization of a Cationized Monoclonal Antibody against βA4 Protein: A Potential Probe for Alzheimer's Disease," *Bioconjugate Chem.*, 5:119-125 (1994).

Blasberg et al., "Regional Localization of Glioma-assoicated Antigen Defined by Monoclonal Antibody 81C6 in Vivo: Kinetics and Implications for Diagnosis and Therapy," *Cancer Research*, 47:4432-4443 (1987).

Brazil et al., "Effects of Incorporation of Immunoglobulin G and Complement Component C1q on Uptake and Degradation of Alzheimer's Disease Amyloid Fibrils by Microglia," *J. Biol. Chem.*, 275(22):16941-16947 (2000).

Broadwell et al., "Serum proteins bypass the blood-brain fluid barriers for extracellular entry to the central nervous system," *Exp. Neurol.*, 120(2):245-263 (1993).

Brookmeyer et al., "Projections of Alzheimer's Disease in the United States and the Public Health Impact of Delaying Disease Onset," *Am. J. Public Health*, 88:1337-1342 (1998).

Bussiere et al., "Morphological Characterization of Thioflavin-S-Positive Amyloid Plaques in Transgenic Alzheimer Mice and Effect of Passive Aβ Immunotherapy on Their Clearance," *Am. J. Pathology*, 165(3):987-995 (2004).

Cassell et al., "Demography and Epidemiology of Age-Associated Neuronal Impairment," chapter 4, pp. 31-50 from *Funcitional Neurobiology of Aging*, Hof et al., eds., Academic Press (2001).

Chimicon International, "Mouse Anti-Amyloid Beta Protein Monoclonal Antibody," Catalog # MAB1561.

Clayton et al., "Synucleins in Synaptic Plasticity and Neurodegenerative Disorders," *J. Neurosci. Res.*, 58:120-129 (1999).

Coico et al., *Immunology A Short Course, Fifth Edition*, pp. 18-24 (2003).

Cox et al., "Adjuvants—a classification and review of their modes of action," *Vaccine*, 15(3):248-256 (1997).

Davis, S. S., "Nasal Vaccines," *Advanced Drug Delivery Reviews*, 51:21-42 (2001).

De Lustig et al., "Peripheral Markers and Diagnostic Criteria in Alzheimer's Disease: Critical Evaluations," *Rev. In Neurosciences*, 5:213-225 (1994).

DeWitt et al., "Astrocytes regulate microglial phagocytosis of senile plaque cores of Alzheimer's disease," *Experimental Neurology*, 149:329-340 (1998).

Dictionary.com definition of "prophylactic", pp. 1-3 downloaded from internet Oct. 12, 2005.

Di Martino et al., "Production and Characterization of Antibodies to Mouse Scrapie-Amyloid Protein Elicited by Non-carrier Linked Synthetic Peptide Immunogens," *J. Molecular Recognition*, 4(2-3):85-91 (1991).

Du et al., "$\alpha_2$-Macroglobulin as a β-Amyloid Peptide-Binding Plasma Protein," *J. Neurochemistry*, 69(1):299-305 (1997).

European Search Report of May 22, 2006 for European Application 06075704.4-2107.

European Search REport of May 22, 2006 for European Application 06075479.3-2107.

Foote et al., "Antibody Framework Residues Affecting the Conformation of the Hypervariable Loops," *J. Mol. Biol.*, 224:487-499 (1992).

Fox et al., "Presymptomatic cognitive deficits in individuals at risk of familial Alzheimer's disease," *Brain*, 121:1631-1639 (1998).

Fukutani et al., "Cerebeller pathology in sporadic and familial Alzheimer's disease including APP 717 (Val->lle) mutation cases: A morphometric investigation," *J. Neurologic Sci.*, 149:177-184 (1997).

Genbank Accession No. AAD26773, "Immunoglobulin heavy chain VH3609-JH3 region [*Mus musculus*]," Apr. 22, 1999.

Gupta et al., "Adjuvants for human vaccines—current status, problems, and future prospects," *Vaccine*, 13(14):1263-1275 (1995).

Hara et al., "Development of a safe oral Aβ vaccine using recombinant adeno-associated virus vector for Alzheimer's disease," *J. Alzheimer's Disease*, 6:483-488 (2004).

Harlow et al., eds., *Antibodies: A Laboratory Manual*, pp. 71-82 (1998).

Hirschfield et al., "Amylodiosis: new strategies for treatment," *Int. J. Biochem. & Cell Biol.*, 35:1608-1613 (2003).

Ida et al., "Analysis of Heterogeneous βA4 Peptides in Juman Cerebrospinal Fluid and Blood by a Newly Developed Sensitive Western Blot Assay," *J. Biol. Chem.*, 271(37):22908-22914 (1996).

Jung et al., "Alzheimer's Beta-amyloid Precursor Protein is Expressed on the Surface of Immediately Ex Vivo Brain Cells: a Flow Cytometric Study," *J. Neurosci. Res.*, 46(3):336-348 (1996).

Kajkowski et al., "β-Amyloid Peptide-induced Apoptosis Regulated by a Novel Protein Containing a G Protein Activation Module," *J. Biol. Chem.*, 276(22):18748-18756 (2001).

Kascsak et al., "Mouse Polyclonal and Monoclonal Antibody to Scrapie-Associated Fibril Proteins," *J. Virology*, 61(12):3688-3693 (1987).

Kofler et al., "Immunoglobulin $_k$ Light Chain Variable Region Gene Complex Organization and Immunoglobulin Genes Encoding Anti-DNA Autoantibodies in Lupus Mice," *J. Clin. Invest.*, 82:852-860 (1988).

Kuby, J., eds., p. 123 from *Immunology, Third Edition*, W.H. Freeman & co., (1997).

Kuo et al., "Water-soluble Aβ (N-40, N-42) Oligomers in Normal and Alzheimer Disease Brains," *J. Biol. Chem.*, 271(8):4077-4081 (1996).

Kurashima et al., "Production of Monoclonal Antibody against Amyloid Fibril Protein and Its Immunohistochemical Application," *Appl. Pathol.*, 3(1-2):39-54 (1985).

LaDu et al., "Isoform-specific Binding of Apolipoprotein E to β-Amyloid," *J. Biol. Chem.*, 269(38):23403-23406 (1994).

Landolfi et al., "The Integrity of the Ball-and Socket Joint Between V and C Domains Is Essential for Complete Activity of a Humanized Antibody," *J. Immunology*, 166(3):1748-1754 (2001).

Lavie et al., "EFRH-Phage Immunization of Alzheimer's Disease Animal Model Improves Behavioral Performance in Morris Water Maze Trials," *J. Molecular Neuroscience*, 24:105-113 (2004).

Licastro et al., "Is immunotherapy an effective treatment for Alzheimer's disease?," *Immunity & Aging*, 1:1-2 (2004).

Linke, "Monoclonal antibodies against amyloid fibril protein AA. Production, specificity, and use for immunohistochemical localization and classification of AA-type amyloidosis," *J. Histochemistry and Cytochemistry*, 32(3):322-328 (1982).

Lo et al., "High level expression and secretion of Fc-X fusion proteins in mammalian cells," *Protein Engineering*, 11 (6):495-500 (1998).

Mandel et al., "Clinical trials in neurological disorders using AAV vectors: promises and challenges," *Curr. Opin. Mol. Ther.*, 6(5):482-490 (2004).

Manoj et al., "Approaches to Enhance the Efficacy of DNA Vaccines," *Critical Rev. Clin. Lab. Sci.*, 41(1):1-39 (2004).

Marhaug et al., "Monoclonal hybridoma antibodies to human amyloid related protein SAA," *Clin. Exp. Immunol.*, 50(2):390-396 (1982).

Marotta et al., "Overexpression of amyloid precursor protein A4 (β-amyloid) immunoreactivity in genetically transformed cells: Implications for a cellular model of Alzheimer amyloidosis," *PNAS*, 86:337-341 (1989).

Maury et al., "Immunohistochemical Localization of Amyloid in Finnish Hereditary Amyloidosis with Antibodies to Gelsolin Peptides," *Laboratory Investigation*, 64(3):400-404 (1991).

Merriam-Webster online medical dictionary, entry for "cure", accessed Sep. 5, 2006.

Okura et al., "Nonviral Aβ DNA vaccine therapy against Alzheimer's disease: Long-term effect and safety," *PNAS*, 103(25):9619-9624 (2006).

Orlandi et al., "Cloning immunoglobulin variable domains for expression by the polymerase chain reaction," *PNAS*, 86:3833-3837 (1989).

Panka et al., "Variable region framework differences result in decreased or increased affinity of variant anti-digoxin antibodies," *PNAS*, 85:3080-3084 (1998).

Parnetti et al., "Cognitive Enhancement Therapy for Alzheimer's Disease, The Way Forward," *Drugs*, 53(5):752-768 (1997).

PCT Search Report of Aug. 11, 2006 for application PCT/US2006/002837.

Peeters et al., "Comparison of four bifunctional reagents for coupling peptides to proteins and the effect of the three moieties on the immunogenicity of the conjugates," *J. Immunological Methods*, 120:133-143 (1989).

Phelps et al., "Development and Characterization of Monoclonal Antibodies Specific for Amylin," *Hybridoma*, 15(5):379-386 (1996).

Probert et al., "Spontaneous inflammatory demyelinating disease in transgenic mice showing central nervous system-specific expression of tunmor necrosis factor α," *PNAS*, 92:11294-11298 (1995).

Qu et al., "Aβ$_{42}$ gene vaccination reduces brain amyloid plaque burden in transgenic mice," *J. Neurological Sciences*, 244:151-158 (2006).

Racke et al., "Exacerbation of Cerebral Amyloid Angiopathy-Assoiciated Microhemorrhage in Amyloid Precursor Protein Trasngenic Mice by Immunotherapy Is Dependent on Antibody Recognition of Deposited Forms of amyloid β," *J. Neurosci.*, 25(3):629-636 (2005).

Research Corporation Technology News, "THP and SangStat Partner to Develop Humanized Polyclonal Antibody Drugs," Nov. 11, 2002.

Schenk et al., "Current progress in beta-myeloid immunotherapy," *Curr. Opin. Immunology*, 16(5):599-606 (2004).

Schmitt et al., "Interactions of the alzheimer β amyloid fragement$_{(25-35)}$ with peripheral blood dendritic cells," *Mechanisms of Ageing and Development*, 94:223-232 (1997).

Shinkai et al., "Amyloid β-Proteins 1-40 and 1-42(43) in the Soluble Fraction of Extra- and Intracranial Blood Vessels," *Ann. Neurol.*, 38:421-428 (1995).

Signet Laboratories, Inc., Product data sheet for mouse monoclonal clone 6E10, revised Jul. 13, 2005.

Small et al., "Cerebral metabolic and cognitive decline in persons at genetic risk for Alzheimer's disease," *PNAS*, 97(11):6037-6042 (2000).

Souder et al., "Overview of Alzheimer's disease," *Nurs. Clin. N. Am.*, 39:545-559 (2004).

Trieb et al., "APP Peptides Stimulate Lymphocyte Proliferation in Normals, But Not in Patients With Alzheimer's Disease," *Neurobiology of Aging*, 17(4):541-547 (1996).

Urmoneit et al., "Cerebrovascular Smooth Muscle CElls Internalize Alzheimer Amyloid Beta Protein via a Lipoprotein Pathway: Implications for Cerebral Amyloid Angiopathy," *Laboratory Investigation*, 77(2):157-166 (1997).

Valleix et al., "Hereditary renal amyloidosis caused by a new variant lysozyme W64R in a French family," *Kidney International*, 61:907-912 (2002).

Van Den Dobbelsteen et al., "Characteristics of Immune Responses to Native and Protein Conjugated Pneumococcal Polysaccharide Type 14," *Scand. J. Immunol.*, 41:273-280 (1995).

Vickers, J. C., "A Vaccine Against Alzheimer's Disease," *Drugs Aging*, 19(7):487-494 (2002).

Vidanovic et al., "Effects of nonionic surfactants on the physical stability of immunoglobulin G in aqueous solution during mechanical agitation," *Die Pharmazie*, 58(6):399-404 (2003).

Wang, W., "Instability, stabilization, and formulation of liquid protein pharmaceuticals," *Int. J. Pharmaceutics*, 185(2):129-188 (1999).

*Webster's New World Dictionary*, p. 1387, therapeutic (1988).

*Webster's New World Dictionary of American English*, Third College Edition, p. 1078 (1988).

Weiner, H. L., "Oral tolerance: immune mechanisms and treatment of autoimmune diseases," *Immunology Today*, 18:335-343 (1997).

Weinreb et al., "NACP, A Protein Implicated in Alzheimer's Disease and Learning, Is Natively Unfolded," *Biochemistry*, 35(43):13709-13715 (1996).

Wikipedia definition of "epitope" printed from internet on Apr. 26, 2006.

Wikipedia definition of "antigen" printed from internet on Apr. 26, 2006.

Wikipedia definition of "route of administration including parenteral" printed from internet on Apr. 26, 2006.

Yamada et al., "Generation and Characterization of Rat Monoclonal Antibodies Against Human Serum Amyloid A," *Scand. J. Immunol.*, 46(2):175-179 (1997).

Zameer et al., "Single Chain Fv Antibodies against 25-35 Peptide Fragment of Amyloid-β: Potential Therapeutic for Alzheimer's Disease," Abstract P4-420, p. S593, presented at Poster Session P4:Therapeutics and Therpeutic Strategies-Therapeutic Strateies, Amyloid-Based.

Zhang et al., "Specialized Applications, Purification of Recombinant Proteins and Study of Protein Interaction by Epitope Tagging," *Current Protocols in Mol. Biol.*, Supp 41, pp. 10.15.1 through 10.15.9 (1998).

Zhang et al., "A novel recombinant adeno-associated virus vaccine reduces behavioral impairment and β-amyloid plaques in a mouse model of Alzheimer's disease," *Neurobiology of Disease*, 14:365-379 (2003).

\* cited by examiner

FIG. 3A

| | | | | | | | | | | | | | | | | | | | |
|---|---|---|---|---|---|---|---|---|---|---|---|---|---|---|---|---|---|---|---|
| | M | K | L | P | V | R | L | L | - | V | L | M | F | W | I | P | A | S | S |
| ch12B4VL | ATG | AAG | TTG | CCT | GTT | AGG | CTG | TTG | --- | GTG | CTG | ATG | TTC | TGG | ATT | CCT | GCT | TCC | AGC | S |
| | M | R | L | P | A | Q | L | L | G | L | L | M | L | W | V | S | G | S | S |
| 12B4VLv1 | ATG | AGG | CTC | CCT | GCT | CAG | CTC | CTG | GGG | CTG | CTA | ATG | CTC | TGG | GTC | TCT | GGA | TCC | AGT | GGG |
| x63397 VL germline | --- | --- | --- | --- | --- | --- | --- | --- | --- | --- | --- | --- | --- | --- | --- | --- | --- | --- | --- | --- |
| | M | R | L | P | A | Q | L | L | G | L | L | M | L | W | V | S | G | S | S |
| x67904 K005036 VL | ATG | AGG | CTC | CCT | GCT | CAG | CTC | CTG | GGG | CTA | ATG | CTC | TGG | GTC | TCT | GGA | TCC | AGT | GGG |

| | D | V | L | M | T | Q | T | P | L | S | L | P | V | S | L | G | D | Q | A | S |
|---|---|---|---|---|---|---|---|---|---|---|---|---|---|---|---|---|---|---|---|---|
| ch12B4VL | GAT | GTT | TTG | ATG | ACC | CAA | ACT | CCA | CTC | TCC | CTG | CCT | GTC | AGT | CTT | GGA | GAT | CAA | GCC | TCC |
| | D | V | V | M | T | Q | T | P | L | S | L | P | V | T | P | G | E | P | A | S |
| 12B4VLv1 | GAT | GTT | GTG | ATG | ACT | CAG | TCT | CCA | CTC | TCC | CTG | CCC | GTC | ACC | CCT | GGA | GAG | CCG | GCC | TCC |
| | D | I | V | M | T | Q | T | P | L | S | L | P | V | T | P | G | E | P | A | S |
| x63397 VL germline | GAT | ATT | GTG | ATG | ACT | CAG | TCT | CCA | CTC | TCC | CTG | CCC | GTC | ACC | CCT | GGA | GAG | CCG | GCC | TCC |
| | D | I | V | M | T | Q | T | P | L | S | L | P | V | T | P | G | E | P | A | S |
| x67904 K005036 VL | GAT | ATT | GTG | ATG | ACT | CAG | TCT | CCA | CTC | TCC | CTG | CCC | GTC | ACC | CCT | GGA | GAG | CCG | GCC | TCC |

|  | | | | | | | | | | | | | | |
|---|---|---|---|---|---|---|---|---|---|---|---|---|---|---|
| ch12B4VL | S | G | V | P | D | R | F | S | G | S | G | S | G | T | D | F | T | L | K | I | 80 |
| 12B4VLv1 | TCT | GGG | GTC | CCA | GAC | AGG | TTC | AGT | GGC | AGT | GGA | TCA | GGG | ACA | GAT | TTC | ACA | CTC | AAG | ATC | 217 |
| x63397 VL germline | S | G | V | P | D | R | F | S | G | S | G | S | G | T | D | F | T | L | K | I | 80 |
| x67904 K005036 VL | TCT | GGG | GTC | CCT | GAC | AGG | TTC | AGT | GGC | AGT | GGA | TCA | GGG | ACA | GGC | GAT | TTT | ACA | CTG | AAA | ATC | 300 |

(alignment continues - sequences for ch12B4VL, 12B4VLv1, x63397 VL germline, x67904 K005036 VL shown across positions 250–280)

|  | | | | | | | | | | | | | | |
|---|---|---|---|---|---|---|---|---|---|---|---|---|---|---|
| ch12B4VL | S | R | V | E | A | E | D | L | G | V | Y | Y | C | F | Q | G | S | H | V | P | 100 |
| 12B4VLv1 | AGC | AGA | GTG | GAG | GCT | GAG | GAT | CTG | GGA | GTT | TAT | TAC | TGC | TTT | CAA | GGT | TCA | CAT | GTT | CCG | 357 |
| x63397 VL germline | S | R | V | E | A | E | D | V | G | V | Y | Y | C | M | Q | A | L | Q | T | P | 100 |
| x67904 K005036 VL | AGC | AGA | GTG | GAG | GCT | GAG | GAT | GTT | GGG | GTT | TAT | TAC | TGC | ATG | CAA | GCT | CTA | CAA | ACT | CCT | 360 |

FIG. 3D

```
                         370
         L   T   F   G   A   G   T   K   L   E   L   K
ch12B4VL CTC ACG TTC GGT GCT GGG ACC AAG CTG GAG CTG AAA
         L   T   F   G   Q   G   T   K   L   E   I   K
12B4VLv1 CTC ACG TTC GGT CAG GGG ACC AAG CTG GAG ATC AAA
```

112  112
                                    393  396 x63397 VL germline x67904 K005036 VL

Decoration: Box residues that match 12B4VLv1.cons exactly.

[Figure 4B: Nucleotide and amino acid sequence alignment of ch12B4VH, 12B4VHv1, X54437 KAB000333 VH, and BAA75026 VH4-61 germline, showing positions 150–250 of the variable heavy chain region.]

FIG. 4C

| | | | | | | | | | | | | | | | | | | | | | | |
|---|---|---|---|---|---|---|---|---|---|---|---|---|---|---|---|---|---|---|---|---|---|---|
| ch12B4VH | N | P | S | L | K | S | R | L | T | I | S | K | D | T | S | N | N | Q | V | F | | 81 |
| | AAC | CCA | TCC | CTG | AAG | AGC | CGG | CTC | ACA | ATC | TCC | AAG | GAT | ACC | TCT | AAC | AAT | CAG | GTA | TTC | | 300 |
| 12B4VHv1 | N | P | S | L | K | S | R | L | T | I | S | K | D | T | S | K | N | Q | V | S | | 81 |
| | AAC | CCA | TCC | CTC | AAG | AGT | CGA | CTC | ACA | ATC | TCA | AAG | GAC | ACG | TCC | AAG | AAC | CAG | GTA | TCC | | 300 |
| X54437 KAB000333 VH | N | P | S | L | K | S | R | V | T | I | S | V | D | T | S | K | N | Q | F | S | | 279 |
| | AAC | CCG | TCC | CTC | AAG | AGT | CGA | GTC | ACC | ATA | TCT | GTA | GAC | ACG | TCC | AAG | AAC | CAG | TTC | TCC | | |
| BAA75026 VH4-61germline | N | P | S | L | K | S | R | V | T | I | S | V | D | T | S | K | N | Q | F | S | | 81 |
| | AAC | CCC | TCC | CTC | AAG | AGT | CGA | GTC | ACC | ATA | TCA | GTA | GAC | ACG | TCC | AAG | AAC | CAG | TTC | TCC | | 300 |

| | | | | | | | | | | | | | | | | | | | | | | |
|---|---|---|---|---|---|---|---|---|---|---|---|---|---|---|---|---|---|---|---|---|---|---|
| ch12B4VH | L | K | I | T | N | V | D | T | A | T | Y | Y | C | A | R | R | R | | | | | 101 |
| | CTC | AAG | ATC | ACC | AAT | GTG | GAC | ACT | GCT | ACA | TAC | TAC | TGT | GCT | CGA | AGG | AGG | | | | | 360 |
| 12B4VHv1 | L | K | L | S | S | V | T | A | A | D | T | A | V | Y | Y | C | A | R | R | R | | 101 |
| | CTG | AAG | CTG | AGC | TCT | GTG | ACC | GCC | GCA | GAC | ACG | GCC | GTG | TAT | TAC | TGT | GCG | AGA | AGG | AGG | | 360 |
| X54437 KAB000333 VH | L | K | L | S | S | V | T | A | A | D | T | A | V | Y | Y | C | A | R | L | G | | 101 |
| | CTG | AAG | CTG | AGC | TCT | GTG | ACC | GCT | GCA | GAC | ACG | GCC | GTG | TAT | TAC | TGT | GCG | AGA | CTC | GGC | | 337 |
| BAA75026 VH4-61germline | L | K | L | S | S | V | T | A | A | D | T | A | V | Y | Y | C | A | R | | | | 99 |
| | CTG | AAG | CTG | AGC | TCT | GTG | ACC | GCT | GCG | GAC | ACG | GCC | GTG | TAT | TAC | TGT | GCG | AGA | | | | 354 |

Decoration: Box residues that match 12B4VHv1.cons exactly.

Aβ42 ELISA

Aβ42 ELISA

Ex vivo on PDAPP brain sections
1-42 ELISA

*Ex vivo* on AD brain sections
(12yrs+ duration of disease)
1-42 ELISA

*Ex vivo* on AD brain sections
(12yrs+ duration of disease)
X-42 ELISA

Strategy for PCR-mediated assembly of humanized VL.v1

Strategy for PCR-mediated assembly of humanized VH.v1

HUMANIZED ANTIBODIES THAT RECOGNIZE BETA AMYLOID PEPTIDE

RELATED APPLICATIONS

This application claims the benefit of prior-filed provisional patent application U.S. Ser. No. 60/363,751 (filed Mar. 12, 2002) entitled "Humanized Antibodies That Recognize Beta-Amyloid Peptide" (pending). The entire content of the above-referenced application is incorporated herein by reference.

BACKGROUND OF THE INVENTION

Alzheimer's disease (AD) is a progressive disease resulting in senile dementia. See generally Selkoe, *TINS* 16:403 (1993); Hardy et al., WO 92/13069; Selkoe, *J. Neuropathol. Exp. Neurol.* 53:438 (1994); Duff et al., *Nature* 373:476 (1995); Games et al., *Nature* 373:523 (1995). Broadly speaking, the disease falls into two categories: late onset, which occurs in old age (65+ years) and early onset, which develops well before the senile period, i.e., between 35 and 60 years. In both types of disease, the pathology is the same but the abnormalities tend to be more severe and widespread in cases beginning at an earlier age. The disease is characterized by at least two types of lesions in the brain, neurofibrillary tangles and senile plaques. Neurofibrillary tangles are intracellular deposits of microtubule associated tau protein consisting of two filaments twisted about each other in pairs. Senile plaques (i.e., amyloid plaques) are areas of disorganized neuropil up to 150 μm across with extracellular amyloid deposits at the center which are visible by microscopic analysis of sections of brain tissue. The accumulation of amyloid plaques within the brain is also associated with Down's syndrome and other cognitive disorders.

The principal constituent of the plaques is a peptide termed Aβ or β-amyloid peptide. Aβ peptide is a 4-kDa internal fragment of 39–43 amino acids of a larger transmembrane glycoprotein named protein termed amyloid precursor protein (APP). As a result of proteolytic processing of APP by different secretase enzymes, Aβ is primarily found in both a short form, 40 amino acids in length, and a long form, ranging from 42–43 amino acids in length. Part of the hydrophobic transmembrane domain of APP is found at the carboxy end of Aβ, and may account for the ability of Aβ to aggregate into plaques, particularly in the case of the long form. Accumulation of amyloid plaques in the brain eventually leads to neuronal cell death. The physical symptoms associated with this type of neural deterioration characterize Alzheimer's disease.

Several mutations within the APP protein have been correlated with the presence of Alzheimer's disease. See, e.g., Goate et al., *Nature* 349:704) (1991) (valine$^{717}$ to isoleucine); Chartier Harlan et al. *Nature* 353:844 (1991)) (valine$^{717}$ to glycine); Murrell et al., *Science* 254:97 (1991) (valine$^{717}$ to phenylalanine); Mullan et al., *Nature Genet.* 1:345 (1992) (a double mutation changing lysine$^{595}$-methionine$^{596}$ to asparagine$^{595}$-leucine$^{596}$). Such mutations are thought to cause Alzheimer's disease by increased or altered processing of APP to Aβ, particularly processing of APP to increased amounts of the long form of Aβ (i.e., Aβ1–42 and Aβ1–43). Mutations in other genes, such as the presenilin genes, PS1 and PS2, are thought indirectly to affect processing of APP to generate increased amounts of long form Aβ (see Hardy, *TINS* 20: 154 (1997)).

Mouse models have been used successfully to determine the significance of amyloid plaques in Alzheimer's (Games et al., supra, Johnson-Wood et al., *Proc. Natl. Acad. Sci. USA* 94:1550 (1997)). In particular, when PDAPP transgenic mice, (which express a mutant form of human APP and develop Alzheimer's disease at a young age), are injected with the long form of Aβ, they display both a decrease in the progression of Alzheimer's and an increase in antibody titers to the Aβ peptide (Schenk et al., *Nature* 400, 173 (1999)). The observations discussed above indicate that Aβ, particularly in its long form, is a causative element in Alzheimer's disease.

Accordingly, there exists the need for new therapies and reagents for the treatment of Alzheimer's disease, in particular, therapies and reagents capable of effecting a therapeutic benefit at physiologic (e.g., non-toxic) doses.

SUMMARY OF THE INVENTION

The present invention features new immunological reagents, in particular, therapeutic antibody reagents for the prevention and treatment of amyloidogenic disease (e.g., Alzheimer's disease). The invention is based, at least in part, on the identification and characterization of a monoclonal antibody that specifically binds to Aβ peptide and is effective at reducing plaque burden and/or reducing the neuritic dystrophy associated with amyloidogenic disorders. Structural and functional analysis of this antibody leads to the design of various humanized antibodies for prophylactic and/or therapeutic use. In particular, the invention features humanization of the variable regions of this antibody and, accordingly, provides for humanized immunoglobulin or antibody chains, intact humanized immunoglobulins or antibodies, and functional immunoglobulin or antibody fragments, in particular, antigen binding fragments, of the featured antibody.

Polypeptides comprising the complementarity determining regions of the featured monoclonal antibody are also disclosed, as are polynucleotide reagents, vectors and host cells suitable for encoding said polypeptides.

Methods of treatment of amyloidogenic diseases or disorders (e.g., Alzheimer's disease) are disclosed, as are pharmaceutical compositions and kits for use in such applications.

Also featured are methods of identifying residues within the featured monoclonal antibodies which are important for proper immunologic function and for identifying residues which are amenable to substitution in the design of humanized antibodies having improved binding affinities and/or reduced immunogenicity, when used as therapeutic reagents.

Also featured are antibodies (e.g., humanized antibodies) having altered effector functions, and therapeutic uses thereof.

BRIEF DESCRIPTION OF THE DRAWINGS

Figure 3B:
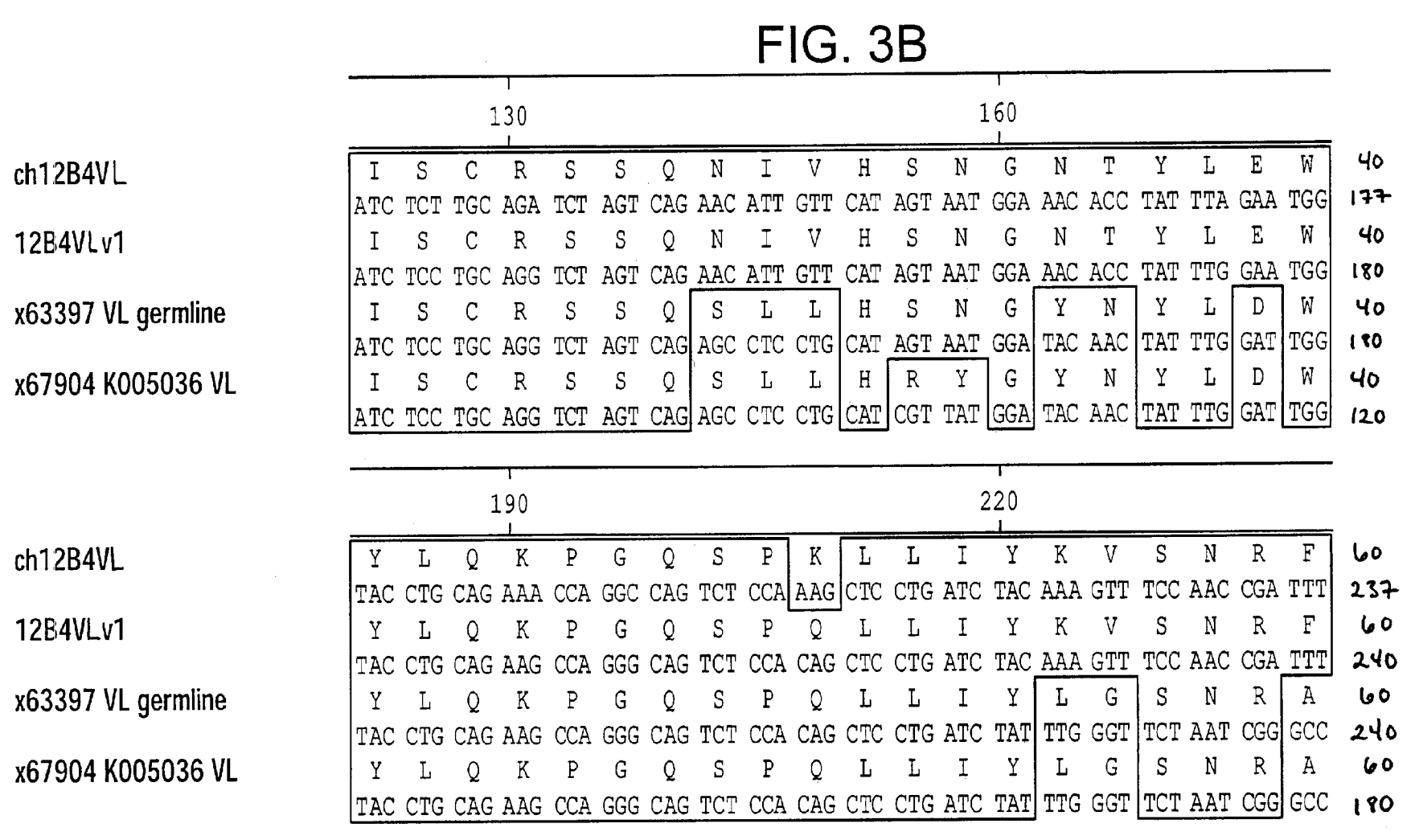

FIGS. 3A–D depicts the nucleotide and amino acid sequence for humanized 12B4VLv1 compared with chimeric 12B4VL (identical variable region sequences as murine 12B4VL, SEQ ID NOs: 1 and 2, respectively); germline A19 sequences (SEQ ID NOs: 29 and 30, respectively); and Kabid ID 005036 (SEQ ID NOs: 31 and 32, respectively).

Figure 4A:
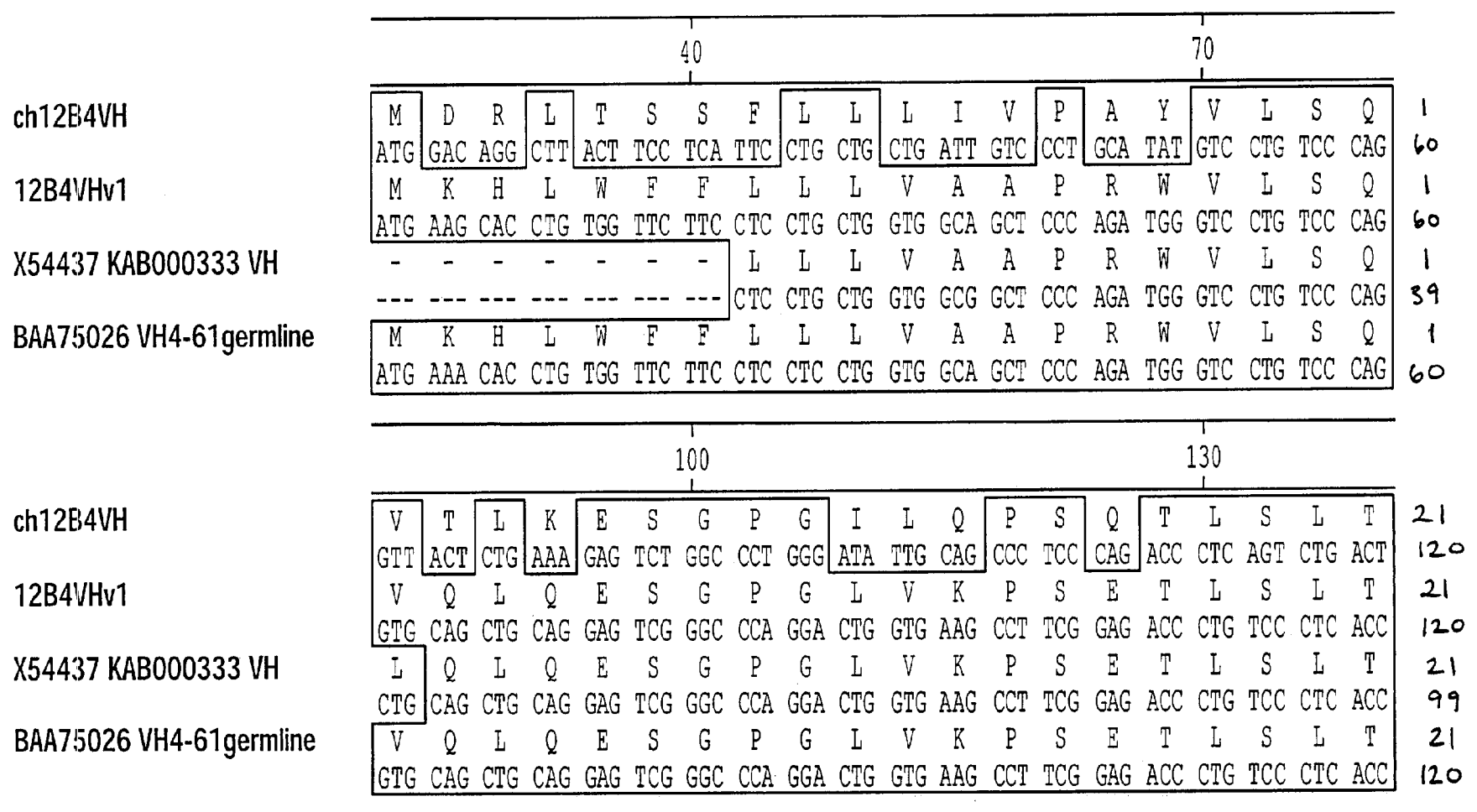

FIGS. 4A–D depicts the nucleotide and amino acid sequence for humanized 12B4VHv1 compared with chimeric 12B4VH (identical variable region sequences as murine 12B4VH, SEQ ID NOs: 3 and 4, respectively); Kabat ID 000333 (SEQ ID NOs: 33 and 34, respectively); and germline VH4–61 (SEQ ID NOs: 35 and 36, respectively).

FIG. 9 is a schematic representation of the PCR-mediated assembly of humanized 12B4, version 1.

DETAILED DESCRIPTION OF THE INVENTION

Figure 1A:
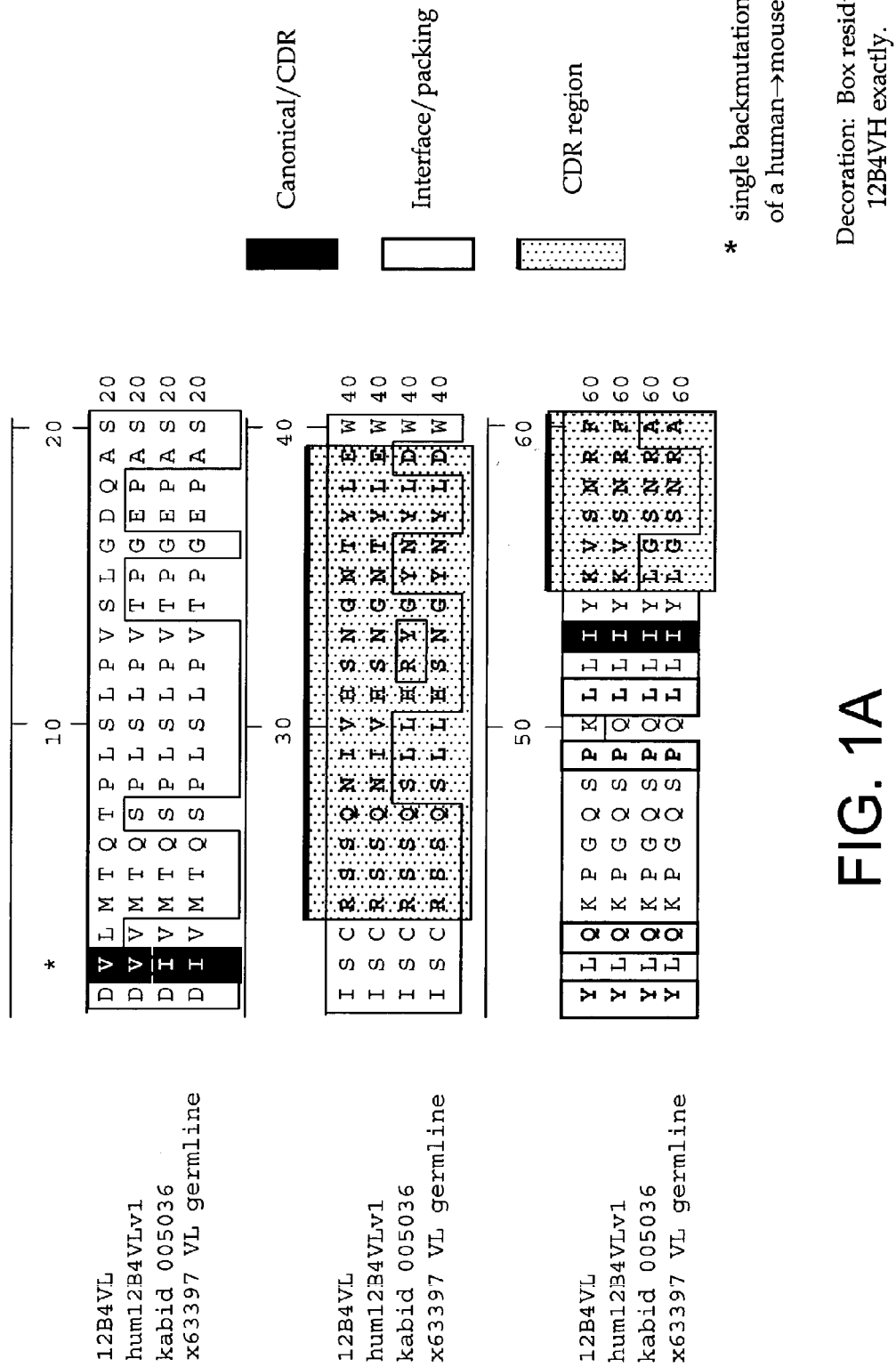
FIGS. 1A–B depicts an alignment of the amino acid sequences of the light chain of mouse 12B4 (mature peptide, SEQ ID NO:2), humanized 12B4 (mature peptide, SEQ ID NO:6), Kabat ID 005036 (mature peptide, SEQ ID NO:32) and germline A19 (X63397, mature peptide, SEQ ID NO:30) antibodies. CDR regions are stippled and overlined. The single backmutation of a human→mouse residue is indicated by the asterisk. The importance of the shaded residues is shown in the legend. Numbered from the first methionine, not Kabat numbering.

The present invention features new immunological reagents and methods for preventing or treating Alzheimer's disease or other amyloidogenic diseases. The invention is based, at least in part, on the characterization of a monoclonal immunoglobulin, 12B4, effective at binding beta amyloid protein (Aβ) (e.g., binding soluble and/or aggregated Aβ), mediating phagocytosis (e.g., of aggregated Aβ), reducing plaque burden and/or reducing neuritic dystrophy (e.g., in a patient). The invention is further based on the determination and structural characterization of the primary and secondary structure of the variable light and heavy chains of the 12B4 immunoglobulin and the identification of residues important for activity and immunogenicity.

Immunoglobulins are featured which include a variable light and/or variable heavy chain of the 12B4 monoclonal immunoglobulin described herein. Preferred immunoglobulins, e.g., therapeutic immunoglobulins, are featured which include a humanized variable light and/or humanized variable heavy chain. Preferred variable light and/or variable heavy chains include a complementarity determining region (CDR) from the 12B4 immunoglobulin (e.g., donor immunoglobulin) and variable framework regions substantially from a human acceptor immunoglobulin. The phrase "substantially from a human acceptor immunoglobulin" means that the majority or key framework residues are from the human acceptor sequence, allowing however, for substitution of residues at certain positions with residues selected to improve activity of the humanized immunoglobulin (e.g., alter activity such that it more closely mimics the activity of the donor immunoglobulin) or selected to decrease the immunogenicity of the humanized immunoglobulin.

In one embodiment, the invention features a humanized immunoglobulin light or heavy chain that includes 12B4 variable region complementarity determining regions (CDRs) (i.e., includes one, two or three CDRs from the light chain variable region sequence set forth as SEQ ID NO:2 or includes one, two or three CDRs from the heavy chain variable region sequence set forth as SEQ ID NO:4), and includes a variable framework region substantially from a human acceptor immunoglobulin light or heavy chain sequence, provided that at least one residue of the framework residue is backmutated to a corresponding murine residue, wherein said backmutation does not substantially affect the ability of the chain to direct Aβ binding.

In another embodiment, the invention features a humanized immunoglobulin light or heavy chain that includes 12B4 variable region complementarity determining regions (CDRs) (e.g., includes one, two or three CDRs from the light chain variable region sequence set forth as SEQ ID NO:2 and/or includes one, two or three CDRs from the heavy chain variable region sequence set forth as SEQ ID NO:4), and includes a variable framework region substantially from a human acceptor immunoglobulin light or heavy chain sequence, provided that at least one framework residue is substituted with the corresponding amino acid residue from the mouse 12B4 light or heavy chain variable region sequence, where the framework residue is selected from the group consisting of (a) a residue that non-covalently binds antigen directly; (b) a residue adjacent to a CDR; (c) a CDR-interacting residue (e.g., identified by modeling the light or heavy chain on the solved structure of a homologous known immunoglobulin chain); and (d) a residue participating in the VL–VH interface.

In another embodiment, the invention features a humanized immunoglobulin light or heavy chain that includes 12B4 variable region CDRs and variable framework regions from a human acceptor immunoglobulin light or heavy chain sequence, provided that at least one framework residue is substituted with the corresponding amino acid residue from the mouse 12B4 light or heavy chain variable region sequence, where the framework residue is a residue capable of affecting light chain variable region conformation or function as identified by analysis of a three-dimensional model of the variable region, for example a residue capable of interacting with antigen, a residue proximal to the antigen binding site, a residue capable of interacting with a CDR, a residue adjacent to a CDR, a residue within 6 Å of a CDR residue, a canonical residue, a vernier zone residue, an interchain packing residue, an unusual residue, or a glycosylation site residue on the surface of the structural model.

In another embodiment, the invention features, in addition to the substitutions described above, a substitution of at least one rare human framework residue. For example, a rare residue can be substituted with an amino acid residue which is common for human variable chain sequences at that position. Alternatively, a rare residue can be substituted with a corresponding amino acid residue from a homologous germline variable chain sequence.

In another embodiment, the invention features a humanized immunoglobulin that includes a light chain and a heavy chain, as described above, or an antigen-binding fragment of said immunoglobulin. In an exemplary embodiment, the humanized immunoglobulin binds (e.g., specifically binds) to beta amyloid peptide (Aβ) with a binding affinity of at least $10^7$ $M^{-1}$, $10^8$ $M^{-1}$, or $10^9$ $M^{-1}$. In another embodiment, the immunoglobulin or antigen binding fragment includes a heavy chain having isotype γ1. In another embodiment, the immunoglobulin or antigen binding fragment binds (e.g., specifically binds) to both soluble beta amyloid peptide (Aβ) and aggregated Aβ. In another embodiment, the immunoglobulin or antigen binding fragment mediates phagocytosis (e.g., induces phagocytosis) of beta amyloid peptide (Aβ). In yet another embodiment, the immunoglobulin or antigen binding fragment crosses the blood-brain barrier in a subject. In yet another embodiment, the immunoglobulin or antigen binding fragment reduces both beta amyloid peptide (Aβ) burden and neuritic dystrophy in a subject.

In another embodiment, the invention features chimeric immunoglobulins that include 12B4 variable regions (e.g., the variable region sequences set forth as SEQ ID NO:2 or SEQ ID NO:4). In yet another embodiment, the immunoglobulin, or antigen-binding fragment thereof, further includes constant regions from IgG1.

The immunoglobulins described herein are particularly suited for use in therapeutic methods aimed at preventing or treating amyloidogenic diseases. In one embodiment, the invention features a method of preventing or treating an amyloidogenic disease (e.g., Alzheimer's disease) that involves administering to the patient an effective dosage of a humanized immunoglobulin as described herein. In another embodiment, the invention features pharmaceutical compositions that include a humanized immunoglobulin as described herein and a pharmaceutical carrier. Also featured are isolated nucleic acid molecules, vectors and host cells for producing the immunoglobulins or immunoglobulin fragments or chains described herein, as well as methods for producing said immunoglobulins, immunoglobulin fragments or immunoglobulin chains The present invention further features a method for identifying 12B4 residues amenable to substitution when producing a humanized 12B4 immunoglobulin, respectively. For example, a method for identifying variable framework region residues amenable to substitution involves modeling the three-dimensional structure of a 12B4 variable region on a solved homologous immunoglobulin structure and analyzing said model for residues capable of affecting 12B4 immunoglobulin variable region conformation or function, such that residues amenable to substitution are identified. The invention further features use of the variable region sequence set forth as SEQ ID NO:2 or SEQ ID NO:4, or any portion thereof, in producing a three-dimensional image of a 12B4 immunoglobulin, 12B4 immunoglobulin chain, or domain thereof.

The present invention further features immunoglobulins having altered effector function, such as the ability to bind effector molecules, for example, complement or a receptor on an effector cell. In particular, the immunoglobulin of the invention has an altered constant region, e.g., Fc region, wherein at least one amino acid residue in the Fe region has been replaced with a different residue or side chain. In one embodiment, the modified immunoglobulin is of the IgG class, comprises at least one amino acid residue replacement in the Fe region such that the immunoglobulin has an altered effector function, e.g., as compared with an unmodified immunoglobulin. In particular embodiments, the immunoglobulin of the invention has an altered effector function such that it is less immunogenic (e.g., does not provoke undesired effector cell activity, lysis, or complement binding), has improved amyloid clearance properties, and/or has a desirable half-life.

Prior to describing the invention, it may be helpful to an understanding thereof to set forth definitions of certain terms to be used hereinafter.

The term "immunoglobulin" or "antibody" (used interchangeably herein) refers to a protein having a basic four-polypeptide chain structure consisting of two heavy and two light chains, said chains being stabilized, for example, by interchain disulfide bonds, which has the ability to specifically bind antigen. The term "single-chain immunoglobulin" or "single-chain antibody" (used interchangeably herein) refers to a protein having a two-polypeptide chain structure consisting of a heavy and a light chain, said chains being stabilized, for example, by interchain peptide linkers, which has the ability to specifically bind antigen. The term "domain" refers to a globular region of a heavy or light chain polypeptide comprising peptide loops (e.g., comprising 3 to 4 peptide loops) stabilized, for example, by β-pleated sheet and/or intrachain disulfide bond. Domains are further referred to herein as "constant" or "variable", based on the relative lack of sequence variation within the domains of various class members in the case of a "constant" domain, or the significant variation within the domains of various class members in the case of a "variable" domain. Antibody or polypeptide "domains" are often referred to interchangeably in the art as antibody or polypeptide "regions". The "constant" domains of an antibody light chain are referred to interchangeably as "light chain constant regions", "light chain constant domains", "CL" regions or "CL" domains. The "constant" domains of an antibody heavy chain are referred to interchangeably as "heavy chain constant regions", "heavy chain constant domains", "CH" regions or "CH" domains). The "variable" domains of an antibody light chain are referred to interchangeably as "light chain variable regions", "light chain variable domains", "VL" regions or "VL" domains). The "variable" domains of an antibody heavy chain are referred to interchangeably as "heavy chain constant regions", "heavy chain constant domains", "CH" regions or "CH" domains).

The term "region" can also refer to a part or portion of an antibody chain or antibody chain domain (e.g., a part or portion of a heavy or light chain or a part or portion of a constant or variable domain, as defined herein), as well as more discrete parts or portions of said chains or domains. For example, light and heavy chains or light and heavy chain variable domains include "complementarity determining regions" or "CDRs" interspersed among "framework regions" or "FRs", as defined herein.

Immunoglobulins or antibodies can exist in monomeric or polymeric form, for example, IgM antibodies which exist in pentameric form and/or IgA antibodies which exist in monomeric, dimeric or multimeric form. The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. Exemplary fragments include Fab, Fab', F(ab')2, Fabc and/or Fv fragments. The term "antigen-binding fragment" refers to a polypeptide fragment of an immunoglobulin or antibody that binds antigen or competes with intact antibody (i.e., with the intact antibody from which they were derived) for antigen binding (i e., specific binding).

The term "conformation" refers to the tertiary structure of a protein or polypeptide (e.g., an antibody, antibody chain, domain or region thereof). For example, the phrase "light (or heavy) chain conformation" refers to the tertiary structure of a light (or heavy) chain variable region, and the phrase "antibody conformation" or "antibody fragment conformation" refers to the tertiary structure of an antibody or fragment thereof.

"Specific binding" of an antibody mean that the antibody exhibits appreciable affinity for antigen or a preferred epitope and, preferably, does not exhibit significant cross-reactivity. "Appreciable" or preferred binding include binding with an affinity of at least $10^6$, $10^7$, $10^8$, $10^9$ M$^{-1}$, or $10^{10}$ M$^{-1}$. Affinities greater than $10^7$ M$^{-1}$, preferably greater than $10^8$ M$^{-1}$ are more preferred. Values intermediate of those set forth herein are also intended to be within the scope of the present invention and a preferred binding affinity can be indicated as a range of affinities, for example, $10^6$ to $10^{10}$ M$^{-1}$, preferably $10^7$ to $10^{10}$ M$^{-1}$, more preferably $10^8$ to $10^{10}$ M$^{-1}$. An antibody that "does not exhibit significant cross-reactivity" is one that will not appreciably bind to an undesirable entity (e.g., an undesirable proteinaceous entity). For example, an antibody that specifically binds to Aβ will appreciably bind Aβ but will not significantly react with non-Aβ proteins or peptides (e.g., non-Aβ proteins or peptides included in plaques). An antibody specific for a preferred epitope will, for example, not significantly cross-react with remote epitopes on the same protein or peptide. Specific binding can be determined according to any art-recognized means for determining such binding. Preferably, specific binding is determined according to Scatchard analysis and/or competitive binding assays.

Binding fragments are produced by recombinant DNA techniques, or by enzymatic or chemical cleavage of intact immunoglobulins. Binding fragments include Fab, Fab', F(ab')$_2$, Fabc, Fv, single chains, and single-chain antibodies. Other than "bispecific" or "bifunctional" immunoglobulins or antibodies, an immunoglobulin or antibody is understood to have each of its binding sites identical. A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.* 79:315–321 (1990); Kostelny et al., *J. Immunol.* 148, 1547–1553 (1992).

The term "humanized immunoglobulin" or "humanized antibody" refers to an immunoglobulin or antibody that includes at least one humanized immunoglobulin or antibody chain (i.e., at least one humanized light or heavy chain). The term "humanized immunoglobulin chain" or "humanized antibody chain" (i.e., a "humanized immunoglobulin light chain" or "humanized immunoglobulin heavy chain") refers to an immunoglobulin or antibody chain (i.e., a light or heavy chain, respectively) having a variable region that includes a variable framework region substantially from a human immunoglobulin or antibody and complementarity determining regions (CDRs) (e.g., at least one CDR, preferably two CDRs, more preferably three CDRs) substantially from a non-human immunoglobulin or antibody, and further includes constant regions (e.g., at least one constant region or portion thereof, in the case of a light chain, and preferably three constant regions in the case of a heavy chain). The term "humanized variable region" (e.g., "humanized light chain variable region" or "humanized heavy chain variable region") refers to a variable region that includes a variable framework region substantially from a human immunoglobulin or antibody and complementarity determining regions (CDRs) substantially from a non-human immunoglobulin or antibody.

The phrase "substantially from a human immunoglobulin or antibody" or "substantially human" means that, when aligned to a human immunoglobulin or antibody amino sequence for comparison purposes, the region shares at least 80–90%, preferably at least 90–95%, more preferably at least 95–99% identity (i.e., local sequence identity) with the human framework or constant region sequence, allowing, for example, for conservative substitutions, consensus sequence substitutions, germline substitutions, backmutations, and the like. The introduction of conservative substitutions, consensus sequence substitutions, germline substitutions, backmutations, and the like, is often referred to as "optimization" of a humanized antibody or chain. The phrase "substantially from a non-human immunoglobulin or antibody" or "substantially nonhuman" means having an immunoglobulin or antibody sequence at least 80–95%, preferably at least 90–95%, more preferably, 96%, 97%, 98%, or 99% identical to that of a non-human organism, e.g., a non-human mammal.

Accordingly, all regions or residues of a humanized immunoglobulin or antibody, or of a humanized immunoglobulin or antibody chain, except possibly the CDRs, are substantially identical to the corresponding regions or residues of one or more native human immunoglobulin sequences. The term "corresponding region" or "corresponding residue" refers to a region or residue on a second amino acid or nucleotide sequence which occupies the same (i.e., equivalent) position as a region or residue on a first amino acid or nucleotide sequence, when the first and second sequences are optimally aligned for comparison purposes.

The term "significant identity" means that two polypeptide sequences, when optimally aligned, such as by the programs GAP or BESTFIT using default gap weights, share at least 50–60% sequence identity, preferably at least 60–70% sequence identity, more preferably at least 70–80% sequence identity, more preferably at least 80–90% identity, even more preferably at least 90–95% identity, and even more preferably at least 95% sequence identity or more (e.g., 99% sequence identity or more). The term "substantial identity" means that two polypeptide sequences, when optimally aligned, such as by the programs GAP or BESTFIT using default gap weights, share at least 80–90% sequence identity, preferably at least 90–95% sequence identity, and more preferably at least 95% sequence identity or more (e.g., 99% sequence identity or more). For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Austibel et al., Current Protocols in Molecular Biology). One example of algorithm that is suitable for determining percent sequence identity and sequence similarity is the BLAST algorithm, which is described in Altschul et al., *J. Mol. Biol.* 215:403 (1990). Software for performing BLAST analyses is publicly available through the National Center for Biotechnology Information (publicly accessible through the National Institutes of Health NCBI internet server). Typically, default program parameters can be used to perform the sequence comparison, although customized parameters can also be used. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

Preferably, residue positions which are not identical differ by conservative amino acid substitutions. For purposes of classifying amino acids substitutions as conservative or nonconservative, amino acids are grouped as follows: Group I (hydrophobic sidechains): leu, met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Nonconservative substitutions constitute exchanging a member of one of these classes for a member of another.

Preferably, humanized immunoglobulins or antibodies bind antigen with an affinity that is within a factor of three, four, or five of that of the corresponding nonhumanized antibody. For example, if the nonhumanized antibody has a binding affinity of $10^9$ $M^{-1}$, humanized antibodies will have a binding affinity of at least $3 \times 10^9$ $M^{-1}$, $4 \times 10^9$ $M^{-1}$ or $10^9$ $M^{-1}$. When describing the binding properties of an immunoglobulin or antibody chain, the chain can be described based on its ability to "direct antigen (e.g., Aβ) binding". A chain is said to "direct antigen binding" when it confers upon an intact immunoglobulin or antibody (or antigen binding fragment thereof) a specific binding property or binding affinity. A mutation (e.g., a backmutation) is said to substantially affect the ability of a heavy or light chain to direct antigen binding if it affects (e.g., decreases) the binding affinity of an intact immunoglobulin or antibody (or antigen binding fragment thereof) comprising said chain by at least an order of magnitude compared to that of the antibody (or antigen binding fragment thereof) comprising an equivalent chain lacking said mutation. A mutation "does not substantially affect (e.g., decrease) the ability of a chain to direct antigen binding" if it affects (e.g., decreases) the binding affinity of an intact immunoglobulin or antibody (or antigen binding fragment thereof) comprising said chain by only a factor of two, three, or four of that of the antibody (or antigen binding fragment thereof) comprising an equivalent chain lacking said mutation.

The term "chimeric immunoglobulin" or antibody refers to an immunoglobulin or antibody whose variable regions derive from a first species and whose constant regions derive from a second species. Chimeric immunoglobulins or antibodies can be constructed, for example by genetic engineering, from immunoglobulin gene segments belonging to different species. The terms "humanized immunoglobulin" or "humanized antibody" are not intended to encompass chimeric immunoglobulins or antibodies, as defined infra. Although humanized immunoglobulins or antibodies are chimeric in their construction (i.e., comprise regions from more than one species of protein), they include additional features (i.e., variable regions comprising donor CDR residues and acceptor framework residues) not found in chimeric immunoglobulins or antibodies, as defined herein.

An "antigen" is an entity (e.g., a proteinaceous entity or peptide) to which an antibody specifically binds.

The term "epitope" or "antigenic determinant" refers to a site on an antigen to which an immunoglobulin or antibody (or antigen binding fragment thereof) specifically binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods of determining spatial conformation of epitopes include, for example, x-ray crystallography and 2-dimensional nuclear magnetic resonance. See, e.g., *Epitope Mapping Protocols in Methods in Molecular Biology*, Vol. 66, G. E. Morris, Ed. (1996).

Antibodies that recognize the same epitope can be identified in a simple immunoassay showing the ability of one antibody to block the binding of another antibody to a target antigen, i.e., a competitive binding assay. Competitive binding is determined in an assay in which the immunoglobulin under test inhibits specific binding of a reference antibody to a common antigen, such as Aβ. Numerous types of competitive binding assays are known, for example: solid phase direct or indirect radioimmunoassay (RIA), solid phase direct or indirect enzyme immunoassay (EIA), sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labeled assay, solid phase direct labeled sandwich assay (see Harlow and Lane, Antibodies: *A Laboratory Manual*, Cold Spring Harbor Press (1988)); solid phase direct label RIA using I-125 label (see Morel et al., *Mol. Immunol.* 25(1):7 (1988)); solid phase direct biotin-avidin EIA (Cheung et al., *Virology* 176:546 (1990)); and direct labeled RIA. (Moldenhauer et al., *Scand. J. Immunol.* 32:77 (1990)). Typically, such an assay involves the use of purified antigen bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50–55%, 55–60%, 60–65%, 65–70% 70–75% or more.

An epitope is also recognized by immunologic cells, for example, B cells and/or T cells. Cellular recognition of an epitope can be determined by in vitro assays that measure antigen-dependent proliferation, as determined by $^3$H-thymidine incorporation, by cytokine secretion, by antibody secretion, or by antigen-dependent killing (cytotoxic T lymphocyte assay).

Exemplary epitopes or antigenic determinants can be found within the human amyloid precursor protein (APP), but are preferably found within the Aβ peptide of APP.

Multiple isoforms of APP exist, for example APP$^{695}$ APP$^{751}$ and APP$^{770}$. Amino acids within APP are assigned numbers according to the sequence of the APP$^{770}$ isoform (see e.g., GenBank Accession No. P05067). Aβ (also referred to herein as beta amyloid peptide and A-beta) peptide is an approximately 4-kDa internal fragment of 39–43 amino acids of APP (Aβ39, Aβ40, Aβ41, Aβ42 and Aβ43). Aβ40, for example, consists of residues 672–711 of APP and Aβ42 consists of residues 673–713 of APP. As a result of proteolytic processing of APP by different secretase enzymes iv vivo or in situ, Aβ is found in both a "short form", 40 amino acids in length, and a "long form", ranging from 42–43 amino acids in length. Preferred epitopes or antigenic determinants, as described herein, are located within the N-terminus of the Aβ peptide and include residues within amino acids 1–10 of Aβ, preferably from residues 1–3, 1–4, 1–5, 1–6, 1–7 or 3–7 of Aβ42. Additional referred epitopes or antigenic determinants include residues 2–4, 5, 6, 7 or 8 of Aβ, residues 3–5, 6, 7, 8 or 9 of Aβ, or residues 4–7, 8, 9 or 10 Aβ42. When an antibody is said to bind to an epitope within specified residues, such as Aβ 3–7, what is meant is that the antibody specifically binds to a polypeptide containing the specified residues (i.e., Aβ 3–7 in this an example). Such an antibody does not necessarily contact every residue within Aβ 3–7. Nor does every single amino acid substitution or deletion with in Aβ 3–7 necessarily significantly affect binding affinity.

The term "amyloidogenic disease" includes any disease associated with (or caused by) the formation or deposition of insoluble amyloid fibrils. Exemplary amyloidogenic diseases include, but are not limited to systemic amyloidosis, Alzheimer's disease, mature onset diabetes, Parkinson's disease, Huntington's disease, fronto-temporal dementia, and the prion-related transmissible spongiform encephalopathies (kuru and Creutzfeldt-Jacob disease in humans and scrapie and BSE in sheep and cattle, respectively). Different amyloidogenic diseases are defined or characterized by the nature of the polypeptide component of the fibrils deposited. For example, in subjects or patients having Alzheimer's disease, β-amyloid protein (e.g., wild-type, variant, or truncated β-amyloid protein) is the characterizing polypeptide component of the amyloid deposit. Accordingly, Alzheimer's disease is an example of a "disease characterized by deposits of Aβ" or a "disease associated with deposits of Aβ", e.g., in the brain of a subject or patient. The terms "β-amyloid protein", "β-amyloid peptide", "β-amyloid", "Aβ" and "Aβ peptide" are used interchangeably herein.

An "immunogenic agent" or "immunogen" is capable of inducing an immunological response against itself on administration to a mammal, optionally in conjunction with an adjuvant.

The term "treatment" as used herein, is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease.

The term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. Amounts effective for this use will depend upon the severity of the infection and the general state of the patient's own immune system.

The term "patient" includes human and other mammalian subjects that receive either prophylactic or therapeutic treatment.

"Soluble" or "dissociated" Aβ refers to non-aggregating or disaggregated Aβ polypeptide, including monomeric soluble as well as oligomeric soluble Aβ polypeptide (e.g., soluble Aβ dimers, trimers, and the like). "Insoluble" Aβ refers to aggregating Aβ polypeptide, for example, Aβ held together by noncovalent bonds. Aβ (e.g., Aβ42) is believed to aggregate, at least in part, due to the presence of hydrophobic residues at the C-terminus of the peptide (part of the transmembrane domain of APP). Soluble Aβ can be found in vivo in biological fluids such as cerebrospinal fluid and/or serum. Alternatively, soluble Aβ can be prepared by dissolving lyophilized peptide in neat DMSO with sonication. The resulting solution is centrifuged (e.g., at 14,000× g, 4° C., 10 minutes) to remove any insoluble particulates.

The term "effector function" refers to an activity that resides in the Fc region of an antibody (e.g., an IgG antibody) and includes, for example, the ability of the antibody to bind effector molecules such as complement and/or Fc receptors, which can control several immune functions of the antibody such as effector cell activity, lysis, complement-mediated activity, antibody clearance, and antibody half-life.

The term "effector molecule" refers to a molecule that is capable of binding to the Fc region of an antibody (e.g., an IgG antibody) including, but not limited to, a complement protein or a Fc receptor.

The term "effector cell" refers to a cell capable of binding to the Fc portion of an antibody (e.g., an IgG antibody) typically via an Fc receptor expressed on the surface of the effector cell including, but not limited to, lymphocytes, e.g., antigen presenting cells and T cells.

The term "Fc region" refers to a C-terminal region of an IgG antibody, in particular, the C-terminal region of the heavy chain(s) of said IgG antibody. Although the boundaries of the Fc region of an IgG heavy chain can vary slightly, a Fc region is typically defined as spanning from about amino acid residue Cys226 to the carboxyl-terminus of an IGg heavy chain(s).

The term "Kabat numbering" unless otherwise stated, is defined as the numbering of the residues in, e.g., an IgG heavy chain antibody using the EU index as in Kabat et al. (Sequences of Proteins of Immunological Interest, 5th Ed. Public Health Service, National Institutes of Health, Bethesda, Md. (1991)), expressly incorporated herein by reference.

The term "Fc receptor" or "FcR" refers to a receptor that binds to the Fc region of an antibody. Typical Fc receptors which bind to an Fc region of an antibody (e.g., an IgG antibody) include, but are not limited to, receptors of the FcγRI, FcγRII, and FcγRIII subclasses, including allelic variants and alternatively spliced forms of these receptors. Fc receptors are reviewed in Ravetch and Kinet, Annu. Rev. Immunol 9:457–92 (1991); Capel et al., Immunomethods 4:25–34 (1994); and de Haas et al., J. Lab. Clin. Med. 126:330–41 (1995).

I. Immunological and Therapeutic Reagents

Immunological and therapeutic reagents of the invention comprise or consist of immunogens or antibodies, or functional or antigen binding fragments thereof, as defined herein. The basic antibody structural unit is known to comprise a tetramer of subunits. Each tetramer is composed of two identical pairs of polypeptide chains, each pair having one "light" (about 25 kDa) and one "heavy" chain (about 50–70 kDa). The amino-terminal portion of each chain includes a variable region of about 100 to 110 or more amino acids primarily responsible for antigen recognition. The carboxy-terminal portion of each chain defines a constant region primarily responsible for effector function.

Light chains are classified as either kappa or lambda and are about 230 residues in length. Heavy chains are classified as gamma (γ), mu (μ), alpha (α), delta (δ), or epsilon (ε), are about 450–600 residues in length, and define the antibody's isotype as IgG, IgM, IgA, IgD and IgE, respectively. Both heavy and light chains are folded into domains. The term "domain" refers to a globular region of a protein, for example, an immunoglobulin or antibody. Immunoglobulin or antibody domains include, for example, 3 or four peptide loops stabilized by β-pleated sheet and an interchain disulfide bond. Intact light chains have, for example, two domains ($V_L$ and $C_L$) and intact heavy chains have, for example, four or five domains ($V_H$, $C_H1$, $C_H2$, and $C_H3$).

Within light and heavy chains, the variable and constant regions are joined by a "J" region of about 12 or more amino acids, with the heavy chain also including a "D" region of about 10 more amino acids. (See generally, *Fundamental Immunology* (Paul, W., ed., 2nd ed. Raven Press, N.Y. (1989), Ch. 7, incorporated by reference in its entirety for all purposes).

The variable regions of each light/heavy chain pair form the antibody binding site. Thus, an intact antibody has two binding sites. Except in bifunctional or bispecific antibodies, the two binding sites are the same. The chains all exhibit the same general structure of relatively conserved framework regions (FR) joined by three hypervariable regions, also called complementarity determining regions or CDRs. Naturally-occurring chains or recombinantly produced chains can be expressed with a leader sequence which is removed during cellular processing to produce a mature chain. Mature chains can also be recombinantly produced having a non-naturally occurring leader sequence, for example, to enhance secretion or alter the processing of a particular chain of interest.

The CDRs of the two mature chains of each pair are aligned by the framework regions, enabling binding to a specific epitope. From N-terminal to C-terminal, both light and heavy chains comprise the domains FR1, CDR1, FR2, CDR2, FR3, CDR3 and FR4. "FR4" also is referred to in the art as the D/J region of the variable heavy chain and the J region of the variable light chain. The assignment of amino acids to each domain is in accordance with the definitions of Kabat, *Sequences of Proteins of Immunological Interest* (National Institutes of Health, Bethesda, Md., 1987 and 1991). An alternative structural definition has been proposed by Chothia et al., *J. Mol. Biol.* 196:901 (1987); *Nature* 342:878 (1989); and *J. Mol. Biol.* 186:651 (1989) (hereinafter collectively referred to as "Chothia et al." and incorporated by reference in their entirety for all purposes).

A. Aβ Antibodies

Therapeutic agents of the invention include antibodies that specifically bind to Aβ or to other components of the amyloid plaque. Preferred antibodies are monoclonal antibodies. Some such antibodies bind specifically to the aggregated form of Aβ without binding to the soluble form. Some bind specifically to the soluble form without binding to the aggregated form. Some bind to both aggregated and soluble forms. Antibodies used in therapeutic methods preferably have an intact constant region or at least sufficient of the constant region to interact with an Fc receptor. Preferred antibodies are those efficacious at stimulating Fc-mediated phagocytosis of Aβ in plaques. Human isotype IgG1 is preferred because of it having highest affinity of human isotypes for the FcRI receptor on phagocytic cells (e.g., on brain resident macrophages or microglial cells). Human IgG1 is the equivalent of murine IgG2a, the latter thus suitable for testing in vivo efficacy in animal (e.g., mouse) models of Alzheimer's. Bispecific Fab fragments can also be used, in which one arm of the antibody has specificity for Aβ, and the other for an Fc receptor. Preferred antibodies bind to Aβ with a binding affinity greater than (or equal to) about $10^6$, $10^7$, $10^8$, $10^9$, or $10^{10}$ $M^{-1}$ (including affinities intermediate of these values).

Monoclonal antibodies bind to a specific epitope within Aβ that can be a conformational or nonconformational epitope. Prophylactic and therapeutic efficacy of antibodies can be tested using the transgenic animal model procedures described in the Examples. Preferred monoclonal antibodies bind to an epitope within residues 1–10 of Aβ (with the first N terminal residue of natural Aβ designated 1), more preferably to an epitope within residues 3–7 of Aβ. In some methods, multiple monoclonal antibodies having binding specificities to different epitopes are used, for example, an antibody specific for an epitope within residues 3–7 of Aβ can be co-administered with an antibody specific for an epitope outside of residues 3–7 of Aβ. Such antibodies can be administered sequentially or simultaneously. Antibodies to amyloid components other than Aβ can also be used (e.g., administered or co-administered).

Epitope specificity of an antibody can be determined, for example, by forming a phage display library in which different members display different subsequences of Aβ. The phage display library is then selected for members specifically binding to an antibody under test. A family of sequences is isolated. Typically, such a family contains a common core sequence, and varying lengths of flanking sequences in different members. The shortest core sequence showing specific binding to the antibody defines the epitope bound by the antibody. Antibodies can also be tested for epitope specificity in a competition assay with an antibody whose epitope specificity has already been determined. For example, antibodies that compete with the 12B4 antibody for binding to Aβ bind to the same or similar epitope as 12B4, i.e., within residues Aβ 3–7. Screening antibodies for epitope specificity is a useful predictor of therapeutic efficacy. For example, an antibody determined to bind to an epitope within residues 1–7 of Aβ is likely to be effective in preventing and treating Alzheimer's disease according to the methodologies of the present invention.

Antibodies that specifically bind to a preferred segment of Aβ without binding to other regions of Aβ have a number of advantages relative to monoclonal antibodies binding to other regions or polyclonal sera to intact Aβ. First, for equal mass dosages, dosages of antibodies that specifically bind to preferred segments contain a higher molar dosage of antibodies effective in clearing amyloid plaques. Second, antibodies specifically binding to preferred segments can induce a clearing response against amyloid deposits without inducing a clearing response against intact APP polypeptide, thereby reducing the potential side effects.

1. Production of Nonhuman Antibodies

The present invention features non-human antibodies, for example, antibodies having specificity for the preferred Aβ epitopes of the invention. Such antibodies can be used in formulating various therapeutic compositions of the invention or, preferably, provide complementarity determining regions for the production of humanized or chimeric antibodies (described in detail below). The production of non-human monoclonal antibodies, e.g., murine, guinea pig, primate, rabbit or rat, can be accomplished by, for example, immunizing the animal with Aβ. A longer polypeptide comprising Aβ or an immunogenic fragment of Aβ or anti-idiotypic antibodies to an antibody to Aβ can also be used. See Harlow & Lane, supra, incorporated by reference for all purposes). Such an immunogen can be obtained from a natural source, by peptide synthesis or by recombinant expression. Optionally, the immunogen can be administered fused or otherwise complexed with a carrier protein, as described below. Optionally, the immunogen can be administered with an adjuvant. The term "adjuvant" refers to a compound that when administered in conjunction with an antigen augments the immune response to the antigen, but when administered alone does not generate an immune response to the antigen. Adjuvants can augment an immune response by several mechanisms including lymphocyte recruitment, stimulation of B and/or T cells, and stimulation of macrophages. Several types of adjuvant can be used as described below. Complete Freund's adjuvant followed by incomplete adjuvant is preferred for immunization of laboratory animals.

Rabbits or guinea pigs are typically used for making polyclonal antibodies. Exemplary preparation of polyclonal antibodies, e.g., for passive protection, can be performed as follows. 125 non-transgenic mice are immunized with 100 µg Aβ1–42, plus CFA/IFA adjuvant, and euthanized at 4–5 months. Blood is collected from immunized mice. IgG is separated from other blood components. Antibody specific for the immunogen may be partially purified by affinity chromatography. An average of about 0.5–1 mg of immunogen-specific antibody is obtained per mouse, giving a total of 60–120 mg.

Mice are typically used for making monoclonal antibodies. Monoclonals can be prepared against a fragment by injecting the fragment or longer form of Aβ into a mouse, preparing hybridomas and screening the hybridomas for an antibody that specifically binds to Aβ. Optionally, antibodies are screened for binding to a specific region or desired fragment of Aβ without binding to other nonoverlapping fragments of Aβ. The latter screening can be accomplished by determining binding of an antibody to a collection of deletion mutants of an Aβ peptide and determining which deletion mutants bind to the antibody. Binding can be assessed, for example, by Western blot or ELISA. The smallest fragment to show specific binding to the antibody defines the epitope of the antibody. Alternatively, epitope specificity can be determined by a competition assay is which a test and reference antibody compete for binding to Aβ. If the test and reference antibodies compete, then they bind to the same epitope or epitopes sufficiently proximal such that binding of one antibody interferes with binding of the other. The preferred isotype for such antibodies is mouse isotype IgG2a or equivalent isotype in other species. Mouse isotype IgG2a is the equivalent of human isotype IgG1 (e.g., human IgG1).

2. Chimeric and Humanized Antibodies

The present invention also features chimeric and/or humanized antibodies (i.e., chimeric and/or humanized immunoglobulins) specific for beta amyloid peptide. Chimeric and/or humanized antibodies have the same or similar binding specificity and affinity as a mouse or other nonhuman antibody that provides the starting material for construction of a chimeric or humanized antibody.

A. Production of Chimeric Antibodies

The term "chimeric antibody" refers to an antibody whose light and heavy chain genes have been constructed, typically by genetic engineering, from immunoglobulin gene segments belonging to different species. For example, the variable (V) segments of the genes from a mouse monoclonal antibody may be joined to human constant (C) segments, such as IgG1 and IgG4. Human isotype IgG1 is preferred. A typical chimeric antibody is thus a hybrid protein consisting of the V or antigen-binding domain from a mouse antibody and the C or effector domain from a human antibody.

B. Production of Humanized Antibodies

The term "humanized antibody" refers to an antibody comprising at least one chain comprising variable region framework residues substantially from a human antibody chain (referred to as the acceptor immunoglobulin or antibody) and at least one complementarity determining region substantially from a mouse antibody, (referred to as the donor immunoglobulin or antibody). See, Queen et al., *Proc. Natl. Acad. Sci. USA* 86:10029–10033 (1989), U.S. Pat. No. 5,530,101, U.S. Pat. No. 5,585,089, U.S. Pat. No. 5,693,761, U.S. Pat. Selick et al., WO 90/07861, and Winter, U.S. Pat. No. 5,225,539 (incorporated by reference in their entirety for all purposes). The constant region(s), if present, are also substantially or entirely from a human immunoglobulin.

The substitution of mouse CDRs into a human variable domain framework is most likely to result in retention of their correct spatial orientation if the human variable domain framework adopts the same or similar conformation to the mouse variable framework from which the CDRs originated. This is achieved by obtaining the human variable domains from human antibodies whose framework sequences exhibit a high degree of sequence identity with the murine variable framework domains from which the CDRs were derived. The heavy and light chain variable framework regions can be derived from the same or different human antibody sequences. The human antibody sequences can be the sequences of naturally occurring human antibodies or can be consensus sequences of several human antibodies. See Kettleborough et al., *Protein Engineering* 4:773 (1991); Kolbinger et al., *Protein Engineering* 6:971 (1993) and Carter et al., WO 92/22653.

Having identified the complementarity determining regions of the murine donor immunoglobulin and appropriate human acceptor immunoglobulins, the next step is to determine which, if any, residues from these components should be substituted to optimize the properties of the resulting humanized antibody. In general, substitution of human amino acid residues with murine should be minimized, because introduction of murine residues increases the risk of the antibody eliciting a human-anti-mouse-antibody (HAMA) response in humans. Art-recognized methods of determining immune response can be performed to monitor a HAMA response in a particular patient or during clinical trials. Patients administered humanized antibodies can be given an immunogenicity assessment at the beginning and throughout the administration of said therapy. The HAMA response is measured, for example, by detecting antibodies to the humanized therapeutic reagent, in serum samples from the patient using a method known to one in the art, including surface plasmon resonance technology (BIACORE) and/or solid-phase ELISA analysis.

Certain amino acids from the human variable region framework residues are selected for substitution based on their possible influence on CDR conformation and/or binding to antigen. The unnatural juxtaposition of murine CDR regions with human variable framework region can result in unnatural conformational restraints, which, unless corrected by substitution of certain amino acid residues, lead to loss of binding affinity.

The selection of amino acid residues for substitution is determined, in part, by computer modeling. Computer hardware and software are described herein for producing three-dimensional images of immunoglobulin molecules. In general, molecular models are produced starting from solved structures for immunoglobulin chains or domains thereof. The chains to be modeled are compared for amino acid sequence similarity with chains or domains of solved three-dimensional structures, and the chains or domains showing the greatest sequence similarity is/are selected as starting points for construction of the molecular model. Chains or domains sharing at least 50% sequence identity are selected for modeling, and preferably those sharing at least 60%, 70%, 80%, 90% sequence identity or more are selected for modeling. The solved starting structures are modified to allow for differences between the actual amino acids in the immunoglobulin chains or domains being modeled, and those in the starting structure. The modified structures are then assembled into a composite immunoglobulin. Finally, the model is refined by energy minimization and by verifying that all atoms are within appropriate distances from one another and that bond lengths and angles are within chemically acceptable limits.

The selection of amino acid residues for substitution can also be determined, in part, by examination of the characteristics of the amino acids at particular locations, or empirical observation of the effects of substitution or mutagenesis of particular amino acids. For example, when an amino acid differs between a murine variable region framework residue and a selected human variable region framework residue, the human framework amino acid should usually be substituted by the equivalent framework amino acid from the mouse antibody when it is reasonably expected that the amino acid:

(1) noncovalently binds antigen directly,
(2) is adjacent to a CDR region,
(3) otherwise interacts with a CDR region (e.g., is within about 3–6 Å of a CDR region as determined by computer modeling), or
(4) participates in the VL–VH interface.

Residues which "noncovalently bind antigen directly" include amino acids in positions in framework regions which are have a good probability of directly interacting with amino acids on the antigen according to established chemical forces, for example, by hydrogen bonding, Van der Waals forces, hydrophobic interactions, and the like.

CDR and framework regions are as defined by Kabat et al. or Chothia et al., supra. When framework residues, as defined by Kabat et al., supra, constitute structural loop residues as defined by Chothia et al., supra, the amino acids present in the mouse antibody may be selected for substitution into the humanized antibody. Residues which are "adjacent to a CDR region" include amino acid residues in positions immediately adjacent to one or more of the CDRs in the primary sequence of the humanized immunoglobulin chain, for example, in positions immediately adjacent to a CDR as defined by Kabat, or a CDR as defined by Chothia (See e.g., Chothia and Lesk JMB 196:901 (1987)). These amino acids are particularly likely to interact with the amino acids in the CDRs and, if chosen from the acceptor, to distort the donor CDRs and reduce affinity. Moreover, the adjacent amino acids may interact directly with the antigen (Amit et al., Science, 233:747 (1986), which is incorporated herein by reference) and selecting these amino acids from the donor may be desirable to keep all the antigen contacts that provide affinity in the original antibody.

Residues that "otherwise interact with a CDR region" include those that are determined by secondary structural analysis to be in a spatial orientation sufficient to affect a CDR region. In one embodiment, residues that "otherwise interact with a CDR region" are identified by analyzing a three-dimensional model of the donor immunoglobulin (e.g., a computer-generated model). A three-dimensional model, typically of the original donor antibody, shows that certain amino acids outside of the CDRs are close to the CDRs and have a good probability of interacting with amino acids in the CDRs by hydrogen bonding, Van der Waals forces, hydrophobic interactions, etc. At those amino acid positions, the donor immunoglobulin amino acid rather than the acceptor immunoglobulin amino acid may be selected. Amino acids according to this criterion will generally have a side chain atom within about 3 angstrom units (Å) of some atom in the CDRs and must contain an atom that could interact with the CDR atoms according to established chemical forces, such as those listed above.

In the case of atoms that may form a hydrogen bond, the 3 Å is measured between their nuclei, but for atoms that do not form a bond, the 3 Å is measured between their Van der Waals surfaces. Hence, in the latter case, the nuclei must be within about 6 Å (3 Å plus the sum of the Van der Waals radii) for the atoms to be considered capable of interacting. In many cases the nuclei will be from 4 or 5 to 6 Å apart. In determining whether an amino acid can interact with the CDRs, it is preferred not to consider the last 8 amino acids of heavy chain CDR 2 as part of the CDRs, because from the viewpoint of structure, these 8 amino acids behave more as part of the framework.

Amino acids that are capable of interacting with amino acids in the CDRs, may be identified in yet another way. The solvent accessible surface area of each framework amino acid is calculated in two ways: (1) in the intact antibody, and (2) in a hypothetical molecule consisting of the antibody with its CDRs removed. A significant difference between these numbers of about 10 square angstroms or more shows that access of the framework amino acid to solvent is at least partly blocked by the CDRs, and therefore that the amino acid is making contact with the CDRs. Solvent accessible surface area of an amino acid may be calculated based on a three-dimensional model of an antibody, using algorithms known in the art (e.g., Connolly, J. Appl. Cryst. 16:548 (1983) and Lee and Richards, J. Mol. Biol. 55:379 (1971), both of which are incorporated herein by reference). Framework amino acids may also occasionally interact with the CDRs indirectly, by affecting the conformation of another framework amino acid that in turn contacts the CDRs.

The amino acids at several positions in the framework are known to be capable of interacting with the CDRs in many antibodies (Chothia and Lesk, supra, Chothia et al., supra and Tramontano et al., J. Mol. Biol. 215:175 (1990), all of which are incorporated herein by reference). Notably, the amino acids at positions 2, 48, 64 and 71 of the light chain and 26–30, 71 and 94 of the heavy chain (numbering according to Kabat) are known to be capable of interacting with the CDRs in many antibodies. The amino acids at positions 35 in the light chain and 93 and 103 in the heavy chain are also likely to interact with the CDRs. At all these numbered positions, choice of the donor amino acid rather than the acceptor amino acid (when they differ) to be in the humanized immunoglobulin is preferred. On the other hand, certain residues capable of interacting with the CDR region, such as the first 5 amino acids of the light chain, may sometimes be chosen from the acceptor immunoglobulin without loss of affinity in the humanized immunoglobulin.

Residues which "participate in the VL–VH interface" or "packing residues" include those residues at the interface between VL and VH as defined, for example, by Novotny and Haber, Proc. Natl. Acad. Sci. USA, 82:4592–66 (1985) or Chothia et al, supra Generally, unusual packing residues should be retained in the humanized antibody if they differ from those in the human frameworks.

In general, one or more of the amino acids fulfilling the above criteria is substituted. In some embodiments, all or most of the amino acids fulfilling the above criteria are substituted. Occasionally, there is some ambiguity about whether a particular amino acid meets the above criteria, and alternative variant immunoglobulins are produced, one of which has that particular substitution, the other of which does not. Alternative variant immunoglobulins so produced can be tested in any of the assays described herein for the desired activity, and the preferred immunoglobulin selected.

Usually the CDR regions in humanized antibodies are substantially identical, and more usually, identical to the corresponding CDR regions of the donor antibody. Although not usually desirable, it is sometimes possible to make one or more conservative amino acid substitutions of CDR residues without appreciably affecting the binding affinity of the resulting humanized immunoglobulin. By conservative substitutions is intended combinations such as gly, ala; val, ile, leu; asp, glu; asn, gln; ser, thr; lys, arg; and phe, tyr.

Additional candidates for substitution are acceptor human framework amino acids that are unusual or "rare" for a human immunoglobulin at that position. These amino acids can be substituted with amino acids from the equivalent position of the mouse donor antibody or from the equivalent positions of more typical human immunoglobulins. For example, substitution may be desirable when the amino acid in a human framework region of the acceptor immunoglobulin is rare for that position and the corresponding amino acid in the donor immunoglobulin is common for that position in human immunoglobulin sequences; or when the amino acid in the acceptor immunoglobulin is rare for that position and the corresponding amino acid in the donor immunoglobulin is also rare, relative to other human sequences. These criteria help ensure that an a typical amino acid in the human framework does not disrupt the antibody structure. Moreover, by replacing an unusual human acceptor amino acid with an amino acid from the donor antibody that happens to be typical for human antibodies, the humanized antibody may be made less immunogenic.

The term "rare", as used herein, indicates an amino acid occurring at that position in less than about 20% but usually less than about 10% of sequences in a representative sample of sequences, and the term "common", as used herein, indicates an amino acid occurring in more than about 25% but usually more than about 50% of sequences in a representative sample. For example, all human light and heavy chain variable region sequences are respectively grouped into "subgroups" of sequences that are especially homologous to each other and have the same amino acids at certain critical positions (Kabat et al., supra). When deciding whether an amino acid in a human acceptor sequence is "rare" or "common" among human sequences, it will often be preferable to consider only those human sequences in the same subgroup as the acceptor sequence.

Additional candidates for substitution are acceptor human framework amino acids that would be identified as part of a CDR region under the alternative definition proposed by Chothia et al., supra. Additional candidates for substitution are acceptor human framework amino acids that would be identified as part of a CDR region under the AbM and/or contact definitions.

Additional candidates for substitution are acceptor framework residues that correspond to a rare or unusual donor framework residue. Rare or unusual donor framework residues are those that are rare or unusual (as defined herein) for murine antibodies at that position. For murine antibodies, the subgroup can be determined according to Kabat and residue positions identified which differ from the consensus. These donor specific differences may point to somatic mutations in the murine sequence which enhance activity. Unusual residues that are predicted to affect binding are retained, whereas residues predicted to be unimportant for binding can be substituted.

Additional candidates for substitution are non-germline residues occurring in an acceptor framework region. For example, when an acceptor antibody chain (i.e., a human antibody chain sharing significant sequence identity with the donor antibody chain) is aligned to a germline antibody chain (likewise sharing significant sequence identity with the donor chain), residues not matching between acceptor chain framework and the germline chain framework can be substituted with corresponding residues from the germline sequence.

Other than the specific amino acid substitutions discussed above, the framework regions of humanized immunoglobulins are usually substantially identical, and more usually, identical to the framework regions of the human antibodies from which they were derived. Of course, many of the amino acids in the framework region make little or no direct contribution to the specificity or affinity of an antibody. Thus, many individual conservative substitutions of framework residues can be tolerated without appreciable change of the specificity or affinity of the resulting humanized immunoglobulin. Thus, in one embodiment the variable framework region of the humanized immunoglobulin shares at least 85% sequence identity to a human variable framework region sequence or consensus of such sequences. In another embodiment, the variable framework region of the humanized immunoglobulin shares at least 90%, preferably 95%, more preferably 96%, 97%, 98% or 99% sequence identity to a human variable framework region sequence or consensus of such sequences. In general, however, such substitutions are undesirable.

The humanized antibodies preferably exhibit a specific binding affinity for antigen of at least $10^7$, $10^8$, $10^9$ or $10^{10}$ $M^{-1}$. Usually the upper limit of binding affinity of the humanized antibodies for antigen is within a factor of three, four or five of that of the donor immunoglobulin. Often the lower limit of binding affinity is also within a factor of three, four or five of that of donor immunoglobulin. Alternatively, the binding affinity can be compared to that of a humanized antibody having no substitutions (e.g., an antibody having donor CDRs and acceptor FRs, but no FR substitutions). In such instances, the binding of the optimized antibody (with substitutions) is preferably at least two- to three-fold greater, or three- to four-fold greater, than that of the unsubstituted antibody. For making comparisons, activity of the various antibodies can be determined, for example, by BIACORE (i.e., surface plasmon resonance using unlabelled reagents) or competitive binding assays.

C. Production of Humanized 12B4 Antibodies

A preferred embodiment of the present invention features a humanized antibody to the N-terminus of Aβ, in particular, for use in the therapeutic and/or diagnostic methodologies described herein. A particularly preferred starting material for production of humanized antibodies is 12B4. 12B4 is specific for the N-terminus of Aβ and has been shown to mediate phagocytosis (e.g., induce phagocytosis) of amyloid plaque. The cloning and sequencing of cDNA encoding the 12B4 antibody heavy and light chain variable regions is described in Example I.

Suitable human acceptor antibody sequences are identified by computer comparisons of the amino acid sequences of the mouse variable regions with the sequences of known human antibodies. The comparison is performed separately for heavy and light chains but the principles are similar for each. In particular, variable domains from human antibodies whose framework sequences exhibit a high degree of sequence identity with the murine VL and VH framework regions were identified by query of the Kabat Database using NCBI BLAST (publicly accessible through the National Institutes of Health NCBI internet server) with the respective murine framework sequences. In one embodiment, acceptor sequences sharing greater that 50% sequence identity with murine donor sequences are selected. Preferably, acceptor antibody sequences sharing 60%, 70%, 80%, 90% or more are selected.

A computer comparison of 12B4 revealed that the 12B4 light chain shows the greatest sequence identity to human light chains of subtype kappa II, and that the 12B4 heavy chain shows greatest sequence identity to human heavy chains of subtype II, as defined by Kabat et al., supra. Thus, light and heavy human framework regions are preferably derived from human antibodies of these subtypes, or from consensus sequences of such subtypes. The preferred light chain human variable regions showing greatest sequence identity to the corresponding region from 12B4 are from an antibody having Kabat ID Number 005036. The preferred heavy chain human variable regions showing greatest sequence identity to the corresponding region from 12B4 are from an antibody having Kabat ID Number 000333, an antibody having Genbank Accession No. AAB35009, and an antibody having Genbank Accession No. AAD53816, with the antibody having Kabat ID Number 000333 being more preferred.

Residues are next selected for substitution, as follows. When an amino acid differs between a 12B4 variable framework region and an equivalent human variable framework region, the human framework amino acid should usually be substituted by the equivalent mouse amino acid if it is reasonably expected that the amino acid:

(1) noncovalently binds antigen directly, (2) is adjacent to a CDR region, is part of a CDR region under the alternative definition proposed by Chothia et al., supra, or otherwise interacts with a CDR region (e.g., is within about 3A of a CDR region), or (3) participates in the VL–VH interface.

Computer modeling of the 12B4 antibody heavy and light chain variable regions, and humanization of the 12B4 antibody is described in Example V. Briefly, a three-dimensional model is generated based on the closest solved murine antibody structures for the heavy and light chains. The model is further refined by a series of energy minimization steps to relieve unfavorable atomic contacts and optimize electrostatic and van der Walls interactions.

Three-dimensional structural information for the antibodies described herein is publicly available, for example, from the Research Collaboratory for Structural Bioinformatics' Protein Data Bank (PDB). The PDB is freely accessible via the World Wide Web internet and is described by Berman et al. (2000) *Nucleic Acids Research*, 28:235. Computer modeling allows for the identification of CDR-interacting residues. The computer model of the structure of 12B4 can in turn serve as a starting point for predicting the three-dimensional structure of an antibody containing the 12B4 complementarity determining regions substituted in human framework structures. Additional models can be constructed representing the structure as further amino acid substitutions are introduced.

In general, substitution of one, most or all of the amino acids fulfilling the above criteria is desirable. Accordingly, the humanized antibodies of the present invention will usually contain a substitution of a human light chain framework residue with a corresponding 12B4 residue in at least 1, 2, 3 or more of the chosen positions. The humanized antibodies also usually contain a substitution of a human heavy chain framework residue with a corresponding 12B4 residue in at least 1, 2, 3 or more of the chosen positions.

Occasionally, however, there is some ambiguity about whether a particular amino acid meets the above criteria, and alternative variant immunoglobulins are produced, one of which has that particular substitution, the other of which does not. In instances where substitution with a murine residue would introduce a residue that is rare in human immunoglobulins at a particular position, it may be desirable to test the antibody for activity with or without the particular substitution. If activity (e.g., binding affinity and/or binding specificity) is about the same with or without the substitution, the antibody without substitution may be preferred, as it would be expected to elicit less of a HAMA response, as described herein.

Other candidates for substitution are acceptor human framework amino acids that are unusual for a human immunoglobulin at that position. These amino acids can be substituted with amino acids from the equivalent position of more typical human immunoglobulins. Alternatively, amino acids from equivalent positions in the mouse 12B4 can be introduced into the human framework regions when such amino acids are typical of human immunoglobulin at the equivalent positions.

Other candidates for substitution are non-germline residues occurring in a framework region. By performing a computer comparison of 12B4 with known germline sequences, germline sequences with the greatest degree of sequence identity to the heavy or light chain can be identified. Alignment of the framework region and the germline sequence will reveal which residues may be selected for substitution with corresponding germline residues. Residues not matching between a selected light chain acceptor framework and one of these germline sequences could be selected for substitution with the corresponding germline residue.

Table 1 summarizes the sequence analysis of the 12B4 VH and VL regions. Additional mouse and human structures that can be used for computer modeling of the 12B4 antibody and additional human antibodies are set forth as well as germline sequences that can be used in selecting amino acid substitutions. Rare mouse residues are also set forth in Table 1. Rare mouse residues are identified by comparing the donor VL and/or VH sequences with the sequences of other members of the subgroup to which the donor VL and/or VH sequences belong (according to Kabat) and identifying the residue positions which differ from the consensus. These donor specific differences may point to somatic mutations which enhance activity. Unusual or rare residues close to the binding site may possibly contact the antigen, making it desirable to retain the mouse residue. However, if the unusual mouse residue is not important for binding, use of the corresponding acceptor residue is preferred as the mouse residue may create immunogenic neoepitopes in the humanized antibody. In the situation where an unusual residue in the donor sequence is actually a common residue in the corresponding acceptor sequence, the preferred residue is clearly the acceptor residue.

TABLE 1

Summary of 12B4 V region sequence

| Chain | VL | VH |
|---|---|---|
| Mouse Subgroup | II | Ib |
| Human Subgroup | II | II |
| Rare amino acids (% frequency) | K107 (0.542%) | T3, I11, L12, F24, S41, N75, D83, A85 |
| Chothia canonical class | L1: ~class 4 [1 rmf] L2: class 1 [1 lmk] L3: class 1 [1 tet] | H1: class 3 [1 ggi] H2: ~class 1 |
| Closest mouse MAb solved structure | 2PCP (2.2Å) | 1ETZ (2.6Å) |
| Homology with modeling template | 94% | 80% |
| Human Framework seq | KABID 005036 | 1-KABID 000333 2-AAB35009/1F7 3-AAD53816 |
| Germline ref for Hu Fr | A3/x12690 & A19/X63397 | 1: VH4-39/AB019439/ BAA75036.1 2: VH2-5/AB019440/ BAA75057.1 |

Kabat ID sequences referenced herein are publicly available, for example, from the Northwestern University Biomedical Engineering Department's Kabat Database of Sequences of Proteins of Immunological Interest. Three-dimensional structural information for antibodies described herein is publicly available, for example, from the Research Collaboratory for Structural Bioinformatics' Protein Data Bank (PDB). The PDB is freely accessible via the World Wide Web internet and is described by Berman et al. (2000) *Nucleic Acids Research*, p235–242. Germline gene sequences referenced herein are publicly available, for example, from the National Center for Biotechnology Information (NCBI) database of sequences in collections of Igh, Ig kappa and Ig lambda germline V genes (as a division of the National Library of Medicine (NLM) at the National Institutes of Health (NIH)). Homology searching of the NCBI "Ig Germline Genes" database is provided by IgG BLAST™.

In a preferred embodiment, a humanized antibody of the present invention contains (i) a light chain comprising a variable domain comprising murine 12B4 VL CDRs and a human acceptor framework, the framework having at least one, residue substituted with the corresponding 12B4 residue and (ii) a heavy chain comprising 12B4 VH CDRs and a human acceptor framework, the framework having at least one, preferably two, three, four, five, six, seven, eight, or nine residues substituted with the corresponding 12B4 residue, and, optionally, at least one, preferably two or three residues substituted with a corresponding human germline residue.

In another preferred embodiment, a humanized antibody of the present invention has structural features, as described herein, and further has at least one (preferably two, three, four or all) of the following activities: (1) binds soluble Aβ; (2) binds aggregated Aβ1–42 (e.g., as determined by ELISA); (3) binds Aβ in plaques (e.g., staining of AD and/or PDAPP plaques); (4) binds Aβ with two- to three-fold higher binding affinity as compared to chimeric 12B4 (e.g., 12B4 having murine variable region sequences and human constant region sequences); (5) mediates phagocytosis of Aβ (e.g., in an ex vivo phagocytosis assay, as described herein); and (6) crosses the blood-brain barrier (e.g., demonstrates short-term brain localization, for example, in a PDAPP animal model, as described herein).

In another preferred embodiment, a humanized antibody of the present invention has structural features, as described herein, binds Aβ in a manner or with an affinity sufficient to elicit at least one of the following in vivo effects: (1) reduce Aβ plaque burden; (2) prevent plaque formation; (3) reduce levels of soluble Aβ; (4) reduce the neuritic pathology associated with an amyloidogenic disorder; (5) lessen or ameliorate at least one physiological symptom associated with an amyloidogenic disorder; and/or (6) improve cognitive function.

In another preferred embodiment, a humanized antibody of the present invention has structural features, as described herein, and specifically binds to an epitope comprising residues 3–7 of Aβ.

In another preferred embodiment, a humanized antibody of the present invention has structural features, as described herein, binds to an N-terminal epitope within Aβ (e.g., binds to an epitope within amino acids 3–7 of Aβ), and is capable of reducing (1) Aβ peptide levels; (2) Aβ plaque burden; and (3) the neuritic burden or neuritic dystrophy associated with an amyloidogenic disorder.

The activities described above can be determined utilizing any one of a variety of assays described herein or in the art (e.g., binding assays, phagocytosis assays, etc.). Activities can be assayed either in vivo (e.g. using labeled assay components and/or imaging techniques) or in vitro (e.g., using samples or specimens derived from a subject). Activities can be assayed either directly or indirectly. In certain preferred embodiments, neurological endpoints (e.g., amyloid burden, neuritic burden, etc) are assayed. Such endpoints can be assayed in living subjects (e.g., in animal models of Alzheimer's disease or in human subjects, for example, undergoing immunotherapy) using non-invasive detection methodologies. Alternatively, such endpoints can be assayed in subjects post mortem. Assaying such endpoints in animal models and/or in human subjects post mortem is useful in assessing the effectiveness of various agents (e.g., humanized antibodies) to be utilized in similar immunotherapeutic applications. In other preferred embodiments, behavioral or neurological parameters can be assessed as indicators of the above neuropathological activities or endpoints.

3. Production of Variable Regions

Having conceptually selected the CDR and framework components of humanized immunoglobulins, a variety of methods are available for producing such immunoglobulins. Because of the degeneracy of the code, a variety of nucleic acid sequences will encode each immunoglobulin amino acid sequence. The desired nucleic acid sequences can be produced by de novo solid-phase DNA synthesis or by PCR mutagenesis of an earlier prepared variant of the desired polynucleotide. Oligonucleotide-mediated mutagenesis is a preferred method for preparing substitution, deletion and insertion variants of target polypeptide DNA. See Adelman et al., DNA 2:183 (1983). Briefly, the target polypeptide DNA is altered by hybridizing an oligonucleotide encoding the desired mutation to a single-stranded DNA template. After hybridization, a DNA polymerase is used to synthesize an entire second complementary strand of the template that incorporates the oligonucleotide primer, and encodes the selected alteration in the target polypeptide DNA.

4. Selection of Constant Regions

The variable segments of antibodies produced as described supra (e.g., the heavy and light chain variable regions of chimeric or humanized antibodies) are typically linked to at least a portion of an immunoglobulin constant region (Fc region), typically that of a human immunoglobulin. Human constant region DNA sequences can be isolated in accordance with well known procedures from a variety of human cells, but preferably immortalized B cells (see Kabat et al., supra, and Liu et al., WO87/02671) (each of which is incorporated by reference in its entirety for all purposes). Ordinarily, the antibody will contain both light chain and heavy chain constant regions. The heavy chain constant region usually includes CH1, hinge, CH2, CH3, and CH4 regions. The antibodies described herein include antibodies having all types of constant regions, including IgM, IgG, IgD, IgA and IgE, and any isotype, including IgG1, IgG2, IgG3 and IgG4. When it is desired that the antibody (e.g., humanized antibody) exhibit cytotoxic activity, the constant domain is usually a complement fixing constant domain and the class is typically IgG1. Human isotype IgG1 is preferred. Light chain constant regions can be lambda or kappa. The humanized antibody may comprise sequences from more than one class or isotype. Antibodies can be expressed as tetramers containing two light and two heavy chains, as separate heavy chains, light chains, as Fab, Fab' F(ab')2, and Fv, or as single chain antibodies in which heavy and light chain variable domains are linked through a spacer.

5. Expression of Recombinant Antibodies

Chimeric and humanized antibodies are typically produced by recombinant expression. Nucleic acids encoding light and heavy chain variable regions, optionally linked to constant regions, are inserted into expression vectors. The light and heavy chains can be cloned in the same or different expression vectors. The DNA segments encoding immunoglobulin chains are operably linked to control sequences in the expression vector(s) that ensure the expression of immunoglobulin polypeptides. Expression control sequences include, but are not limited to, promoters (e.g., naturally-associated or heterologous promoters), signal sequences, enhancer elements, and transcription termination sequences. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the crossreacting antibodies.

These expression vectors are typically replicable in the host organisms either as episomes or as an integral part of the host chromosomal DNA. Commonly, expression vectors contain selection markers (e.g., ampicillin-resistance, hygromycin-resistance, tetracycline resistance, kanamycin resistance or neomycin resistance) to permit detection of those cells transformed with the desired DNA sequences (see, e.g., Itakura et al., U.S. Pat. No. 4,704,362).

*E. coli* is one prokaryotic host particularly useful for cloning the polynucleotides (e.g. DNA sequences) of the present invention. Other microbial hosts suitable for use include bacilli, such as *Bacillus subtilis*, and other enterobacteriaceae, such as *Salmonella, Serratia*, and various *Pseudomonas* species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, are also useful for expression. *Saccharomyces* is a preferred yeast host, with suitable vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

In addition to microorganisms, mammalian tissue cell culture may also be used to express and produce the polypeptides of the present invention (e.g., polynucleotides encoding immunoglobulins or fragments thereof). See Winnacker, From Genes to Clones, VCH Publishers, N.Y., N.Y. (1987). Eukaryotic cells are actually preferred, because a number of suitable host cell lines capable of secreting heterologous proteins (e.g., intact immunoglobulins) have been developed in the art, and include CHO cell lines, various Cos cell lines, HeLa cells, preferably, myeloma cell lines, or transformed B-cells or hybridomas. Preferably, the cells are non-human. Expression vectors for these cells can include expression control sequences, such as an origin of replication, a promoter, and an enhancer (Queen et al., *Immunol. Rev.* 89:49 (1986)), and necessary processing information sites, such as ribosome binding sites, RNA splice sites, polyadenylation sites, and transcriptional terminator sequences. Preferred expression control sequences are promoters derived from immunoglobulin genes, SV40, adenovirus, bovine papilloma virus, cytomegalovirus and the like. See Co et al., *J. Immunol.* 148:1149 (1992).

Alternatively, antibody-coding sequences can be incorporated in transgenes for introduction into the genome of a transgenic animal and subsequent expression in the milk of the transgenic animal (see, e.g., Deboer et al., U.S. Pat. No. 5,741,957, Rosen, U.S. Pat. No. 5,304,489, and Meade et al., U.S. Pat. No. 5,849,992). Suitable transgenes include coding sequences for light and/or heavy chains in operable linkage with a promoter and enhancer from a mammary gland specific gene, such as casein or beta lactoglobulin.

The vectors containing the polynucleotide sequences of interest (e.g., the heavy and light chain encoding sequences and expression control sequences) can be transferred into the host cell by well-known methods, which vary depending on the type of cellular host. For example, calcium chloride transfection is commonly utilized for prokaryotic cells, whereas calcium phosphate treatment, electroporation, lipofection, biolistics or viral-based transfection may be used for other cellular hosts. (See generally Sambrook et al., *Molecular Cloning: A Laboratory Manual* (Cold Spring Harbor Press, 2nd ed., 1989) (incorporated by reference in its entirety for all purposes). Other methods used to transform mammalian cells include the use of polybrene, protoplast fusion, liposomes, electroporation, and microinjection (see generally, Sambrook et al., supra). For production of transgenic animals, transgenes can be microinjected into fertilized oocytes, or can be incorporated into the genome of embryonic stem cells, and the nuclei of such cells transferred into enucleated oocytes.

When heavy and light chains are cloned on separate expression vectors, the vectors are co-transfected to obtain expression and assembly of intact immunoglobulins. Once expressed, the whole antibodies, their dimers, individual light and heavy chains, or other immunoglobulin forms of the present invention can be purified according to standard procedures of the art, including ammonium sulfate precipitation, affinity columns, column chromatography, HPLC purification, gel electrophoresis and the like (see generally Scopes, Protein Purification (Springer-Verlag, N.Y., (1982)). Substantially pure immunoglobulins of at least about 90 to 95% homogeneity are preferred, and 98 to 99% or more homogeneity most preferred, for pharmaceutical uses.

6. Antibody Fragments

Also contemplated within the scope of the instant invention are antibody fragments. In one embodiment, fragments of non-human, and/or chimeric antibodies are provided. In another embodiment, fragments of humanized antibodies are provided. Typically, these fragments exhibit specific binding to antigen with an affinity of at least $10^7$, and more typically $10^8$ or $10^9$ $M^{-1}$. Humanized antibody fragments include separate heavy chains, light chains, Fab, Fab', F(ab')2, Fabc, and Fv. Fragments are produced by recombinant DNA techniques, or by enzymatic or chemical separation of intact immunoglobulins.

7. Testing Antibodies for Therapeutic Efficacy in Animal Models

Groups of 7–9 month old PDAPP mice each are injected with 0.5 mg in PBS of polyclonal anti-Aβ or specific anti-Aβ monoclonal antibodies. All antibody preparations are purified to have low endotoxin levels. Monoclonals can be prepared against a fragment by injecting the fragment or longer form of Aβ into a mouse, preparing hybridomas and screening the hybridomas for an antibody that specifically binds to a desired fragment of Aβ without binding to other nonoverlapping fragments of Aβ.

Mice are injected intraperitoneally as needed over a 4 month period to maintain a circulating antibody concentration measured by ELISA titer of greater than 1/1000 defined by ELISA to Aβ42 or other immunogen. Titers are monitored and mice are euthanized at the end of 6 months of injections. Histochemistry, Aβ levels and toxicology are performed post mortem. Ten mice are used per group.

8. Screening Antibodies for Clearing Activity

The invention also provides methods of screening an antibody for activity in clearing an amyloid deposit or any other antigen, or associated biological entity, for which clearing activity is desired. To screen for activity against an amyloid deposit, a tissue sample from a brain of a patient with Alzheimer's disease or an animal model having characteristic Alzheimer's pathology is contacted with phagocytic cells bearing an Fc receptor, such as microglial cells, and the antibody under test in a medium in vitro. The phagocytic cells can be a primary culture or a cell line, and can be of murine (e.g., BV-2 or C8-B4 cells) or human origin (e.g., THP-1 cells). In some methods, the components are combined on a microscope slide to facilitate microscopic monitoring. In some methods, multiple reactions are performed in parallel in the wells of a microtiter dish. In such a format, a separate miniature microscope slide can be mounted in the separate wells, or a nonmicroscopic detection format, such as ELISA detection of Aβ can be used. Preferably, a series of measurements is made of the amount of amyloid deposit in the in vitro reaction mixture, starting from a baseline value before the reaction has proceeded, and one or more test values during the reaction. The antigen can be detected by staining, for example, with a fluorescently labeled antibody to Aβ or other component of amyloid plaques. The antibody used for staining may or may not be the same as the antibody being tested for clearing activity. A reduction relative to baseline during the reaction of the amyloid deposits indicates that the antibody under test has clearing activity. Such antibodies are likely to be useful in preventing or treating Alzheimer's and other amyloidogenic diseases. Particularly useful antibodies for preventing or treating Alzheimer's and other amyloidogenic diseases include those capable of clearing both compact and diffuse amyloid plaques, for example, the 12B4 antibody of the instant invention, or chimeric or humanized versions thereof.

Analogous methods can be used to screen antibodies for activity in clearing other types of biological entities. The assay can be used to detect clearing activity against virtually any kind of biological entity. Typically, the biological entity has some role in human or animal disease. The biological entity can be provided as a tissue sample or in isolated form. If provided as a tissue sample, the tissue sample is preferably unfixed to allow ready access to components of the tissue sample and to avoid perturbing the conformation of the components incidental to fixing. Examples of tissue samples that can be tested in this assay include cancerous tissue, precancerous tissue, tissue containing benign growths such as warts or moles, tissue infected with pathogenic microorganisms, tissue infiltrated with inflammatory cells, tissue bearing pathological matrices between cells (e.g., fibrinous pericarditis), tissue bearing aberrant antigens, and scar tissue. Examples of isolated biological entities that can be used include Aβ, viral antigens or viruses, proteoglycans, antigens of other pathogenic microorganisms, tumor antigens, and adhesion molecules. Such antigens can be obtained from natural sources, recombinant expression or chemical synthesis, among other means. The tissue sample or isolated biological entity is contacted with phagocytic cells bearing Fc receptors, such as monocytes or microglial cells, and an antibody to be tested in a medium. The antibody can be directed to the biological entity under test or to an antigen associated with the entity. In the latter situation, the object is to test whether the biological entity is phagocytosed with the antigen. Usually, although not necessarily, the antibody and biological entity (sometimes with an associated antigen), are contacted with each other before adding the phagocytic cells. The concentration of the biological entity and/or the associated antigen remaining in the medium, if present, is then monitored. A reduction in the amount or concentration of antigen or the associated biological entity in the medium indicates the antibody has a clearing response against the antigen and/or associated biological entity in conjunction with the phagocytic cells (see, e.g., Example IV).

9. Chimeric/Humanized Antibodies Having Altered Effector Function

For the above-described antibodies of the invention comprising a constant region (Fc region), it may also be desirable to alter the effector function of the molecule. Generally, the effector function of an antibody resides in the constant or Fc region of the molecule which can mediate binding to various effector molecules, e.g., complement proteins or Fc receptors. The binding of complement to the Fc region is important, for example, in the opsonization and lysis of cell pathogens and the activation of inflammatory responses. The binding of antibody to Fc receptors, for example, on the surface of effector cells can trigger a number of important and diverse biological responses including, for example, engulfment and destruction of antibody-coated pathogens or particles, clearance of immune complexes, lysis of antibody-coated target cells by killer cells (i.e., antibody-dependent cell-mediated cytotoxicity, or ADCC), release of inflammatory mediators, placental transfer of antibodies, and control of immunoglobulin production.

Accordingly, depending on a particular therapeutic or diagnostic application, the above-mentioned immune functions, or only selected immune functions, may be desirable.

By altering the Fc region of the antibody, various aspects of the effector function of the molecule, including enhancing or suppressing various reactions of the immune system, with beneficial effects in diagnosis and therapy, are achieved.

The antibodies of the invention can be produced which react only with certain types of Fe receptors, for example, the antibodies of the invention can be modified to bind to only certain Fc receptors, or if desired, lack Fe receptor binding entirely, by deletion or alteration of the Fe receptor binding site located in the Fe region of the antibody. Other desirable alterations of the Fe region of an antibody of the invention are cataloged below. Typically the Kabat numbering system is used to indicate which amino acid residue(s) of the Fe region (e.g., of an IgG antibody) are altered (e.g., by amino acid substitution) in order to achieve a desired change in effector function. The numbering system is also employed to compare antibodies across species such that a desired effector function observed in, for example, a mouse antibody, can then be systematically engineered into a human, humanized, or chimeric antibody of the invention.

For example, it has been observed that antibodies (e.g., IgG antibodies) can be grouped into those found to exhibit tight, intermediate, or weak binding to an Fc receptor (e.g., an Fc receptor on human monocytes (FcγRI)). By comparison of the amino-acid sequences in these different affinity groups, a monocyte-binding site in the hinge-link region (Leu234-Ser239) has been identified. Moreover, the human FcγRI receptor binds human IgG1 and mouse IgG2a as a monomer, but the binding of mouse IgG2b is 100-fold weaker. A comparison of the sequence of these proteins in the hinge-link region shows that the sequence 234 to 238, i.e., Leu-Leu-Gly-Gly-Pro (SEQ ID NO:39) in the strong binders becomes Leu-Glu-Gly-Gly-Pro (SEQ ID NO:39) in mouse gamma 2b, i.e., weak binders. Accordingly, a corresponding change in a human antibody hinge sequence can be made if reduced FcγI receptor binding is desired. It is understood that other alterations can be made to achieve the same or similar results. For example, the affinity of FcγRI binding can be altered by replacing the specified residue with a residue having an inappropriate functional group on its sidechain, or by introducing a charged functional group (e.g., Glu or Asp) or for example an aromatic non-polar residue (e.g., Phe, Tyr, or Trp).

These changes can be equally applied to the murine, human, and rat systems given the sequence homology between the different immunoglobulins. It has been shown that for human IgG3, which binds to the human FcγRI receptor, changing Leu 235 to Glu destroys the interaction of the mutant for the receptor. The binding site for this receptor can thus be switched on or switched off by making the appropriate mutation.

Mutations on adjacent or close sites in the hinge link region (e.g., replacing residues 234, 236 or 237 by Ala) indicate that alterations in residues 234, 235, 236, and 237 at least affect affinity for the FcγRI receptor. Accordingly, the antibodies of the invention can also have an altered Fc region with altered binding affinity for FcγRI as compared with the unmodified antibody. Such an antibody conveniently has a modification at amino acid residue 234, 235, 236, or 237.

Affinity for other Fc receptors can be altered by a similar approach, for controlling the immune response in different ways.

As a further example, the lytic properties of IgG antibodies following binding of the C1 component of complement can be altered.

The first component of the complement system, C1, comprises three proteins known as C1q, C1r and C1s which bind tightly together. It has been shown that C1q is responsible for binding of the three protein complex to an antibody.

Accordingly, the C1q binding activity of an antibody can be altered by providing an antibody with an altered CH 2 domain in which at least one of the amino acid residues 318, 320, and 322 of the heavy chain has been changed to a residue having a different side chain. The numbering of the residues in the heavy chain is that of the EU index (see Kabat et al., supra). Other suitable alterations for altering, e.g., reducing or abolishing specific C1q-binding to an antibody include changing any one of residues 318 (Glu), 320 (Lys) and 322 (Lys), to Ala.

Moreover, by making mutations at these residues, it has been shown that C1q binding is retained as long as residue 318 has a hydrogen-bonding side chain and residues 320 and 322 both have a positively charged side chain.

C1q binding activity can be abolished by replacing any one of the three specified residues with a residue having an inappropriate functionality on its side chain. It is not necessary to replace the ionic residues only with Ala to abolish C1q binding. It is also possible to use other alkyl-substituted non-ionic residues, such as Gly, Ile, Leu, or Val, or such aromatic non-polar residues as Phe, Tyr, Trp and Pro in place of any one of the three residues in order to abolish C1q binding. In addition, it is also be possible to use such polar non-ionic residues as Ser, Thr, Cys, and Met in place of residues 320 and 322, but not 318, in order to abolish C1q binding activity.

It is also noted that the side chains on ionic or non-ionic polar residues will be able to form hydrogen bonds in a similar manner to the bonds formed by the Glu residue. Therefore, replacement of the 318 (Glu) residue by a polar residue may modify but not abolish C1q binding activity.

It is also known that replacing residue 297 (Asn) with Ala results in removal of lytic activity while only slightly reducing (about three fold weaker) affinity for C1q. This alteration destroys the glycosylation site and the presence of carbohydrate that is required for complement activation. Any other substitution at this site will also destroy the glycosylation site.

The invention also provides an antibody having an altered effector function wherein the antibody has a modified hinge region. The modified hinge region may comprise a complete hinge region derived from an antibody of different antibody class or subclass from that of the CH1 domain. For example, the constant domain (CH1) of a class IgG antibody can be attached to a hinge region of a class IgG4 antibody. Alternatively, the new hinge region may comprise part of a natural hinge or a repeating unit in which each unit in the repeat is derived from a natural hinge region. In one example, the natural hinge region is altered by converting one or more cysteine residues into a neutral residue, such as alanine, or by converting suitably placed residues into cysteine residues. Such alterations are carried out using art recognized protein chemistry and, preferably, genetic engineering techniques, as described herein.

In one embodiment of the invention, the number of cysteine residues in the hinge region of the antibody is reduced, for example, to one cysteine residue. This modification has the advantage of facilitating the assembly of the antibody, for example, bispecific antibody molecules and antibody molecules wherein the Fc portion has been replaced by an effector or reporter molecule, since it is only necessary to form a single disulfide bond. This modification also provides a specific target for attaching the hinge region either to another hinge region or to an effector or reporter molecule, either directly or indirectly, for example, by chemical means.

Conversely, the number of cysteine residues in the hinge region of the antibody is increased, for example, at least one more than the number of normally occurring cysteine residues. Increasing the number of cysteine residues can be used to stabilize the interactions between adjacent hinges. Another advantage of this modification is that it facilitates the use of cysteine thiol groups for attaching effector or reporter molecules to the altered antibody, for example, a radiolabel.

Accordingly, the invention provides for an exchange of hinge regions between antibody classes, in particular, IgG classes, and/or an increase or decrease in the number of cysteine residues in the hinge region in order to achieve an altered effector function (see for example U.S. Pat. No. 5,677,425 which is expressly incorporated herein). A determination of altered antibody effector function is made using the assays described herein or other art recognized techniques.

Importantly, the resultant antibody can be subjected to one or more assays to evaluate any change in biological activity compared to the starting antibody. For example, the ability of the antibody with an altered Fc region to bind complement or Fc receptors can be assessed using the assays disclosed herein as well as any art recognized assay.

Production of the antibodies of the invention is carried out by any suitable technique including techniques described herein as well as techniques known to those skilled in the art. For example an appropriate protein sequence, e.g. forming part of or all of a relevant constant domain, e.g., Fc region, i.e., CH2, and/or CH3 domain(s), of an antibody, and include appropriately altered residue(s) can be synthesized and then chemically joined into the appropriate place in an antibody molecule.

Preferably, genetic engineering techniques are used for producing an altered antibody. Preferred techniques include, for example, preparing suitable primers for use in polymerase chain reaction (PCR) such that a DNA sequence which encodes at least part of an IgG heavy chain, e.g., an Fc or constant region (e.g., CH2, and/or CH3) is altered, at one or more residues. The segment can then be operably linked to the remaining portion of the antibody, e.g., the variable region of the antibody and required regulatory elements for expression in a cell.

The present invention also includes vectors used to transform the cell line, vectors used in producing the transforming vectors, cell lines transformed with the transforming vectors, cell lines transformed with preparative vectors, and methods for their production.

Preferably, the cell line which is transformed to produce the antibody with an altered Fc region (i.e., of altered effector function) is an immortalized mammalian cell line (e.g., CHO cell).

Although the cell line used to produce the antibody with an altered Fc region is preferably a mammalian cell line, any other suitable cell line, such as a bacterial cell line or a yeast cell line, may alternatively be used.

B. Nucleic Acid Encoding Immunologic and Therapeutic Agents

Immune responses against amyloid deposits can also be induced by administration of nucleic acids encoding antibodies and their component chains used for passive immunization. Such nucleic acids can be DNA or RNA. A nucleic acid segment encoding an immunogen is typically linked to regulatory elements, such as a promoter and enhancer, that allow expression of the DNA segment in the intended target cells of a patient. For expression in blood cells, as is desirable for induction of an immune response, promoter and enhancer elements from light or heavy chain immunoglobulin genes or the CMV major intermediate early promoter and enhancer are suitable to direct expression. The linked regulatory elements and coding sequences are often cloned into a vector. For administration of double-chain antibodies, the two chains can be cloned in the same or separate vectors.

A number of viral vector systems are available including retroviral systems (see, e.g., Lawrie and Tumin, Cur. Opin. Genet. Develop. 3:102–109 (1993)); adenoviral vectors (see, e.g., Bett et al., J. Virol. 67:5911 (1993)); adeno-associated virus vectors (see, e.g., Zhou et al., J. Exp. Med. 179:1867 (1994)), viral vectors from the pox family including vaccinia virus and the avian pox viruses, viral vectors from the alpha virus genus such as those derived from Sindbis and Semliki Forest Viruses (see, e.g., Dubensky et al., J. Virol. 70:508 (1996)), Venezuelan equine encephalitis virus (see Johnston et al., U.S. Pat. No. 5,643,576) and rhabdoviruses, such as vesicular stomatitis virus (see Rose, U.S. Pat. No. 6,168,943) and papillomaviruses (Ohe et al., Human Gene Therapy 6:325 (1995); Woo et al., WO 94/12629 and Xiao & Brandsma, Nucleic Acids. Res. 24, 2630–2622 (1996)).

DNA encoding an immunogen, or a vector containing the same, can be packaged into liposomes. Suitable lipids and related analogs are described by Eppstein et al., U.S. Pat. No. 5,208,036, Felgner et al., U.S. Pat. No. 5,264,618, Rose, U.S. Pat. No. 5,279,833, and Epand et al., U.S. Pat. No. 5,283,185. Vectors and DNA encoding an immunogen can also be adsorbed to or associated with particulate carriers, examples of which include polymethyl methacrylate polymers and polylactides and poly (lactide-co-glycolides), see, e.g., McGee et al., J. Micro Encap. (1996).

Gene therapy vectors or naked polypeptides (e.g., DNA) can be delivered in vivo by administration to an individual patient, typically by systemic administration (e.g., intravenous, intraperitoneal, nasal, gastric, intradermal, intramuscular, subdermal, or intracranial infusion) or topical application (see e.g., Anderson et al., U.S. Pat. No. 5,399,346). The term "naked polynucleotide" refers to a polynucleotide not complexed with colloidal materials. Naked polynucleotides are sometimes cloned in a plasmid vector. Such vectors can further include facilitating agents such as bupivacine (Weiner et al., U.S. Pat. No. 5,593,972). DNA can also be administered using a gene gun. See Xiao & Brandsma, supra. The DNA encoding an immunogen is precipitated onto the surface of microscopic metal beads. The microprojectiles are accelerated with a shock wave or expanding helium gas, and penetrate tissues to a depth of several cell layers. For example, The ACCEL™ Gene Delivery Device, i.e., a DNA gun, manufactured by Agricetus, Inc. Middleton Wis. is suitable. Alternatively, naked DNA can pass through skin into the blood stream simply by spotting the DNA onto skin with chemical or mechanical irritation (see Howell et al., WO 95/05853).

In a further variation, vectors encoding immunogens can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

II. Prophylactic and Therapeutic Methods

The present invention is directed inter alia to treatment of Alzheimer's and other amyloidogenic diseases by administration of therapeutic immunological reagents (e.g., humanized immunoglobulins) to specific epitopes within Aβ to a patient under conditions that generate a beneficial therapeutic response in a patient (e.g., induction of phagocytosis of Aβ, reduction of plaque burden, inhibition of plaque formation, reduction of neuritic dystrophy, improving cognitive function, and/or reversing, treating or preventing cognitive decline) in the patient, for example, for the prevention or treatment of an amyloidogenic disease. The invention is also directed to use of the disclosed immunological reagents (e.g., humanized immunoglobulins) in the manufacture of a medicament for the treatment or prevention of an amyloidogenic disease.

In one aspect, the invention provides methods of preventing or treating a disease associated with amyloid deposits of Aβ in the brain of a patient. Such diseases include Alzheimer's disease, Down's syndrome and cognitive impairment. The latter can occur with or without other characteristics of an amyloidogenic disease. Some methods of the invention entail administering an effective dosage of an antibody that specifically binds to a component of an amyloid deposit to the patient. Such methods are particularly useful for preventing or treating Alzheimer's disease in human patients. Exemplary methods entail administering an effective dosage of an antibody that binds to Aβ. Preferred methods entail administering an effective dosage of an antibody that specifically binds to an epitope within residues 1–10 of Aβ, for example, antibodies that specifically bind to an epitope within residues 1–3 of Aβ, antibodies that specifically bind to an epitope within residues 1–4 of Aβ, antibodies that specifically bind to an epitope within residues 1–5 of Aβ, antibodies that specifically bind to an epitope within residues 1–6 of Aβ, antibodies that specifically bind to an epitope within residues 1–7 of Aβ, or antibodies that specifically bind to an epitope within residues 3–7 of Aβ. In yet another aspect, the invention features administering antibodies that bind to an epitope comprising a free N-terminal residue of Aβ. In yet another aspect, the invention features administering antibodies that bind to an epitope within residues of 1–10 of Aβ wherein residue 1 and/or residue 7 of Aβ is aspartic acid. In yet another aspect, the invention features administering antibodies that specifically bind to Aβ peptide without binding to full-length amyloid precursor protein (APP). In yet another aspect, the isotype of the antibody is human IgG1.

In yet another aspect, the invention features administering antibodies that bind to an amyloid deposit in the patient and induce a clearing response against the amyloid deposit. For example, such a clearing response can be effected by Fc receptor mediated phagocytosis.

Therapeutic agents of the invention are typically substantially pure from undesired contaminant. This means that an agent is typically at least about 50% w/w (weight/weight) purity, as well as being substantially free from interfering proteins and contaminants. Sometimes the agents are at least about 80% w/w and, more preferably at least 90 or about 95% w/w purity. However, using conventional protein purification techniques, homogeneous peptides of at least 99% w/w can be obtained.

The methods can be used on both asymptomatic patients and those currently showing symptoms of disease. The antibodies used in such methods can be human, humanized, chimeric or nonhuman antibodies, or fragments thereof (e.g., antigen binding fragments) and can be monoclonal or polyclonal, as described herein. In yet another aspect, the invention features administering antibodies prepared from a human immunized with Aβ peptide, which human can be the patient to be treated with antibody.

In another aspect, the invention features administering an antibody with a pharmaceutical carrier as a pharmaceutical composition. Alternatively, the antibody can be administered to a patient by administering a polynucleotide encoding at least one antibody chain. The polynucleotide is expressed to produce the antibody chain in the patient. Optionally, the polynucleotide encodes heavy and light chains of the antibody. The polynucleotide is expressed to produce the heavy and light chains in the patient. In exemplary embodiments, the patient is monitored for level of administered antibody in the blood of the patient.

The invention thus fulfills a longstanding need for therapeutic regimes for preventing or ameliorating the neuropathology and, in some patients, the cognitive impairment associated with Alzheimer's disease.

A. Patients Amenable to Treatment

Patients amenable to treatment include individuals at risk of disease but not showing symptoms, as well as patients presently showing symptoms. In the case of Alzheimer's disease, virtually anyone is at risk of suffering from Alzheimer's disease if he or she lives long enough. Therefore, the present methods can be administered prophylactically to the general population without the need for any assessment of the risk of the subject patient. The present methods are especially useful for individuals who have a known genetic risk of Alzheimer's disease. Such individuals include those having relatives who have experienced this disease, and those whose risk is determined by analysis of genetic or biochemical markers. Genetic markers of risk toward Alzheimer's disease include mutations in the APP gene, particularly mutations at position 717 and positions 670 and 671 referred to as the Hardy and Swedish mutations respectively (see Hardy, supra). Other markers of risk are mutations in the presenilin genes, PS1 and PS2, and ApoE4, family history of AD, hypercholesterolemia or atherosclerosis. Individuals presently suffering from Alzheimer's disease can be recognized from characteristic dementia, as well as the presence of risk factors described above. In addition, a number of diagnostic tests are available for identifying individuals who have AD. These include measurement of CSF tau and Aβ42 levels. Elevated tau and decreased Aβ42 levels signify the presence of AD. Individuals suffering from Alzheimer's disease can also be diagnosed by ADRDA criteria as discussed in the Examples section.

In asymptomatic patients, treatment can begin at any age (e.g., 10, 20, 30). Usually, however, it is not necessary to begin treatment until a patient reaches 40, 50, 60 or 70. Treatment typically entails multiple dosages over a period of time. Treatment can be monitored by assaying antibody levels over time. If the response falls, a booster dosage is indicated. In the case of potential Down's syndrome patients, treatment can begin antenatally by administering therapeutic agent to the mother or shortly after birth.

B. Treatment Regimes and Dosages

In prophylactic applications, pharmaceutical compositions or medicaments are administered to a patient susceptible to, or otherwise at risk of, Alzheimer's disease in an amount sufficient to eliminate or reduce the risk, lessen the severity, or delay the outset of the disease, including biochemical, histologic and/or behavioral symptoms of the disease, its complications and intermediate pathological phenotypes presenting during development of the disease. In therapeutic applications, compositions or medicaments are administered to a patient suspected of, or already suffering from such a disease in an amount sufficient to cure, or at least partially arrest, the symptoms of the disease (biochemical, histologic and/or behavioral), including its complications and intermediate pathological phenotypes in development of the disease.

In some methods, administration of agent reduces or eliminates myocognitive impairment in patients that have not yet developed characteristic Alzheimer's pathology. An amount adequate to accomplish therapeutic or prophylactic treatment is defined as a therapeutically- or prophylactically-effective dose. In both prophylactic and therapeutic regimes, agents are usually administered in several dosages until a sufficient immune response has been achieved. The term "immune response" or "immunological response" includes the development of a humoral (antibody mediated) and/or a cellular (mediated by antigen-specific T cells or their secretion products) response directed against an antigen in a recipient subject. Such a response can be an active response, i.e., induced by administration of immunogen, or a passive response, i.e., induced by administration of immunoglobulin or antibody or primed T-cells. Typically, the immune response is monitored and repeated dosages are given if the immune response starts to wane.

Effective doses of the compositions of the present invention, for the treatment of the above described conditions vary depending upon many different factors, including means of administration, target site, physiological state of the patient, whether the patient is human or an animal, other medications administered, and whether treatment is prophylactic or therapeutic. Usually, the patient is a human but non-human mammals including transgenic mammals can also be treated. Treatment dosages need to be titrated to optimize safety and efficacy.

For passive immunization with an antibody, the dosage ranges from about 0.0001 to 100 mg/kg, and more usually 0.01 to 5 mg/kg (e.g., 0.02 mg/kg, 0.25 mg/kg, 0.5 mg/kg, 0.75 mg/kg, 1 mg/kg, 2 mg/kg, etc.), of the host body weight. For example dosages can be 1 mg/kg body weight or 10 mg/kg body weight or within the range of 1–10 mg/kg, preferably at least 1 mg/kg. Doses intermediate in the above ranges are also intended to be within the scope of the invention. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months. Exemplary dosage schedules include 1–10 mg/kg or 15 mg/kg on consecutive days, 30 mg/kg on alternate days or 60 mg/kg weekly. In some methods, two or more monoclonal antibodies with different binding specificities are administered simultaneously, in which case the dosage of each antibody administered falls within the ranges indicated.

Antibody is usually administered on multiple occasions. Intervals between single dosages can be weekly, monthly or yearly. Intervals can also be irregular as indicated by measuring blood levels of antibody to Aβ in the patient. In some methods, dosage is adjusted to achieve a plasma antibody concentration of 1–1000 μg/ml and in some methods 25–300 μg/ml. Alternatively, antibody can be administered as a sustained release formulation, in which case less frequent administration is required. Dosage and frequency vary depending on the half-life of the antibody in the patient. In general, humanized antibodies show the longest half-life, followed by chimeric antibodies and nonhuman antibodies The dosage and frequency of administration can vary depending on whether the treatment is prophylactic or therapeutic. In prophylactic applications, compositions containing the present antibodies or a cocktail thereof are administered to a patient not already in the disease state to enhance the patient's resistance. Such an amount is defined to be a "prophylactic effective dose." In this use, the precise amounts again depend upon the patient's state of health and general immunity, but generally range from 0.1 to 25 mg per dose, especially 0.5 to 2.5 mg per dose. A relatively low dosage is administered at relatively infrequent intervals over a long period of time. Some patients continue to receive treatment for the rest of their lives.

In therapeutic applications, a relatively high dosage (e.g., from about 1 to 200 mg of antibody per dose, with dosages of from 5 to 25 mg being more commonly used) at relatively short intervals is sometimes required until progression of the disease is reduced or terminated, and preferably until the patient shows partial or complete amelioration of symptoms of disease. Thereafter, the patent can be administered a prophylactic regime.

Doses for nucleic acids encoding antibodies range from about 10 ng to 1 g, 100 ng to 100 mg, 1 μg to 10 mg, or 30–300 μg DNA per patient. Doses for infectious viral vectors vary from 10–100, or more, virions per dose.

Therapeutic agents can be administered by parenteral, topical, intravenous, oral, subcutaneous, intraarterial, intracranial, intraperitoneal, intranasal or intramuscular means for prophylactic and/or therapeutic treatment. The most typical route of administration of an immunogenic agent is subcutaneous although other routes can be equally effective. The next most common route is intramuscular injection. This type of injection is most typically performed in the arm or leg muscles. In some methods, agents are injected directly into a particular tissue where deposits have accumulated, for example intracranial injection. Intramuscular injection or intravenous infusion are preferred for administration of antibody. In some methods, particular therapeutic antibodies are injected directly into the cranium. In some methods, antibodies are administered as a sustained release composition or device, such as a Medipad™ device.

Agents of the invention can optionally be administered in combination with other agents that are at least partly effective in treatment of amyloidogenic disease. In the case of Alzheimer's and Down's syndrome, in which amyloid deposits occur in the brain, agents of the invention can also be administered in conjunction with other agents that increase passage of the agents of the invention across the blood-brain barrier. Agents of the invention can also be administered in combination with other agents that enhance access of the therapeutic agent to a target cell or tissue, for example, liposomes and the like. Coadministering such agents can decrease the dosage of a therapeutic agent (e.g., therapeutic antibody or antibody chain) needed to achieve a desired effect.

C. Pharmaceutical Compositions

Agents of the invention are often administered as pharmaceutical compositions comprising an active therapeutic agent, i.e., and a variety of other pharmaceutically acceptable components. See *Remington's Pharmaceutical Science* (15th ed., Mack Publishing Company, Easton, Pa. (1980)). The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

Pharmaceutical compositions can also include large, slowly metabolized macromolecules such as proteins, polysaccharides such as chitosan, polylactic acids, polyglycolic acids and copolymers (such as latex functionalized sepharose™, agarose, cellulose, and the like), polymeric amino acids, amino acid copolymers, and lipid aggregates (such as oil droplets or liposomes). Additionally, these carriers can function as immunostimulating agents (i.e., adjuvants).

For parenteral administration, agents of the invention can be administered as injectable dosages of a solution or suspension of the substance in a physiologically acceptable diluent with a pharmaceutical carrier that can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions. Antibodies can be administered in the form of a depot injection or implant preparation, which can be formulated in such a manner as to permit a sustained release of the active ingredient. An exemplary composition comprises monoclonal antibody at 5 mg/mL, formulated in aqueous buffer consisting of 50 mM L-histidine, 150 mM NaCl, adjusted to pH 6.0 with HCl.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above (see Langer, Science 249: 1527 (1990) and Hanes, Advanced Drug Delivery Reviews 28:97 (1997)). The agents of this invention can be administered in the form of a depot injection or implant preparation, which can be formulated in such a manner as to permit a sustained or pulsatile release of the active ingredient.

Additional formulations suitable for other modes of administration include oral, intranasal, and pulmonary formulations, suppositories, and transdermal applications. For suppositories, binders and carriers include, for example, polyalkylene glycols or triglycerides; such suppositories can be formed from mixtures containing the active ingredient in the range of 0.5% to 10%, preferably 1%–2%. Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained release formulations or powders and contain 10%–95% of active ingredient, preferably 25%–70%.

Topical application can result in transdermal or intradermal delivery. Topical administration can be facilitated by co-administration of the agent with cholera toxin or detoxified derivatives or subunits thereof or other similar bacterial toxins (See Glenn et al., Nature 391, 851 (1998)). Co-administration can be achieved by using the components as a mixture or as linked molecules obtained by chemical crosslinking or expression as a fusion protein.

Alternatively, transdermal delivery can be achieved using a skin path or using transferosomes (Paul et al., Eur. J. Immunol. 25:3521 (1995); Cevc et al., Biochem. Biophys. Acta 1368:201–15 (1998)).

III. Monitoring the Course of Treatment

The invention provides methods of monitoring treatment in a patient suffering from or susceptible to Alzheimer's, i.e., for monitoring a course of treatment being administered to a patient. The methods can be used to monitor both therapeutic treatment on symptomatic patients and prophylactic treatment on asymptomatic patients. In particular, the methods are useful for monitoring passive immunization (e.g., measuring level of administered antibody).

Some methods entail determining a baseline value, for example, of an antibody level or profile in a patient, before administering a dosage of agent, and comparing this with a value for the profile or level after treatment. A significant increase (i.e., greater than the typical margin of experimental error in repeat measurements of the same sample, expressed as one standard deviation from the mean of such measurements) in value of the level or profile signals a positive treatment outcome (i.e., that administration of the agent has achieved a desired response). If the value for immune response does not change significantly, or decreases, a negative treatment outcome is indicated.

In other methods, a control value (i.e., a mean and standard deviation) of level or profile is determined for a control population. Typically the individuals in the control population have not received prior treatment. Measured values of the level or profile in a patient after administering a therapeutic agent are then compared with the control value. A significant increase relative to the control value (e.g., greater than one standard deviation from the mean) signals a positive or sufficient treatment outcome. A lack of significant increase or a decrease signals a negative or insufficient treatment outcome. Administration of agent is generally continued while the level is increasing relative to the control value. As before, attainment of a plateau relative to control values is an indicator that the administration of treatment can be discontinued or reduced in dosage and/or frequency.

In other methods, a control value of the level or profile (e.g., a mean and standard deviation) is determined from a control population of individuals who have undergone treatment with a therapeutic agent and whose levels or profiles have plateaued in response to treatment. Measured values of levels or profiles in a patient are compared with the control value. If the measured level in a patient is not significantly different (e.g., more than one standard deviation) from the control value, treatment can be discontinued. If the level in a patient is significantly below the control value, continued administration of agent is warranted. If the level in the patient persists below the control value, then a change in treatment may be indicated.

In other methods, a patient who is not presently receiving treatment but has undergone a previous course of treatment is monitored for antibody levels or profiles to determine whether a resumption of treatment is required. The measured level or profile in the patient can be compared with a value previously achieved in the patient after a previous course of treatment. A significant decrease relative to the previous measurement (i.e., greater than a typical margin of error in repeat measurements of the same sample) is an indication that treatment can be resumed. Alternatively, the value measured in a patient can be compared with a control value (mean plus standard deviation) determined in a population of patients after undergoing a course of treatment. Alternatively, the measured value in a patient can be compared with a control value in populations of prophylactically treated patients who remain free of symptoms of disease, or populations of therapeutically treated patients who show amelioration of disease characteristics. In all of these cases, a significant decrease relative to the control level (i.e., more than a standard deviation) is an indicator that treatment should be resumed in a patient.

The tissue sample for analysis is typically blood, plasma, serum, mucous fluid or cerebrospinal fluid from the patient. The sample is analyzed, for example, for levels or profiles of antibodies to Aβ peptide, e.g., levels or profiles of humanized antibodies. ELISA methods of detecting antibodies specific to Aβ are described in the Examples section. In some methods, the level or profile of an administered antibody is determined using a clearing assay, for example, in an in vitro phagocytosis assay, as described herein. In such methods, a tissue sample from a patient being tested is contacted with amyloid deposits (e.g., from a PDAPP mouse) and phagocytic cells bearing Fc receptors. Subsequent clearing of the amyloid deposit is then monitored. The existence and extent of clearing response provides an indication of the existence and level of antibodies effective to clear Aβ in the tissue sample of the patient under test.

The antibody profile following passive immunization typically shows an immediate peak in antibody concentration followed by an exponential decay. Without a further dosage, the decay approaches pretreatment levels within a period of days to months depending on the half-life of the antibody administered.

In some methods, a baseline measurement of antibody to Aβ in the patient is made before administration, a second measurement is made soon thereafter to determine the peak antibody level, and one or more further measurements are made at intervals to monitor decay of antibody levels. When the level of antibody has declined to baseline or a predetermined percentage of the peak less baseline (e.g., 50%, 25% or 10%), administration of a further dosage of antibody is administered. In some methods, peak or subsequent measured levels less background are compared with reference levels previously determined to constitute a beneficial prophylactic or therapeutic treatment regime in other patients. If the measured antibody level is significantly less than a reference level (e.g., less than the mean minus one standard deviation of the reference value in population of patients benefiting from treatment) administration of an additional dosage of antibody is indicated.

Additional methods include monitoring, over the course of treatment, any art-recognized physiologic symptom (e.g., physical or mental symptom) routinely relied on by researchers or physicians to diagnose or monitor amyloidogenic diseases (e.g., Alzheimer's disease). For example, one can monitor cognitive impairment. The latter is a symptom of Alzheimer's disease and Down's syndrome but can also occur without other characteristics of either of these diseases. For example, cognitive impairment can be monitored by determining a patient's score on the Mini-Mental State Exam in accordance with convention throughout the course of treatment.

C. Kits

The invention further provides kits for performing the monitoring methods described above. Typically, such kits contain an agent that specifically binds to antibodies to Aβ.

The kit can also include a label. For detection of antibodies to Aβ, the label is typically in the form of labeled anti-idiotypic antibodies. For detection of antibodies, the agent can be supplied prebound to a solid phase, such as to the wells of a microtiter dish. Kits also typically contain labeling providing directions for use of the kit. The labeling may also include a chart or other correspondence regime correlating levels of measured label with levels of antibodies to Aβ. The term labeling refers to any written or recorded material that is attached to, or otherwise accompanies a kit at any time during its manufacture, transport, sale or use. For example, the term labeling encompasses advertising leaflets and brochures, packaging materials, instructions, audio or videocassettes, computer discs, as well as writing imprinted directly on kits.

The invention also provides diagnostic kits, for example, research, detection and/or diagnostic kits (e.g., for performing in vivo imaging). Such kits typically contain an antibody for binding to an epitope of Aβ, preferably within residues 1–10. Preferably, the antibody is labeled or a secondary labeling reagent is included in the kit. Preferably, the kit is labeled with instructions for performing the intended application, for example, for performing an in vivo imaging assay. Exemplary antibodies are those described herein.

D. In vivo Imaging

The invention provides methods of in vivo imaging amyloid deposits in a patient. Such methods are useful to diagnose or confirm diagnosis of Alzheimer's disease, or susceptibility thereto. For example, the methods can be used on a patient presenting with symptoms of dementia. If the patient has abnormal amyloid deposits, then the patient is likely suffering from Alzheimer's disease. The methods can also be used on asymptomatic patients. Presence of abnormal deposits of amyloid indicates susceptibility to future symptomatic disease. The methods are also useful for monitoring disease progression and/or response to treatment in patients who have been previously diagnosed with Alzheimer's disease.

The methods work by administering a reagent, such as antibody that binds to Aβ, to the patient and then detecting the agent after it has bound. Preferred antibodies bind to Aβ deposits in a patient without binding to full length APP polypeptide. Antibodies binding to an epitope of Aβ within amino acids 1–10 are particularly preferred. In some methods, the antibody binds to an epitope within amino acids 7–10 of Aβ. Such antibodies typically bind without inducing a substantial clearing response. In other methods, the antibody binds to an epitope within amino acids 1–7 of Aβ. Such antibodies typically bind and induce a clearing response to Aβ. However, the clearing response can be avoided by using antibody fragments lacking a full-length constant region, such as Fabs. In some methods, the same antibody can serve as both a treatment and diagnostic reagent. In general, antibodies binding to epitopes C-terminal to residue 10 of Aβ do not show as strong a signal as antibodies binding to epitopes within residues 1–10, presumably because the C-terminal epitopes are inaccessible in amyloid deposits. Accordingly, such antibodies are less preferred.

Diagnostic reagents can be administered by intravenous injection into the body of the patient, or directly into the brain by intracranial injection or by drilling a hole through the skull. The dosage of reagent should be within the same ranges as for treatment methods. Typically, the reagent is labeled, although in some methods, the primary reagent with affinity for Aβ is unlabelled and a secondary labeling agent is used to bind to the primary reagent. The choice of label depends on the means of detection. For example, a fluorescent label is suitable for optical detection. Use of paramagnetic labels is suitable for tomographic detection without surgical intervention. Radioactive labels can also be detected using PET or SPECT.

Diagnosis is performed by comparing the number, size, and/or intensity of labeled loci, to corresponding baseline values. The base line values can represent the mean levels in a population of undiseased individuals. Baseline values can also represent previous levels determined in the same patient. For example, baseline values can be determined in a patient before beginning treatment, and measured values thereafter compared with the baseline values. A decrease in values relative to baseline signals a positive response to treatment.

The present invention will be more fully described by the following non-limiting examples.

EXAMPLES

The following Sequence identifiers are used throughout the Examples section to refer to immunoglobulin chain variable region nucleotide and amino acid sequences.

| Antibody | VL nucleotide sequence | VL amino acid sequence | VH nucleotide sequence | VH amino acid sequence |
|---|---|---|---|---|
| 12B4 | SEQ ID NO: 1 | SEQ ID NO: 2 | SEQ ID NO: 3 | SEQ ID NO: 4 |
| humanized 12B4v1 | SEQ ID NO: 5 | SEQ ID NO: 6 | SEQ ID NO: 7 | SEQ ID NO: 8 |
| humanized 12B4v2 | SEQ ID NO: 5 | SEQ ID NO: 6 | SEQ ID NO: 9 | SEQ ID NO: 10 |
| humanized 12B4v3 | SEQ ID NO: 5 | SEQ ID NO: 6 | SEQ ID NO: 11 | SEQ ID NO: 12 |
| germline A19 | SEQ ID NO: 29 | SEQ ID NO: 30 | | |
| Kabat ID 005036 | SEQ ID NO: 31 | SEQ ID NO: 32 | | |
| Kabat ID 000333 | | | SEQ ID NO: 33 | SEQ ID NO: 34 |
| germline VH4-61 | | | SEQ ID NO: 35 | SEQ ID NO: 36 |
| germline VH4-39 | | | SEQ ID NO: 37 | SEQ ID NO: 38 |

As used herein, an antibody or immunoglobulin sequence comprising a VL and/or VH sequence as set forth in any one of SEQ ID NOs: 1–12 or 29–38 can comprise either the full sequence or can comprise the mature sequence (i.e., mature peptide without the signal or leader peptide).

Example I

Cloning and Sequencing of the Mouse 12B4 Variable Regions

Cloning and Sequence Analysis of 12B4 VH. The VH and VL regions of 12B4 from hybridoma cells were cloned by RT-PCR and 5' RACE using mRNA from hybridoma cells and standard cloning methodology. The nucleotide sequence (SEQ ID NO:3) and deduced amino acid sequence (SEQ ID NO:4) derived from two independent cDNA clones encoding the presumed 12B4 VH domain, are set forth in Table 2 and Table 3, respectively.

TABLE 2

Mouse 12B4 VH DNA sequence.

(SEQ ID NO: 3)
ATGGACAGGCTTACTTCCTCATTCCTGCTGCTGATTGTCCCTGCATATGT

CCTGTCCCAGGTTACTCTGAAAGAGTCTGGCCCTGGGATATTGCAGCCCT

CCCAGACCCTCAGTCTGACTTGTTCTTTCTCTGGGTTTTCACTGAGCACT

AATGGTATGGGTGTGAGCTGGATTCGTCAGCCTTCAGGAAAGGGTCTGGA

GTGGCTGGCACACATTTACTGGGATGAGGACAAGCGCTATAACCCATCCC

TGAAGAGCCGGCTCACAATCTCCAAGGATACCTCTAACAATCAGGTATTC

CTCAAGATCACCAATGTGGACACTGCTGATACTGCCACATACTACTGTGC

TCGAAGGAGGATCATCTATGATGTTGAGGACTACTTTGACTACTGGGGCC

AAGGCACCACTCTCACAGTCTCCTCAG

*Leader peptide underlined.

TABLE 3

Mouse 12B4 VH amino acid sequence (SEQ ID NO: 4)
mdrltssflllivpayvlsqVTLKESGPGILQPSQTLSLTCSFSGFSLSt ngmgvsWIRQPSGKGLEWLAhiywdedkrynpslksRLTISKDTSNNQVF LKITNVDTADTATYYCARrriiydvedyfdyWGQGTTLTVSS

*Leader peptide and CDRS in lower case.

Cloning and Sequence Analysis of 12B4 VL. The light chain variable VL region of 12B4 was cloned in an analogous manner as the VH region. The nucleotide sequence (SEQ ID NO: 1) and deduced amino acid sequence (SEQ ID NO:2) derived from two independent cDNA clones encoding the presumed 12B4 VL domain, are set forth in Table 4 and Table 5, respectively.

TABLE 4

Mouse 12B4 VL DNA sequence (SEQ ID NO: 1)
ATGAAGTTGCCTGTTAGGCTGTTGGTGCTGATGTTCTGGATTCCTGCTTC

CAGCAGTGATGTTTTGATGACCCAAACTCCACTCTCCCTGCCTGTCAGTC

TTGGAGATCAAGCCTCCATCTCTTGCAGATCTAGTCAGAACATTGTTCAT

AGTAATGGAAACACCTATTTAGAATGGTACCTGCAGAAACCAGGCCAGTC

TCCAAAGCTCCTGATCTACAAAGTTTCCAACCGATTTTCTGGGGTCCCAG

ACAGGTTCAGTGGCAGTGGATCAGGGACAGATTTCACACTCAAGATCAGC

AGAGTGGAGGCTGAGGATCTGGGAGTTTATTACTGCTTTCAAGGTTCACA

TGTTCCGCTCACGTTCGGTGCTGGGACCAAGCTGGAGCTGAAAC

*Leader peptide underlined

TABLE 5

Mouse 12B4 VL amino acid sequence (SEQ ID NO: 2)
mklpvrllvlmfwipasssDVLMTQTPLSLPVSLGDQASISCrssqnivh sngntyleWYLQKPGQSPKLLIYkvsnrfSGVPDRFSGSGSGTDFTLKIS RVEAEDLGVYYCfqgshvpltFGAGTKLELK

*Leader peptide and CDRs in lower case.

The 12B4 VL and VH sequences meet the criteria for functional V regions in so far as they contain a contiguous ORF from the initiator methionine to the C-region, and share conserved residues characteristic of immunoglobulin V region genes. From N-terminal to C-terminal, both light and heavy chains comprise the domains FR1, CDR1, FR2, CDR2, FR3, CDR3 and FR4. The assignment of amino acids to each domain is in accordance with the numbering convention of Kabat et al., supra.

Example II

Expression of Chimeric 12B4 Antibody

Expression of Chimeric 12B4 Antibody: The variable heavy and light chain regions were re-engineered to encode splice donor sequences downstream of the respective VDJ or VJ junctions, and cloned into the mammalian expression vector pCMV-hγ1 for the heavy chain, and pCMV-hκ1 for the light chain. These vectors encode human γ1 and Ck constant regions as exonic fragments downstream of the inserted variable region cassette. Following sequence verification, the heavy chain and light chain expression vectors were co-transfected into COS cells. Various heavy chain clones were independently co-transfected with different chimeric light chain clones to confirm reproducibility of the result. Conditioned media was collected 48 hrs post transfection and assayed by western blot analysis for antibody production or ELISA for Aβ binding. The multiple transfectants all expressed heavy chain+light chain combinations which are recognized by a goat anti-human IgG (H+L) antibody on a western blot.

Figure 5A:
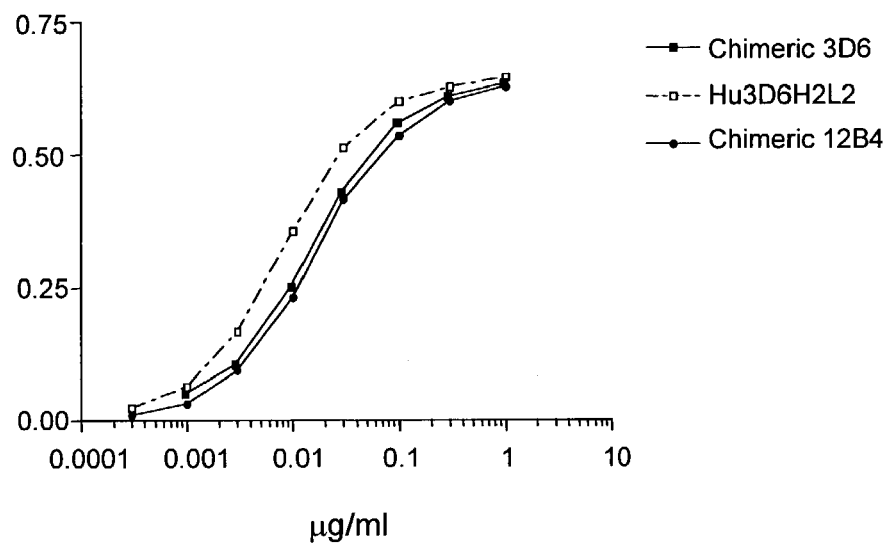
FIG. 5 graphically depicts the ELISA results from two independent experiments measuring the binding of chimeric 12B4, 3D6, and chimeric 3D6 to Aβ (panels A and B, respectively).
Figure 5B:
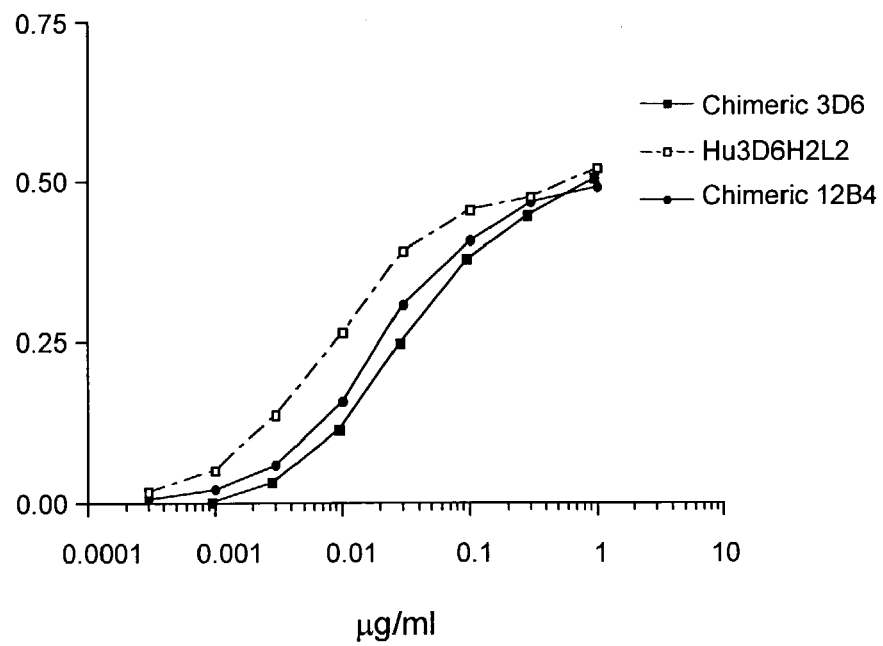
Figure 6:
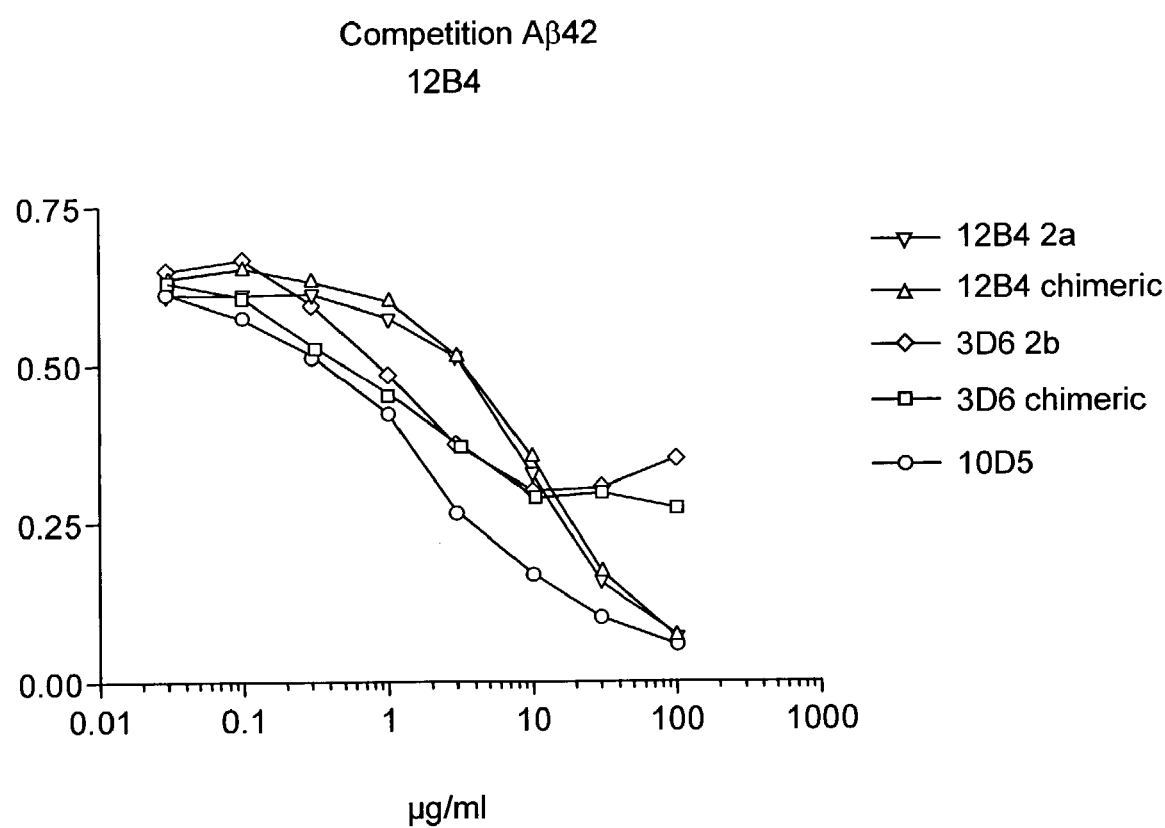
FIG. 6 graphically depicts competitive ELISA binding confirming functional activity of 12B4 and chimeric 12B4 as compared to 3D6, chimeric 3D6, and 10D5. Chimeric 12B4 (open triangles) competes with equal potency with its non biotinylated murine counterpart (open inverted triangles) for binding of biotinylated murine 12B4 to Aβ1–42 peptide.

Direct binding of chimeric 12B4 antibodies to Aβ was tested by ELISA assay. FIG. 5 demonstrates that chimeric 12B4 was found to bind to Aβ with high avidity, similar to that demonstrated by chimeric and humanized 3D6 (FIG. 5). (The cloning, characterization and humanization of 3D6 is described in pending U.S. patent application Ser. No. 10/010,942, the entire content of which is incorporated herein by this reference.) Furthermore, an ELISA based competitive inhibition assay revealed that the chimeric 12B4 and the murine 12B4 antibody competed equally with biotinylated murine and chimeric 3D6, as well as 10D5 (a murine monoclonal antibody of the IgGγ1 isotype which recognizes the same epitope as 12B4), in binding to Aβ. FIG. 6 demonstrates that chimeric 12B4 (dashed line, open triangles) competes with equal potency with its non biotinylated murine counterpart (solid line, closed triangles) for binding of biotinylated murine 12B4 to Aβ 1–42 peptide.

Example III

Efficacy of mAb 12B4 on various neuropathological endpoints in PDAPP mice

This Example describes the efficacy of murine mAb 12B4 on various neuropathological endpoints. Comparison of two mAbs, 12B4 and 3D6, is described. Both mAbs are of the IgG2a isotype and both bind an epitope within the N-terminus of the Aβ peptide.

Immunizations

PDAPP mice were passively immunized with either mAb 12B4 (recognizing Aβ 3–7) or mAb 3D6 (recognizing Aβ 1–5), both of the IgGγ2a isotype. 12B4 was tested at 10 mg/kg. 3D6 was administered at three different doses, 10 mg/kg, 1 mg/kg and 10 mg/kg once a month (1×4). An unrelated IgGγ2a antibody (TY 11/15) and PBS injections served as controls. Active immunization with Aβ peptide served as a comparison. Between 20 and 35 animals were analyzed in each group.

The neuropathological endpoints assayed include amyloid burden and neuritic burden.

Amyloid Burden

The extent of the frontal cortex occupied by amyloid deposits was determined by immunostaining with 3D6 followed by quantitative image analysis. The results of this analysis are shown in Table 6. All of the immunotherapies (e.g., immunization with 12B4, 3D6 (all doses tested) and Aβ peptide) led to a significant reduction of amyloid burden.

Neuritic Burden

Previously, it had been observed that 10D5 was unable to significantly reduce neuritic burden, suggesting that antibodies of the IgGγ2a isotype, but not other isotypes, are able to reduce neuritic burden in animal models of Alzheimer's disease (data not shown). Neuritic burden following passive immunization with 12B4 versus 3D6 (both of the IgGγ2a isotype) was thus determined in PDAPP mice by immunostaining of brain sections with anti-APP antibody 8E5 followed by quantitative image analysis. Neuritic dystrophy is indicated by the appearance of dystrophic neurites (e.g., neurites with a globular appearance) located in the immediate vicinity of amyloid plaques. The results of this analysis are shown in Table 7. These data indicate that treatment with 12B4 most significantly reduced neuritic burden. By contrast, 3D6 did not significantly reduce neuritic burden.

TABLE 6

| | Frontal Cortex Amyloid Burden | | | | | | |
|---|---|---|---|---|---|---|---|
| | PBS | TY 11/15 | 12B4 | 3D6, 10 mg/kg | 3D6, 1 mg/kg | 3D6, 10 mg/kg/4 wks. | Active |
| N | 31 | 30 | 33 | 29 | 31 | 32 | 24 |
| Median (% AB) | 15.182297 | 13.303288 | 2.317222 | 0.865671 | 2.286513 | 1.470956 | 2.162772 |
| Range | 0.160–31.961 | 0–61.706 | 0–14.642 | 0–7.064 | 0.077–63.362 | 0–10.688 | 0–30.715 |
| p Value (*M-W) | | .9425 ns | *** <.0001 | ***.0001 | *** <.0001 | *** <.0001 | ***.0004 |
| % Change | N/A | 12% | 85% | 94% | 85% | 90% | 86% |

TABLE 7

| | PBS | TY 11/15 | 12B4 | 3D6, 10 mg/kg | 3D6, 1 mg/kg | 3D6, 10 mg/kg/4 wks. | Active |
|---|---|---|---|---|---|---|---|
| | | | Frontal Cortex Neuritic Burden | | | | |
| N | 31 | 30 | 33 | 29 | 31 | 32 | 24 |
| Median (% NB) | 0.3946 | 0.3958 | 0.0816 | 0.4681 | 0.3649 | 0.4228 | 0.2344 |
| Range | 0–1.3828 | 0–2.6800 | 0–0.8127 | 0–1.3098 | 0–1.5760 | 0–1.8215 | 0–1.1942 |
| p Value (*M-W) | | .8967 ns | ***.0002 | .9587 ns | .6986 ns | >.9999 | ***.0381 |
| % Change | | 0% | 79% | 0% | 7% | 0% | 41% |

The above results indicate that treatment with an Aβ antibody of the IgGγ2a isotype may be necessary, but not sufficient, to reduce neuritic burden. Binding Aβ via a distinct epitope (i.e., Aβ 3–7) may also be essential to reduce this pathology in PDAPP mice.

The characterization of various neuropathological endpoints in the PDAPP mouse model of Alzheimer's disease provides valuable information to be used by the skilled artisan in designing appropriate human therapeutic immunization protocols. For example, reduction of neuritic burden may be accomplished in human subjects using a humanized version of 12B4 of the IgG1 subtype (i.e., the human equivalent of the IgGγ2A subtype in mice) which binds to an epitope within residues 3–7 of Aβ.

Example IV

Ex vivo Screening Assay for Activity of Antibodies Against Amyloid Deposits

To examine the effect of antibodies on plaque clearance, an ex vivo assay was utilized in which primary microglial cells were cultured with unfixed cryostat sections of either PDAPP mouse or human AD brains. Microglial cells were obtained from the cerebral cortices of neonate DBA/2N mice (1–3 days). The cortices were mechanically dissociated in HBSS⁻⁻ (Hanks' Balanced Salt Solution, Sigma) with 50 µg/ml DNase I (Sigma). The dissociated cells were filtered with a 100 µm cell strainer (Falcon), and centrifuged at 1000 rpm for 5 minutes. The pellet was resuspended in growth medium (high glucose DMEM, 10% FBS, 25 ng/ml recombinant murine GM-CSF (rmGM-CSF), and the cells were plated at a density of 2 brains per T-75 plastic culture flask. After 7–9 days, the flasks were rotated on an orbital shaker at 200 rpm for 2 h at 37° C. The cell suspension was centrifuged at 1000 rpm and resuspended in the assay medium.

10-µm cryostat sections of PDAPP mouse or human AD brains (postmortem interval <3 hr) were thaw mounted onto poly-lysine coated round glass coverslips and placed in wells of 24-well tissue culture plates. The coverslips were washed twice with assay medium consisting of H—SFM (Hybridoma-serum free medium, Gibco BRL) with 1% FBS, glutamine, penicillin/streptomycin, and 5 ng/ml rmGM-CSF (R&D). Control or anti-Aβ antibodies (12B4) were added at a 2× concentration (5 µg/ml final) for 1 hour. The microglial cells were then seeded at a density of $0.8 \times 10^6$ cells/ml assay medium. The cultures were maintained in a humidified incubator (37° C., 5% $CO_2$) for 24 hr or more. At the end of the incubation, the cultures were fixed with 4% paraformaldehyde and permeabilized with 0.1% Triton-X100. The sections were stained with biotinylated 3D6 followed by a streptavidin/Cy3 conjugate (Jackson ImmunoResearch).

The exogenous microglial cells were visualized by a nuclear stain (DAPI). The cultures were observed with an inverted fluorescent microscope (Nikon, TE300) and photomicrographs were taken with a SPOT digital camera using SPOT software (Diagnostic instruments).

Figure 7:
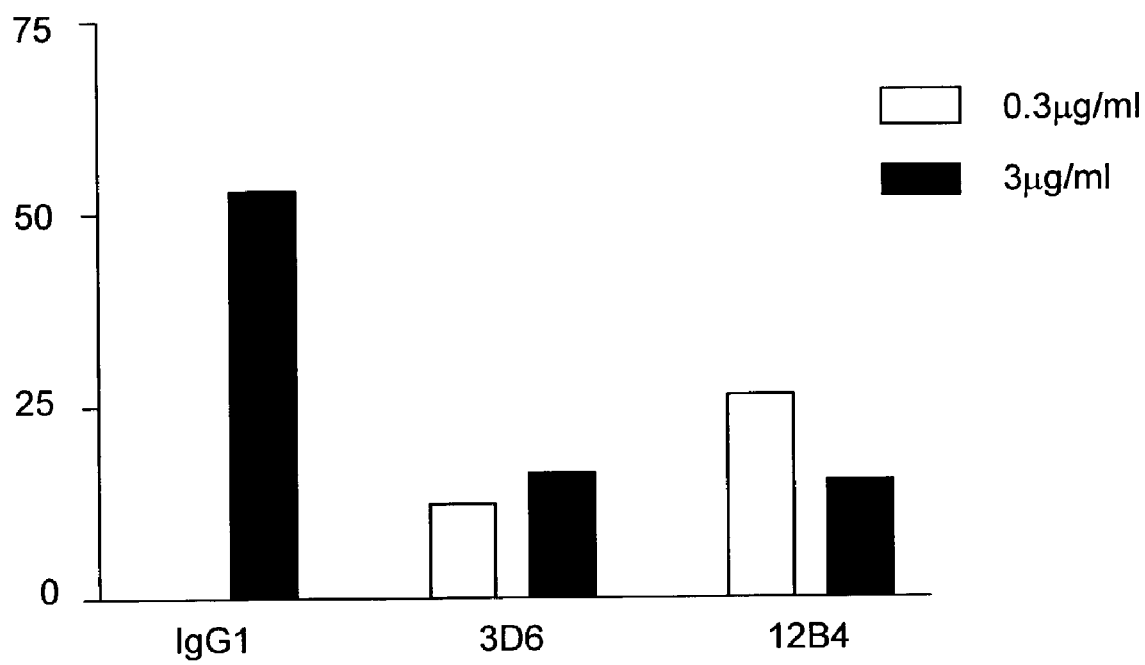
FIG. 7 graphically depicts an ex vivo phagocytosis assay testing the ability of chimeric 12B4, 3D6, and human IgG1 to mediate the uptake of Aβ by microglial cells on PDAPP brain sections.
Figure 8A:
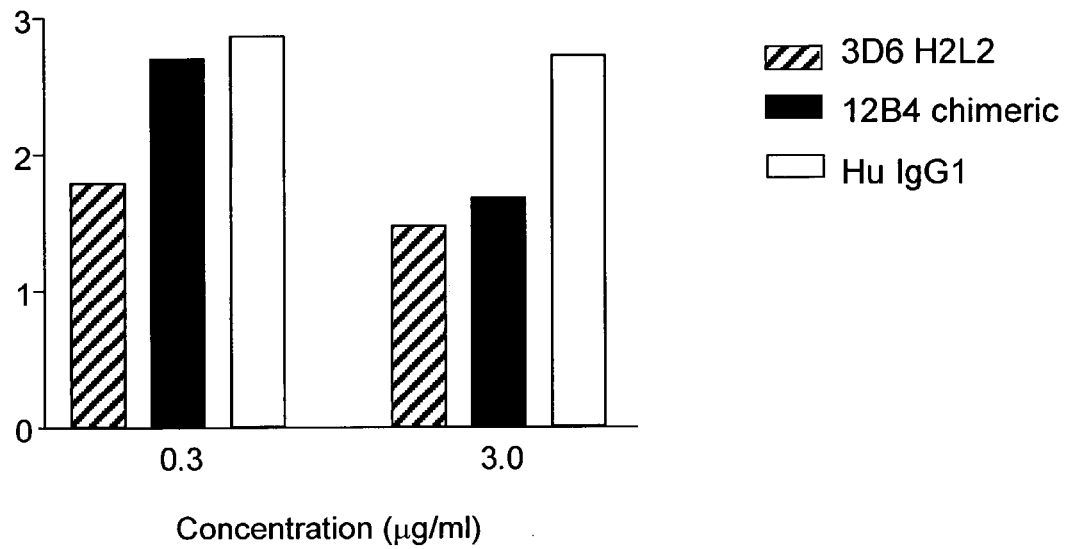
FIG. 8 graphically depicts the results from two independent ex vivo phagocytosis assays (panels A and B, respectively) testing the ability of chimeric 12B4, humanized 3D6, and human IgG1 to mediate the uptake of Aβ by microglial cells on AD brain sections.
Figure 8B:
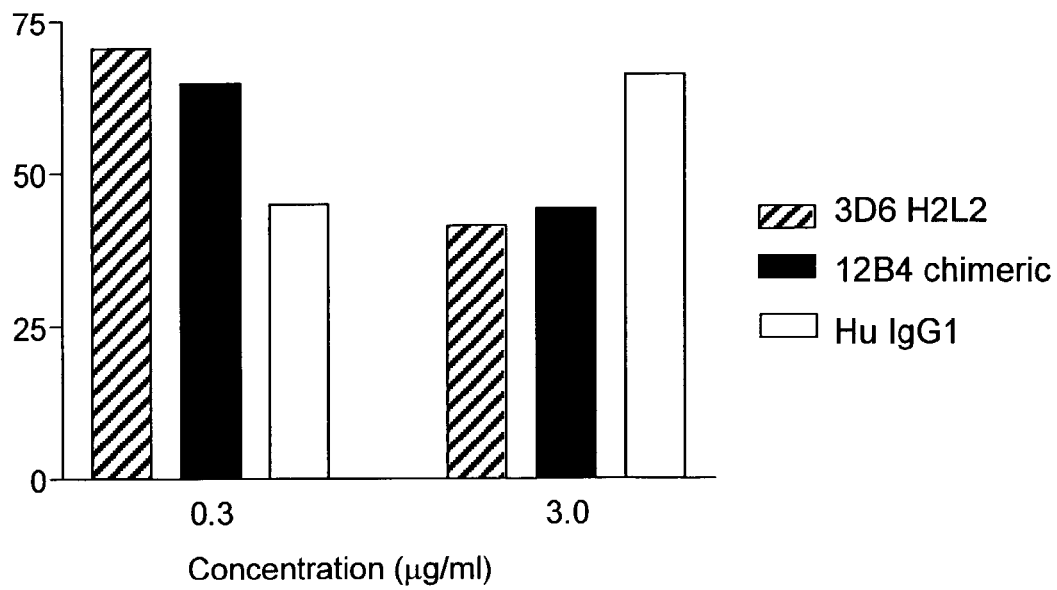

When the assay was performed with PDAPP brain sections in the presence of a control antibody having no in vivo efficacy, β-amyloid plaques remained intact and no phagocytosis was observed. In contrast, when adjacent sections were cultured in the presence of 3D6 or 12B4, the amyloid deposits were largely gone and the microglial cells showed numerous phagocytic vesicles containing Aβ (FIG. 7). Similar results were obtained with AD brain sections; 3D6 (a humanized version) and chimeric 12B4 induced phagocytosis of AD plaques, while control IgG1 was ineffective (FIGS. 8A–B).

The data presented in Examples II and III confirm function of the cloned 12B4 variable regions.

Example V

12B4 Humanization

A. 12B4 Humanized Antibody, Version 1

Homology/Molecular Modeling. In order to identify key structural framework residues in the murine 12B4 antibody, a three-dimensional model was generated based on the closest murine antibodies for the heavy and light chains. For this purpose, an antibody designated 2PCP was chosen as a template for modeling the 12B4 light chain (PDB ID: 2PCP, Lim et al. (1998) J. Biol. Chem. 273:28576), and an antibody designated 1ETZ was chosen as the template for modeling the heavy chain. (PDB ID: 1ETZ, Guddat et al. (2000) J. Mol. Biol. 302:853). Amino acid sequence alignment of 12B4 with the light chain and heavy chain of these antibodies revealed that the 2PCP and 1ETZ antibodies share significant sequence homology with 12B4. In addition, the CDR loops of the selected antibodies fall into the same canonical Chothia structural classes as do the CDR loops of 12B4. Therefore, 2PCP and 1ETZ were initially selected as antibodies of solved structure for homology modeling of 12B4.

A first pass homology model of 12B4 variable region based on the antibodies noted above was constructed using the Look & SegMod Modules GeneMine (v3.5) software package. This software was purchased under a perpetual license from Molecular Applications Group (Palo Alto, Calif.). This software package, authored by Drs. Michael Levitt and Chris Lee, facilitates the process of molecular modeling by automating the steps involved in structural modeling a primary sequence on a template of known structure based on sequence homology. Working on a Silicon Graphics IRIS workstation under a UNIX environment, the modeled structure is automatically refined by a series of energy minimization steps to relieve unfavorable atomic contacts and optimize electrostatic and van der Walls interactions. A further refined model was built using the modeling capability of QUANTA®, i.e., protein design homology modeling tools.

Selection of Human Acceptor Antibody Sequences. Suitable human acceptor antibody sequences were identified by computer comparisons of the amino acid sequences of the mouse variable regions with the sequences of known human antibodies. The comparison was performed separately for the 12B4 heavy and light chains. In particular, variable domains from human antibodies whose framework sequences exhibited a high degree of sequence identity with the murine VL and VH framework regions were identified by query of the Kabat Database using NCBI BLAST (publicly accessible through the National Institutes of Health NCBI internet server) with the respective murine framework sequences.

Two candidate sequences were chosen as acceptor sequences based on the following criteria: (1) homology with the subject sequence; (2) sharing canonical CDR structures with the donor sequence; and (3) not containing any rare amino acid residues in the framework regions. The selected acceptor sequence for VL is Kabat ID Number (KABID) 005036 (Genbank Accession No. X67904), and for VH is KABID 000333 (Genbank Accession No. X54437). First versions of humanized 12B4 antibody utilize these selected acceptor antibody sequences.

Substitution of Amino Acid Residues. As noted supra, the humanized antibodies of the invention comprise variable framework regions substantially from a human immunoglobulin (acceptor immunoglobulin) and complementarity determining regions substantially from a mouse immunoglobulin (donor immunoglobulin) termed 12B4. Having identified the complementarity determining regions of 12B4 and appropriate human acceptor immunoglobulins, the next step was to determine which, if any, residues from these components to substitute to optimize the properties of the resulting humanized antibody.

Figure 1B:
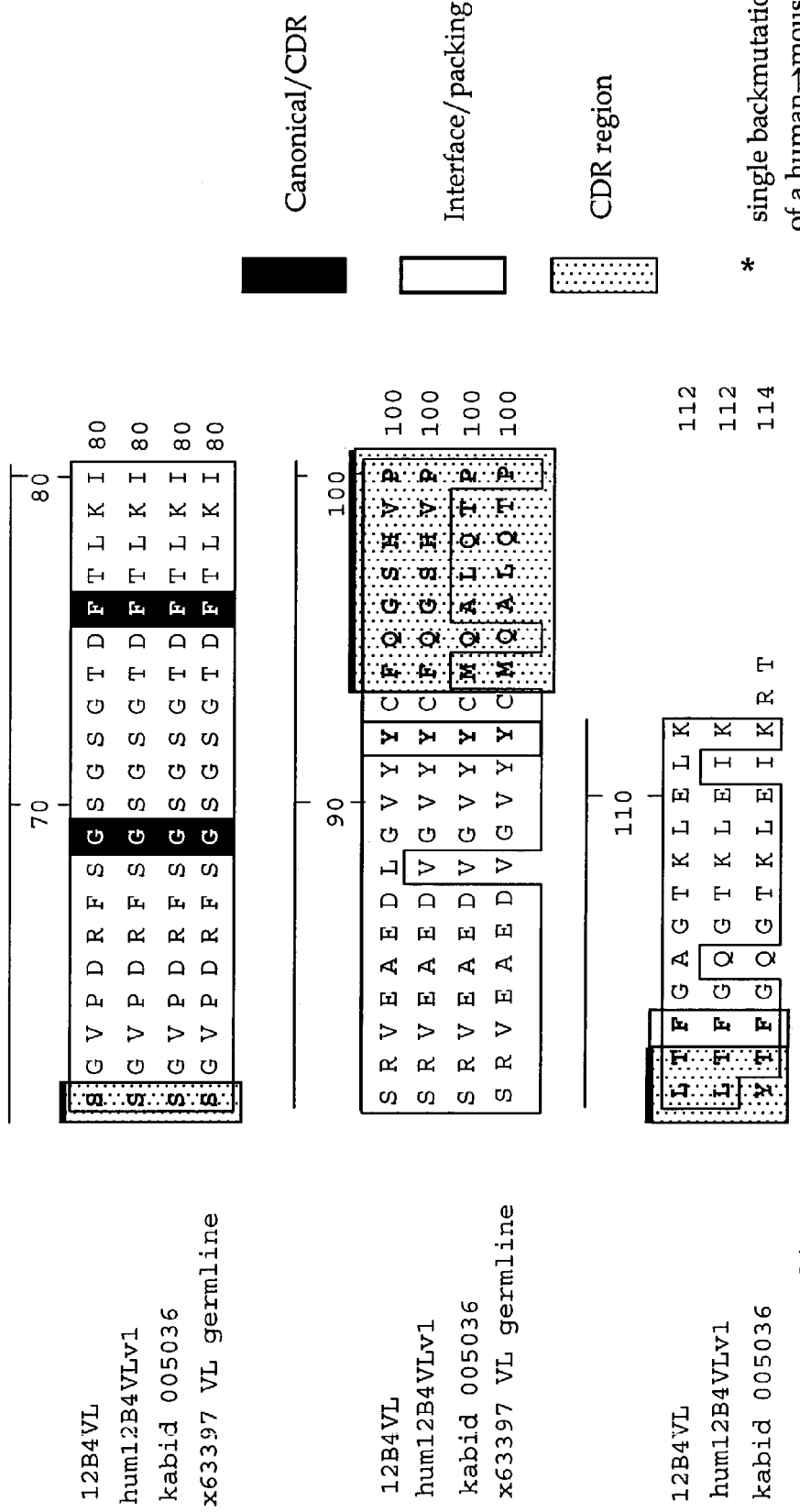

Reshaped Light Chain V Region:

The amino acid alignment of the reshaped light chain V region is shown in FIG. 1. The choice of the acceptor framework (Kabid 005036) is from the same human subgroup as that which corresponds to the murine V region, has no unusual framework residues, and the CDRs belong to the same Chothia canonical structure groups. A single back mutation (I2V) is dictated as this residue falls into the canonical classification. Version 1 of the reshaped VL is fully germline.

Figure 2A:
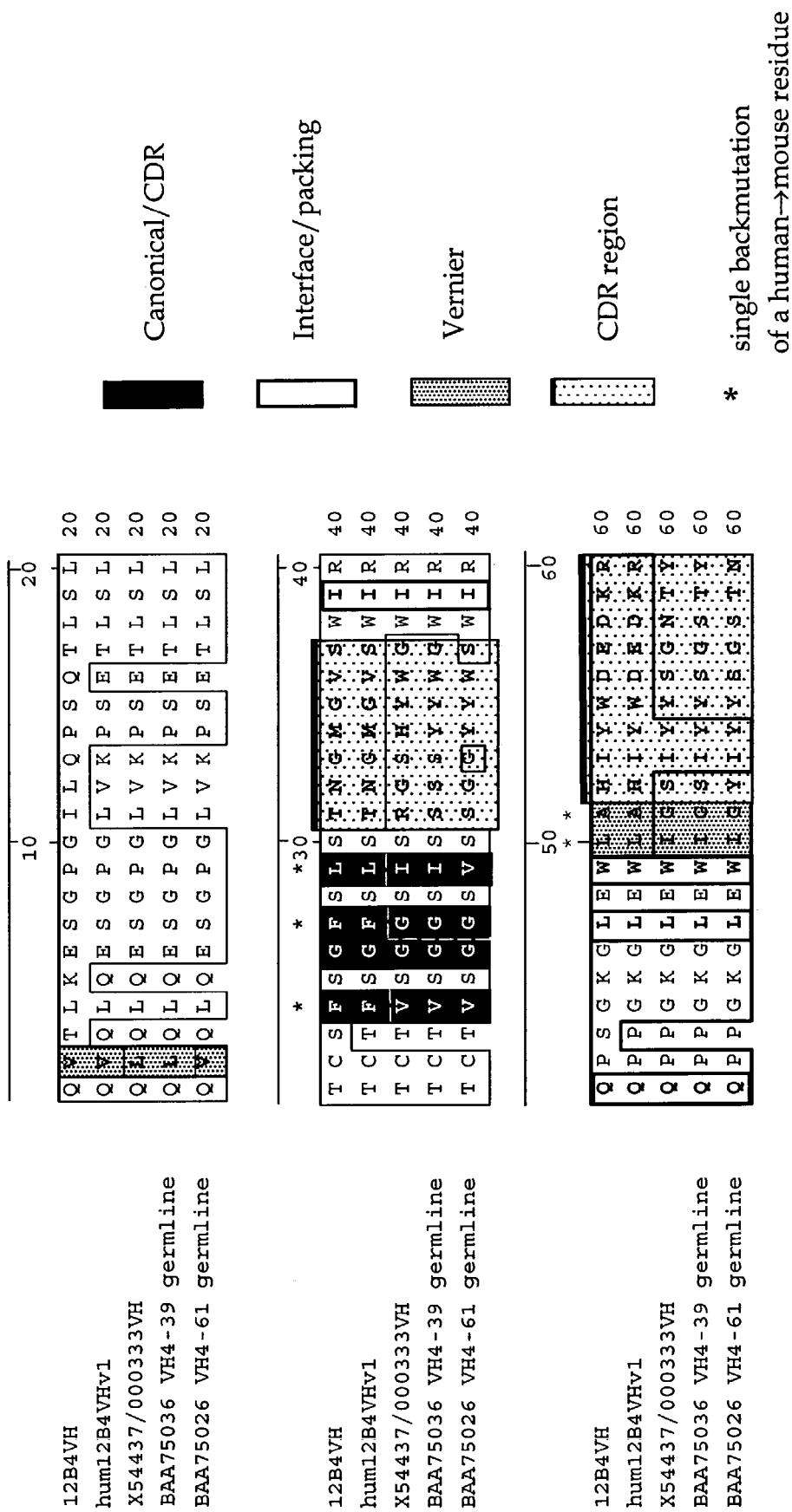
FIGS. 2A–B depicts an alignment of the amino acid sequences of the heavy chain of mouse 12B4 (mature peptide, SEQ ID NO:4), humanized 12B4 (version 1) (mature peptide, SEQ ID NO:8), Kabat ID 000333 (mature peptide, SEQ ID NO:34), and germline VH4–39 and VH4–61 antibodies (mature peptides, SEQ ID NOs: 38 and 36, respectively). Annotation is the same as for FIG. 1. Numbered from the first methionine, not Kabat numbering.
Figure 2B:
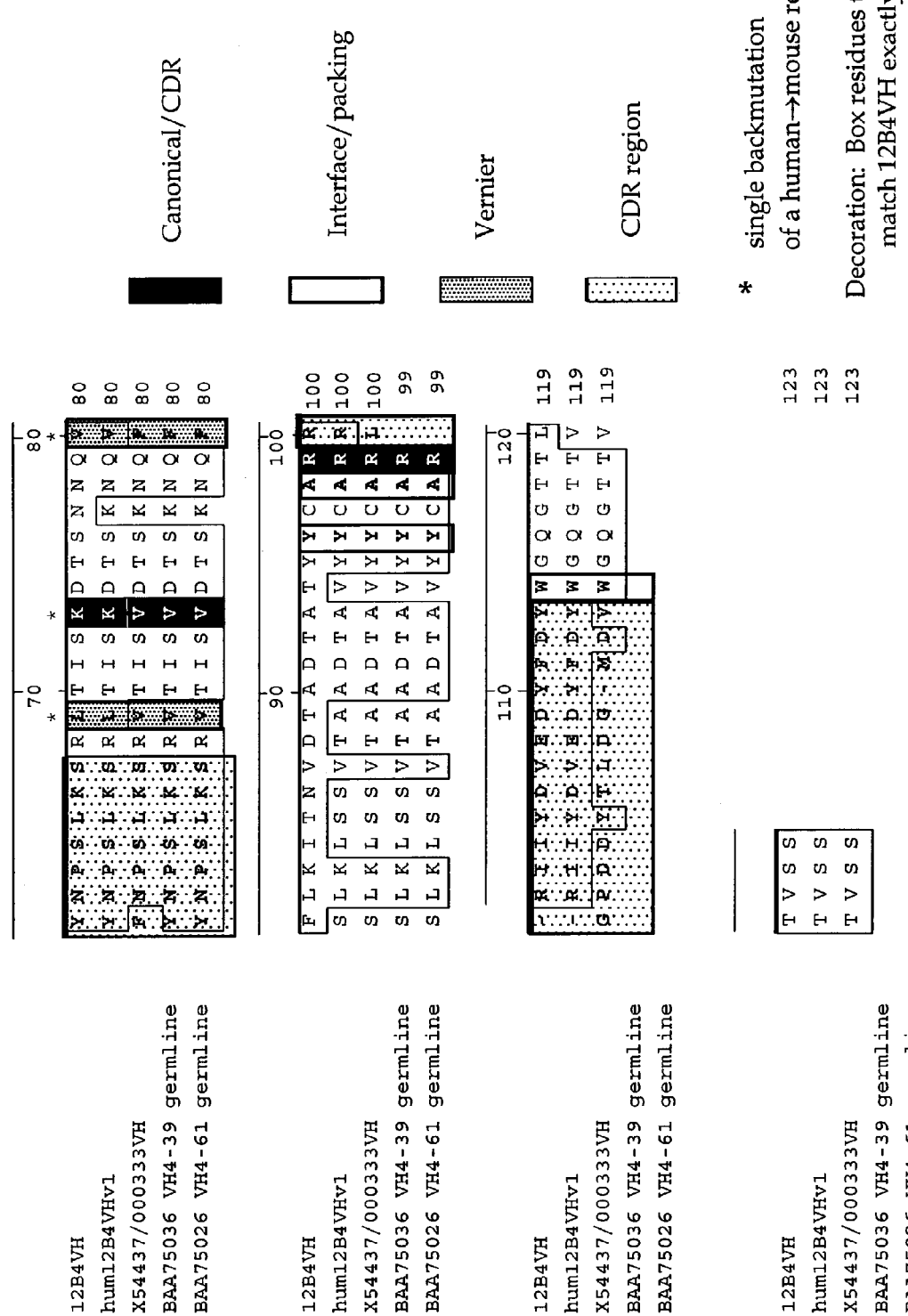
Figure 4D:
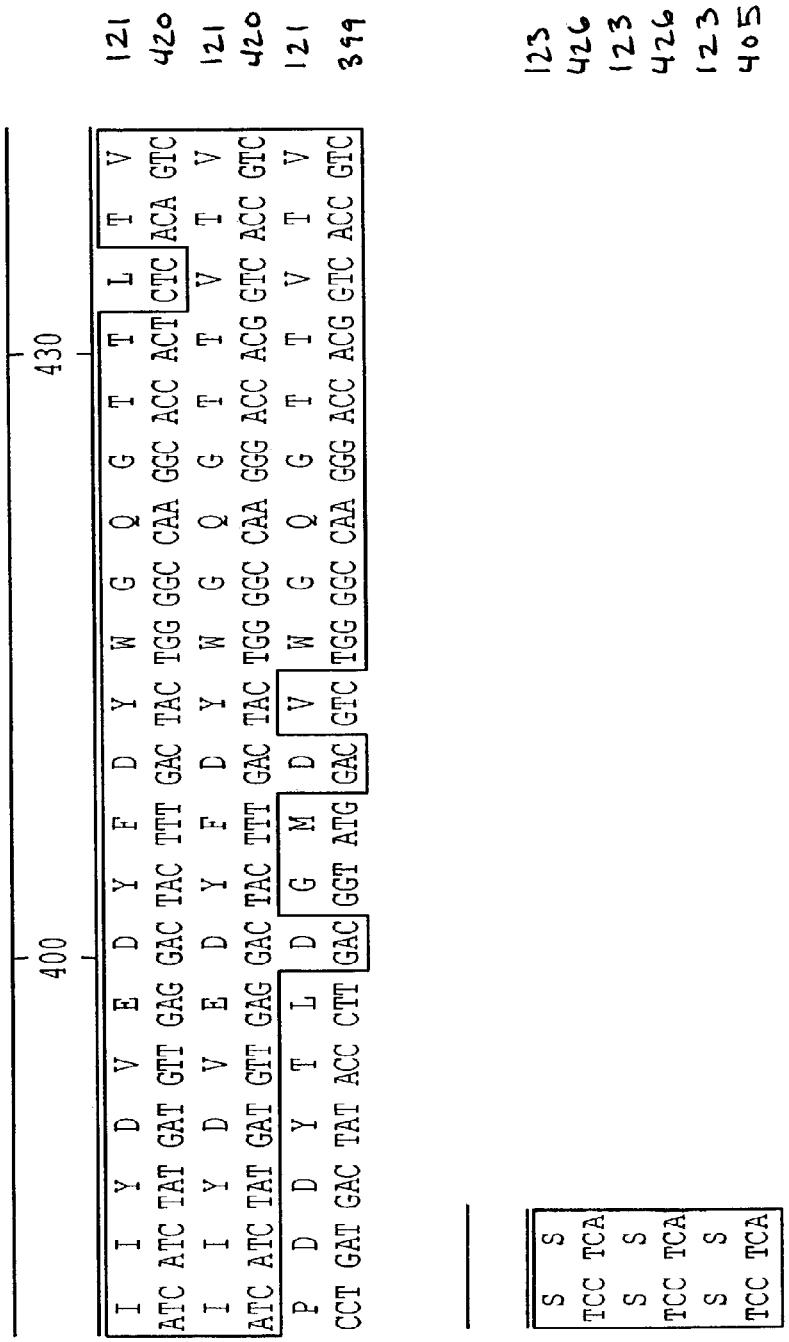

The amino acid alignment of the reshaped heavy chain V region is shown in FIG. 2. The choice for the acceptor framework (Kabid 000333) is from the same human subgroup as that which corresponds to the murine V region, has no unusual framework residues, and the CDRs belong to the same Chothia canonical groups. Structural modeling of the murine VH chain, in conjunction with the amino acid alignment of Kabid 000333 to the murine sequence dictates 9 back-mutations in version 1 (v1) of the reshaped heavy chain: L2V, V24F, G27F, I29L, I48L, G49A, V67L, V71K, & F78V (Kabat numbering). The back mutations are highlighted by asterisks in the amino-acid alignment shown in FIG. 2.

Of the 9 back mutations, 4 are dictated by the model because the residues are canonical residues (V24F, G27F, I29L, & V71K, indicated by solid filled boxes), i.e. framework residues which may contribute to antigen binding by virtue of proximity to CDR residues. There are no back mutations necessary in the next most important class of residues, the interface residues involved in VH–VL packing interactions (indicated by open boxes). The remaining 5 residues targeted for back mutation (L2V, I48L, G49A, V67L, F78V, Kabat numbering) all fall into the vernier class (indirect contribution to CDR conformation, dense stippled boxes in FIG. 2,).

Version 2 was designed to retain the lowest number of non-CDR murine residues. The L2V backmutation introduces a non-germline change (when using VH4–61 as the germline reference), and this backmutation is eliminated in version 2 of the heavy chain to restore it to germ line. The remaining 4 vernier class back mutations are also restored in version 2 of the heavy chain (I48L, G49A, V67L, F78V). Version 2 thus contain a total of 5 non-CDR murine residues (1 in VL, and 4 in VH). Version 3 was designed to restore 2 of the 5 vernier residues (I48L, & F78V), which the model indicates may be the more important vernier residues. Hence version 3 contains a total of 7 non CDR murine residues.

A summary of the changes incorporated into versions 1, 2 and 3 of humanized 12B4 are presented in Table 8.

TABLE 8

Summary of changes in humanized 12B4.v1

| Changes | VL (111 residues) | VH (123 residues) |
|---|---|---|
| Hu->Mu: Framework | 1/111 | 9/123 |
| CDR1 | 8/16 | 7/7 |
| CDR2 | 3/7 | 8/16 |
| CDR3 | 6/8 | 10/13 |
| Total Hu->Mu | 18/111 (16%) | 34/123 (28%, v2 = 23%) |
| Mu->Hu: Framework | 10/111 | 16/123 |
| Backmutation notes | 1. I2V: a canonical position. | 2. Canonical: V24F, G27F, I29L, & V71K |
| | | 3. Packing: none. |
| | | 4. Vernier: L2V*, I48L#, G49A*, V67L*, F78V# |
| Acceptor notes | 5. KABID 005036/ Genbank Acc#-x67904 | 8. KABID000333/ Genbank Acc#x54437 |
| | 6. CDRs from same canonical structural group as donor mouse; | 9. CDRs from same canonical structural group as donor mouse; |
| | 7. anti-cardiolipin/ss DNA autoantibody from SLE patient; | 10. rheumatoid factor mAb from RA patient |

*eliminate in v2 and v3;

eliminate in v2, restore in v3.

Tables 9 and 10 set forth Kabat numbering keys for the various light and heavy chains, respectively.

TABLE 9

Key to Kabat Numbering for Light Chain

| KAB # | # | TYPE | mouse 12B4 VL | HUM 12B4 VL | KABID 005036 | A19-Germ-line | Comment |
|---|---|---|---|---|---|---|---|
| 1 | 1 | FR1 | D | D | D | D | |
| 2 | 2 | | V | V | I | I | canonical - backmutate in v1, v2 and v3 |
| 3 | 3 | | L | V | V | V | |
| 4 | 4 | | M | M | M | M | |
| 5 | 5 | | T | T | T | T | |
| 6 | 6 | | Q | Q | Q | Q | |
| 7 | 7 | | T | S | S | S | |
| 8 | 8 | | P | P | P | P | |
| 9 | 9 | | L | L | L | L | |
| 10 | 10 | | S | S | S | S | |
| 11 | 11 | | L | L | L | L | |
| 12 | 12 | | P | P | P | P | |
| 13 | 13 | | V | V | V | V | |
| 14 | 14 | | S | T | T | T | |
| 15 | 15 | | L | P | P | P | |
| 16 | 16 | | G | G | G | G | |
| 17 | 17 | | D | E | E | E | |
| 18 | 18 | | Q | P | P | P | |
| 19 | 19 | | A | A | A | A | |
| 20 | 20 | | S | S | S | S | |
| 21 | 21 | | I | I | I | I | |
| 22 | 22 | | S | S | S | S | |
| 23 | 23 | | C | C | C | C | |
| 24 | 24 | CDR1 | R | R | R | R | |
| 25 | 25 | | S | S | S | S | |
| 26 | 26 | | S | S | S | S | |
| 27 | 27 | | Q | Q | Q | Q | |
| 27A | 28 | | N | N | S | S | |
| 27B | 29 | | I | I | L | L | |
| 27C | 30 | | V | V | L | L | |
| 27D | 31 | | H | H | H | H | |
| 27E | 32 | | S | S | R | S | |
| 28 | 33 | | N | N | Y | N | |
| 29 | 34 | | G | G | G | G | |
| 30 | 35 | | N | N | Y | Y | |
| 31 | 36 | | T | T | N | N | |
| 32 | 37 | | Y | Y | Y | Y | |
| 33 | 38 | | L | L | L | L | |
| 34 | 39 | | E | E | D | D | |
| 35 | 40 | FR2 | W | W | W | W | |
| 36 | 41 | | Y | Y | Y | Y | |
| 37 | 42 | | L | L | L | L | |
| 38 | 43 | | Q | Q | Q | Q | |
| 39 | 44 | | K | K | K | K | |
| 40 | 45 | | P | P | P | P | |
| 41 | 46 | | G | G | G | G | |
| 42 | 47 | | Q | Q | Q | Q | |
| 43 | 48 | | S | S | S | S | |
| 44 | 49 | | P | P | P | P | |
| 45 | 50 | | K | Q | Q | Q | |
| 46 | 51 | | L | L | L | L | |
| 47 | 52 | | L | L | L | L | |
| 48 | 53 | | I | I | I | I | |
| 49 | 54 | | Y | Y | Y | Y | |
| 50 | 55 | CDR2 | K | K | L | L | |
| 51 | 56 | | V | V | G | G | |
| 52 | 57 | | S | S | S | S | |
| 53 | 58 | | N | N | N | N | |
| 54 | 59 | | R | R | R | R | |
| 55 | 60 | | F | F | A | A | |
| 56 | 61 | | S | S | S | S | |
| 57 | 62 | FR3 | G | G | G | G | |
| 58 | 63 | | V | V | V | V | |
| 59 | 64 | | P | P | P | P | |
| 60 | 65 | | D | D | D | D | |
| 61 | 66 | | R | R | R | R | |
| 62 | 67 | | F | F | F | F | |
| 63 | 68 | | S | S | S | S | |
| 64 | 69 | | G | G | G | G | |
| 65 | 70 | | S | S | S | S | |
| 66 | 71 | | G | G | G | G | |
| 67 | 72 | | S | S | S | S | |

TABLE 9-continued

Key to Kabat Numbering for Light Chain

| KAB # | # | TYPE | mouse 12B4 VL | HUM 12B4 VL | KABID 005036 | A19-Germline | Comment |
|---|---|---|---|---|---|---|---|
| 68 | 73 | | G | G | G | G | |
| 69 | 74 | | T | T | T | T | |
| 70 | 75 | | D | D | D | D | |
| 71 | 76 | | F | F | F | F | |
| 72 | 77 | | T | T | T | T | |
| 73 | 78 | | L | L | L | L | |
| 74 | 79 | | K | K | K | K | |
| 75 | 80 | | I | I | I | I | |
| 76 | 81 | | S | S | S | S | |
| 77 | 82 | | R | R | R | R | |
| 78 | 83 | | V | V | V | V | |
| 79 | 84 | | E | E | E | E | |
| 80 | 85 | | A | A | A | A | |
| 81 | 86 | | E | E | E | E | |
| 82 | 87 | | D | D | D | D | |
| 83 | 88 | | L | V | V | V | |
| 84 | 89 | | G | G | G | G | |
| 85 | 90 | | V | V | V | V | |
| 86 | 91 | | Y | Y | Y | Y | |
| 87 | 92 | | Y | Y | Y | Y | |
| 88 | 93 | | C | C | C | C | |
| 89 | 94 | CDR3 | F | F | M | M | |
| 90 | 95 | | Q | Q | Q | Q | |
| 91 | 96 | | G | G | A | A | |
| 92 | 97 | | S | S | L | L | |
| 93 | 98 | | H | H | Q | Q | |
| 94 | 99 | | V | V | T | T | |
| 95 | 100 | | P | P | P | P | |
| 96 | 101 | | L | L | Y | | |
| 97 | 102 | | T | T | T | | |
| 98 | 103 | FR4 | F | F | F | | |
| 99 | 104 | | G | G | G | | |
| 100 | 105 | | A | Q | Q | | |
| 101 | 106 | | G | G | G | | |
| 102 | 107 | | T | T | T | | |
| 103 | 108 | | K | K | K | | |
| 104 | 109 | | L | L | L | | |
| 105 | 110 | | E | E | E | | |
| 106 | 111 | | L | I | I | | |
| 106A | 112 | | K | K | K | | |

TABLE 10

Key to Kabat Numbering for Heavy Chain

| KAB # | # | TYPE | Mouse 12B4 VH | HUM 12B4 VHv1 | KABID 000333 | VH4-39 Germline | VH4-61 Germline | Comment |
|---|---|---|---|---|---|---|---|---|
| 1 | 1 | FR1 | Q | Q | Q | Q | Q | |
| 2 | 2 | | V | V | L | L | V | vernier - backmutate in v1 only |
| 3 | 3 | | T | Q | Q | Q | Q | |
| 4 | 4 | | L | L | L | L | L | |
| 5 | 5 | | K | Q | Q | Q | Q | |
| 6 | 6 | | E | E | E | E | E | |
| 7 | 7 | | S | S | S | S | S | |
| 8 | 8 | | G | G | G | G | G | |
| 9 | 9 | | P | P | P | P | P | |
| 10 | 10 | | G | G | G | G | G | |
| 11 | 11 | | I | L | L | L | L | |
| 12 | 12 | | L | V | V | V | V | |
| 13 | 13 | | Q | K | K | K | K | |
| 14 | 14 | | P | P | P | P | P | |
| 15 | 15 | | S | S | S | S | S | |
| 16 | 16 | | Q | E | E | E | E | |
| 17 | 17 | | T | T | T | T | T | |
| 18 | 18 | | L | L | L | L | L | |
| 19 | 19 | | S | S | S | S | S | |
| 20 | 20 | | L | L | L | L | L | |

TABLE 10-continued

Key to Kabat Numbering for Heavy Chain

| KAB # | # | TYPE | Mouse 12B4 VH | HUM 12B4 VHv1 | KABID 000333 | VH4-39 Germ-line | VH4-61 Germ-line | Comment |
|---|---|---|---|---|---|---|---|---|
| 21 | 21 | | T | T | T | T | T | |
| 22 | 22 | | C | C | C | C | C | |
| 23 | 23 | | S | T | T | T | T | |
| 24 | 24 | | F | F | V | V | V | canonical - backmutate in v1, v2 and v3 |
| 25 | 25 | | S | S | S | S | S | |
| 26 | 26 | | G | G | G | G | G | |
| 27 | 27 | | F | F | G | G | G | canonical - backmutate in v1, v2 and v3 |
| 28 | 28 | | S | S | S | S | S | |
| 29 | 29 | | L | L | I | I | V | canonical - backmutate in v1, v2 and v3 |
| 30 | 30 | | S | S | S | S | S | |
| 31 | 31 | CDR1 | T | T | R | S | S | |
| 32 | 32 | | N | N | G | S | G | |
| 33 | 33 | | G | G | S | S | G | |
| 34 | 34 | | M | M | H | Y | Y | |
| 35 | 35 | | G | G | Y | Y | Y | |
| 35A | 36 | | V | V | W | W | W | |
| 35B | 37 | | S | S | G | G | S | |
| 36 | 38 | FR2 | W | W | W | W | W | |
| 37 | 39 | | I | I | I | I | I | |
| 38 | 40 | | R | R | R | R | R | |
| 39 | 41 | | Q | Q | Q | Q | Q | |
| 40 | 42 | | P | P | P | P | P | |
| 41 | 43 | | S | P | P | P | P | |
| 42 | 44 | | G | G | G | G | G | |
| 43 | 45 | | K | K | K | K | K | |
| 44 | 46 | | G | G | G | G | G | |
| 45 | 47 | | L | L | L | L | L | |
| 46 | 48 | | E | E | E | E | E | |
| 47 | 49 | | W | W | W | W | W | |
| 48 | 50 | | L | L | I | I | I | vernier - backmutate in v1 and v3 only |
| 49 | 51 | | A | A | G | G | G | vernier - backmutate in v1 only |
| 50 | 52 | CDR2 | H | H | S | S | Y | |
| 51 | 53 | | I | I | I | I | I | |
| 52 | 54 | | Y | Y | Y | Y | Y | |
| 53 | 55 | | W | W | Y | Y | Y | |
| 54 | 56 | | D | D | S | S | S | |
| 55 | 57 | | E | E | G | G | G | |
| 56 | 58 | | D | D | N | S | S | |
| 57 | 59 | | K | K | T | T | T | |
| 58 | 60 | | R | R | Y | Y | N | |
| 59 | 61 | | Y | Y | F | Y | Y | |
| 60 | 62 | | N | N | N | N | N | |
| 61 | 63 | | P | P | P | P | P | |
| 62 | 64 | | S | S | S | S | S | |
| 63 | 65 | | L | L | L | L | L | |
| 64 | 66 | | K | K | K | K | K | |
| 65 | 67 | | S | S | S | S | S | |
| 66 | 68 | FR3 | R | R | R | R | R | |
| 67 | 69 | | L | L | V | V | V | vernier - backmutate in v1 only |
| 68 | 70 | | T | T | T | T | T | |
| 69 | 71 | | I | I | I | I | I | |
| 70 | 72 | | S | S | S | S | S | |
| 71 | 73 | | K | K | V | V | V | canonical - backmutate in v1, v2 and v3 |
| 72 | 74 | | D | D | D | D | D | |
| 73 | 75 | | T | T | T | T | T | |
| 74 | 76 | | S | S | S | S | S | |
| 75 | 77 | | N | K | K | K | K | |
| 76 | 78 | | N | N | N | N | N | |
| 77 | 79 | | Q | Q | Q | Q | Q | |
| 78 | 80 | | V | V | F | F | F | vernier - backmutate in v1 and v3 |
| 79 | 81 | | F | S | S | S | S | |
| 80 | 82 | | L | L | L | L | L | |
| 81 | 83 | | K | K | K | K | K | |
| 82 | 84 | | I | L | L | L | L | |
| 82A | 85 | | T | S | S | S | S | |

TABLE 10-continued

Key to Kabat Numbering for Heavy Chain

| KAB # | # | TYPE | Mouse 12B4 VH | HUM 12B4 VHv1 | KABID 000333 | VH4-39 Germline | VH4-61 Germline | Comment |
|---|---|---|---|---|---|---|---|---|
| 82B | 86 | | N | S | S | S | S | |
| 82C | 87 | | V | V | V | V | V | |
| 83 | 88 | | D | T | T | T | T | |
| 84 | 89 | | T | A | A | A | A | |
| 85 | 90 | | A | A | A | A | A | |
| 86 | 91 | | D | D | D | D | D | |
| 87 | 92 | | T | T | T | T | T | |
| 88 | 93 | | A | A | A | A | A | |
| 89 | 94 | | T | V | V | V | V | |
| 90 | 95 | | Y | Y | Y | Y | Y | |
| 91 | 96 | | Y | Y | Y | Y | Y | |
| 92 | 97 | | C | C | C | C | C | |
| 93 | 98 | | A | A | A | A | A | |
| 94 | 99 | | R | R | R | R | R | |
| 95 | 100 | CDR3 | R | R | L | | | |
| 95A | — | | — | — | G | | | |
| 96 | 101 | | R | R | P | | | |
| 97 | 102 | | I | I | D | | | |
| 98 | 103 | | I | I | D | | | |
| 99 | 104 | | Y | Y | Y | | | |
| 100 | 105 | | D | D | T | | | |
| 100A | 106 | | V | V | L | | | |
| 100B | 107 | | E | E | D | | | |
| 100C | 108 | | D | D | G | | | |
| 100D | 109 | | Y | Y | — | | | |
| 100E | 110 | | F | F | M | | | |
| 101 | 111 | | D | D | D | | | |
| 102 | 112 | | Y | Y | V | | | |
| 103 | 113 | FR4 | W | W | W | | | |
| 104 | 114 | | G | G | G | | | |
| 105 | 115 | | Q | Q | Q | | | |
| 106 | 116 | | G | G | G | | | |
| 107 | 117 | | T | T | T | | | |
| 108 | 118 | | T | T | T | | | |
| 109 | 119 | | L | V | V | | | |
| 110 | 120 | | T | T | T | | | |
| 111 | 121 | | V | V | V | | | |
| 112 | 122 | | S | S | S | | | |
| 113 | 123 | | S | S | S | | | |

The humanized antibodies preferably exhibit a specific binding affinity for Aβ of at least $10^7$, $10^8$, $10^9$ or $10^{10}$ M$^{-1}$. Usually the upper limit of binding affinity of the humanized antibodies for AP is within a factor of three, four or five of that of 12B4 (i.e., ~$10^9$ M$^{-1}$). Often the lower limit of binding affinity is also within a factor of three, four or five of that of 12B4.

Figure 9A:
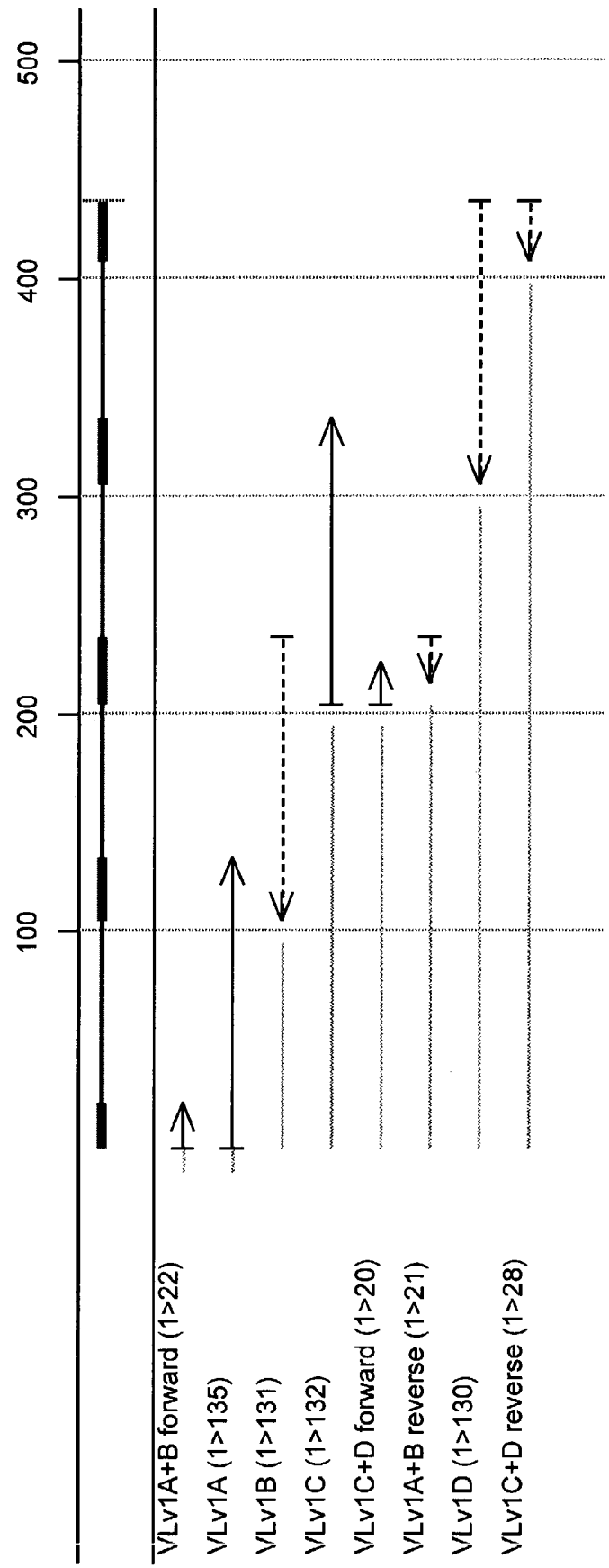
FIG. 9A depicts the assembly of the VL regions.
Figure 9B:
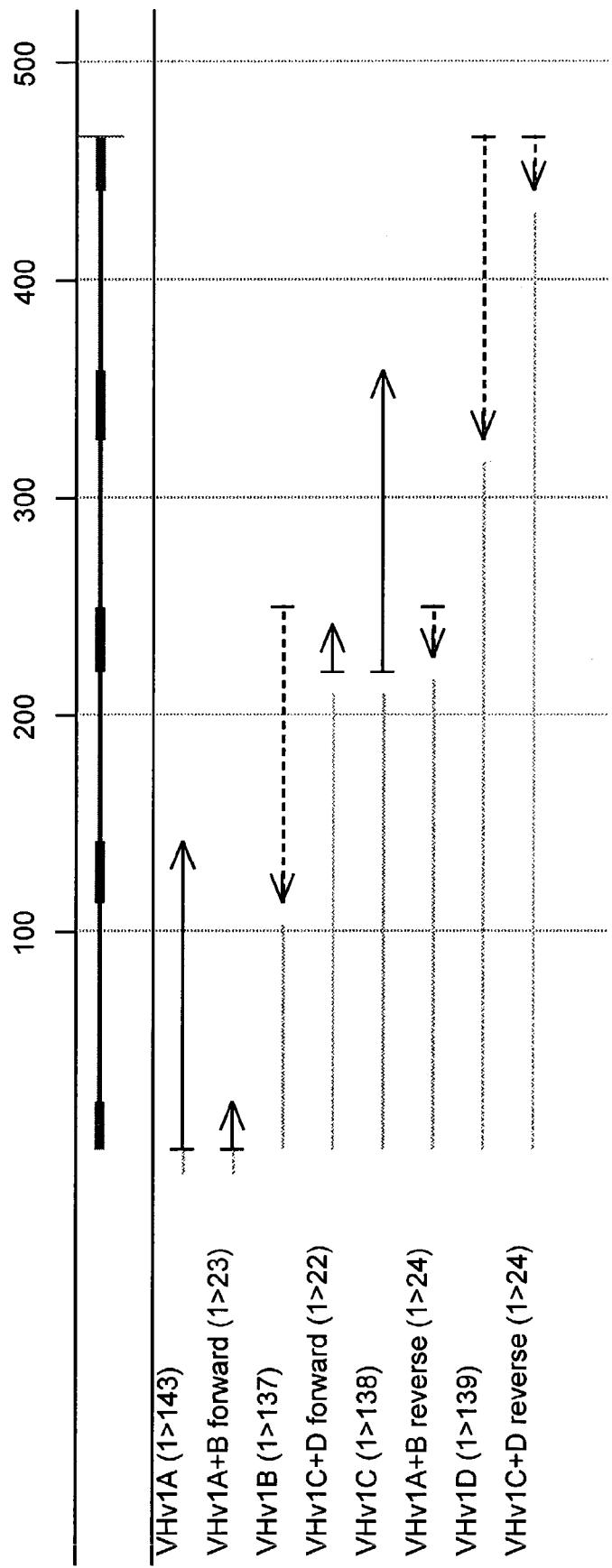
FIG. 9B depicts the assembly of the VH regions.

Assembly and Expression of Humanized 12B4 VH and VL, Version 1 FIG. 9a is a schematic representation of the strategy for PCR mediated assembly of humanized VL.v1. FIG. 9b is a schematic representation of the strategy for PCR mediated assembly of humanized VH.v1. Table 11 sets forth primers used for the PCR-mediated assembly of 12B4v1.

TABLE 11

Synthetic oligonucleotides used in PCR mediated assembly of humanized 12B4 V regions, v1

| DNA # | Size | Coding strand? | Sequence | Comments |
|---|---|---|---|---|
| 4881 | 135 | Yes | gagattaagcttgccgccaccATGAGGCT CCCTGCTCAGCTCCTGGGGCTGCTAATGC TCTGGGTCTCTGGATCCAGTGGGGATGTT GTGATGACTCAGTCTCCACTCTCCCTGCC CGTCACCCCTGGAGAGCCG SEQ ID NO: 13 | hum12B4 VLv1A primer synthesized by Oligos etc. nts 1 > 115 12B4VLv1.cons, sense strand. Adds HindIII site + Kozak consensus. |
| 4882 | 131 | No | AGGAGCTGTGGAGACTGCCCTGGCTTCTG CAGGTACCATTCCAAATAGGTGTTTCCAT TACTATGAACAATCTTCTGACTAGACCTG | hum12B4 VLv1B primer synthesized by Oligos etc. Reverse Complement DNA |

TABLE 11-continued

Synthetic oligonucleotides used in PCR mediated assembly of humanized 12B4 V regions, v1

| DNA # | Size | Coding strand? | Sequence | Comments |
|---|---|---|---|---|
| | | | CAGGAGATGGAGGCCGGCTCTCCAGGGGT GACGGGCAGGGAGAG SEQ ID NO: 14 | Sequence 12B4VLv1.cons (85, 215) |
| 4883 | 132 | Yes | TGCAGAAGCCAGGGCAGTCTCCACAGCTC CTGATCTACAAAGTTTCCAACCGATTTTC TGGGGTCCCTGACAGGTTCAGTGGCAGTG GATCAGCCACAGATTTTACACTGAAAATC AGCAGAGTGGAGGCTG SEQ ID NO: 15 | hum12B4 VLv1C primer synthesized by Oligos etc. nts 185 > 316 12B4VLv1.cons, sense strand. |
| 4884 | 130 | No | tgatatggatccactcacGTTTGATCTCC AGCTTGGTCCCTGACCGAACGTGAGCGG AACATGTGAACCTTGAAAGCAGTAATAAA CCCCAACATCCTCAGCCTCCACTCTGCTG ATTTTCAGTGTAAA SEQ ID NO: 16 | hum12B4 VLv1D primer synthesized by Oligos etc. Reverse Complement DNA Sequence 12B4VLv1.cons (286, 397) adds splice donor + BamHI site. |
| 4885 | 143 | Yes | gagataaagcttgccgccaccATGAAGCA CCTGTGGTTCTTCCTCCTGCTGGTGGCAG CTCCCAGATGGGTCCTGTCCCAGGTGCAG CTGCAGCAGTCGGGCCCAGGACTGCTGAA GCCTTCGCAGACCCTGTCCCTCACCTG SEQ ID NO: 17 | hum12B4 VHv1A primer synthesized by Oligos etc. 12B4VHv1.cons nts 1–122, adds Kozak consensus, and HindIII site |
| 4886 | 137 | No | TCCTCATCCCAATAGATGTGTGCCAGCCA CTCCAGTCCCTTCCCTGGGGGCTGCCGGA TCCAGCTCACACCCATACCATTAGTGCTC AGGGAAAAACCAGAGAAAGTGCAGGTGAG GGACAGGGTCTCCGAAGGCTT SEQ ID NO: 18 | hum12B4 VHv1B primer synthesized by Oligos etc. Reverse Complement DNA Sequence 12B4VHv1.cons (94, 230) |
| 4887 | 138 | Yes | GTGGCTGGCACACATCTATTGGGATGAGG ACAAGCGCTATAACCCATCCCTCAAGAGT CGACTCACCATATCAAAGGACACGTCCAA GAACCAGGTATCCCTGAAGCTGAGCTCTG TGACCGCTGCAGACACGGCCGT SEQ ID NO: 19 | hum12B4 VHv1C primer synthesized by Oligos etc. 12B4 VHv1.cons nts201–338 |
| 4888 | 139 | No | tcatatggatccactcacCTGAGGAGACG GTGACCGTGGTCCCTTGGCCCCAGTAGTC AAAGTAGTCCTAACATCATAGATGATCC TCCTTCTCGCACAGTAATACACGGCCGTG TCTGCAGCGGTCACAGAGCTCAG SEQ ID NO: 20 | hum12B4 VHv1D primer synthesized by Oligos etc. Reverse Complement DNA Sequence 12B4VHvT.cons (307, 427) adds splice donor + BamHI site to 3' end. |
| 4889 | 22 | Yes | gag att aag ctt gcc gcc acc A SEQ ID NO: 21 | hum 12B4 VLv1, A + B For primer % A + T = 45.45 [10]; % C + G = 54.55 [12] Davis, Botstein, Roth Melting Temp C. 64.54 |
| 4890 | 21 | No | AGG AGC TGT GGA GAC TGC CCT SEQ ID NO: 22 | hum 12B4 VLv1, A + B bak primer % A + T = 38.10 [8]; % C + G = 61.90 [13] Davis, Botstein, Roth Melting Temp C. 66.47 |
| 4891 | 20 | Yes | TGC AGA AGC CAG GGC AGT CT SEQ ID NO: 23 | hum 12B4 VLv1, C + D For primer % A + T = 40.00 [8]; % C + G = 60.00 [12] Davis, Botstein, Roth Melting Temp C. 64.50 |
| 4892 | 28 | No | tga tat gga tcc act cac GTT TGA TCT C SEQ ID NO: 24 | hum 12B4 VLv1, C + D bak primer % A + T = 57.14 [16]; % C + G = 42.86 [12] Davis, Botstein, Roth Melting Temp C. 64.61 |

TABLE 11-continued

Synthetic oligonucleotides used in PCR mediated assembly of humanized 12B4 V regions, v1

| DNA # | Size | Coding strand? | Sequence | Comments |
|---|---|---|---|---|
| 4893 | 23 | Yes | gag ata aag ctt gcc gcc acc AT<br>SEQ ID NO: 25 | hum 12B4 VHv1, A + B For primer % A + T = 47.83 [11]; % C + G = 52.17 [12] Davis, Botstein, Roth Melting Temp C. 64.55 |
| 4894 | 24 | No | TCC TCA TCC CAA TAG ATG TGT GCC<br>SEQ ID NO: 26 | hum 12B4 VHv1, A + B bak primer % A + T = 50.00 [12]; % C + G = 50.00 [12] Davis, Botstein, Roth Melting Temp C. 64.57 |
| 4895 | 22 | Yes | GTG GCT GGC ACA CAT CTA TTG G<br>SEQ ID NO: 27 | hum 12B4 VHv1, C + D For primer % A + T = 45.45 [10]; % C + G = 54.55 [12] Davis, Botstein, Roth Melting Temp C. 64.54 |
| 4896 | 24 | No | tca tat gga tcc act cac CTG AGG<br>SEQ ID NO: 28 | hum 12B4 VHv1, C + D For primer % A + T = 50.00 [12]; % C + G = 50.00 [12] Davis, Botstein, Roth Melting Temp C. 64.57 |

Equimolar rations of VHv1A+VHv1B and VHv1C+VHv1D synthetic fragments were annealed as pairs, in separate reaction tubes using standard procedures. The A+B annealing reaction was assembled using PCR with primers A+B for and A+B back at 60° C. annealing, 25 cycles (for=forward and back=backwards, alternatively, rev or reverse). Likewise the C+D annealing reaction was assembled using PCR primers C+Dfor and C+Dback under identical conditions. The PCR-assembled 5' A+B half, and 3'C+D half, were gel purified for a final PCR-mediated assembly. Full V region assembly was effected by mixing the A+B assembled 5' half with the C+D 3' half of the V-region, annealing, and extending by PCR using VHv1A+B for primer, and VHv1C+D back primer. The full length VH and VL regions assembled in this manner were gel purified, and cloned into pCRScript for DNA sequence verification.

The nucleotide sequences of humanized 12B4VL (version 1) (SEQ ID NO:5) and 12B4VH (version 1) (SEQ ID NO: 7) are listed below as Tables 12 and 13, respectively.

TABLE 12

Nucleotide sequence of humanized 12B4VLv1.

ATGAGGCTCCCTGCTCAGCTCCTGGGGCTGCTAATGCTCTGGGTCTCTGG

ATCCAGTGGGGATGTTGTGATGACTCAGTCTCCACTCTCCCTGCCCGTCA

CCCCTGGAGAGCCGGCCTCCATCTCCTGCAGGTCTAGTCAGAACATTGTT

CATAGTAATGGAAACACCTATTTGGAATGGTACCTGCAGAAGCCAGGGCA

GTCTCCACAGCTCCTGATCTACAAACTTTCCAACCGATTTTCTGGGGTCC

CTGACAGGTTCAGTGGCAGTGGATCAGGCACAGATTTTACACTGAAAATC

TABLE 12-continued

Nucleotide sequence of humanized 12B4VLv1.

AGCAGAGTGGAGGCTGAGGATGTTGGGGTTTATTACTGCTTTCAAGGTTC

ACATGTTCCGCTCACGTTCGGTCAGGGGACCAAGCTGGAGATCAAAC

TABLE 13

Nucleotide sequence of humanized 12B4VHv1

ATGAAGCACCTGTGGTTCTTCCTCCTGCTGGTGGCAGCTCCCAGATGGGT

CCTGTCCCAGGTGCAGCTGCAGGAGTCGGGCCCAGGACTGGTGAAGCCTT

CGGAGACCCTGTCCCTCACCTGCACTTTCTCTGGTTTTTCCCTGAGCACT

AATGGTATGGGTGTGAGCTGGATCCGGCAGCCCCCAGGGAAGGGACTGGA

GTGGCTGGCACACATCTATTGGGATGAGGACAAGCGCTATAACCCATCCC

TCAAGAGTCGACTCACCATATCAAAGGACACGTCCAAGAACCAGGTATCC

CTGAAGCTGAGCTCTGTGACCGCTGCAGACACGGCCGTGTATTACTGTGC

GAGAAGGAGGATCATCTATGATGTTGAGGACTACTTTGACTACTGGGGCC

AAGGGACCACGGTCACCGTCTCCTCAG

B. Humanized 12B4 Version 2 Antibody

A second version of humanized 12B4 was created having each of the substitutions indicated for version 1, except for the L→V substitution at residue 2, the I→L substitution at residue 48, the G→A substitution at residue 49, the V→L substitution at residue 67 and the F→V substitution at residue 78. The nucleotide sequences of humanized 12B4 version 2 light and heavy chains are set forth as SEQ ID NOs: 9 and 11, respectively. The nucleotide sequences of humanized 3D6 version 2 light and heavy chains are set forth as SEQ ID NOs: 5 and 9, respectively. The amino acid sequences of humanized 12B4 version 2 light and heavy chains are set forth as SEQ ID NOs: 6 and 10, respectively.

C. Humanized 12B4 Version 3 Antibody

A third version of humanized 12B4 was created having each of the substitutions indicated for version 1, except for the L→V substitution at residue 2, the G→A substitution at residue 49 and the V→L substitution at residue 67. The nucleotide sequences of humanized 12B4 version 3 light and heavy chains are set forth as SEQ ID NOs: 5 and 11, respectively. The amino acid sequences of humanized 3D6 version 3 light and heavy chains are set forth as SEQ ID NOs: 2 and 12, respectively.

Example VI

Prevention and Treatment of Human Subjects

A single-dose phase I trial is performed to determine safety in humans. A therapeutic agent is administered in increasing dosages to different patients starting from about 0.01 the level of presumed efficacy, and increasing by a factor of three until a level of about 10 times the effective mouse dosage is reached.

A phase II trial is performed to determine therapeutic efficacy. Patients with early to mid Alzheimer's Disease defined using Alzheimer's disease and Related Disorders Association (ADRDA) criteria for probable AD are selected. Suitable patients score in the 12–26 range on the Mini-Mental State Exam (MMSE). Other selection criteria are that patients are likely to survive the duration of the study and lack complicating issues such as use of concomitant medications that may interfere. Baseline evaluations of patient function are made using classic psychometric measures, such as the MMSE, and the ADAS, which is a comprehensive scale for evaluating patients with Alzheimer's Disease status and function. These psychometric scales provide a measure of progression of the Alzheimer's condition. Suitable qualitative life scales can also be used to monitor treatment. Disease progression can also be monitored by MRI. Blood profiles of patients can also be monitored including assays of immunogen-specific antibodies and T-cells responses.

Following baseline measurements, patients begin receiving treatment. They are randomized and treated with either therapeutic agent or placebo in a blinded fashion. Patients are monitored at least every six months. Efficacy is determined by a significant reduction in progression of a treatment group relative to a placebo group.

A second phase II trial is performed to evaluate conversion of patients from non-Alzheimer's Disease early memory loss, sometimes referred to as age-associated memory impairment (AAMI) or mild cognitive impairment (MCI), to probable Alzheimer's disease as defined as by ADRDA criteria. Patients with high risk for conversion to Alzheimer's Disease are selected from a non-clinical population by screening reference populations for early signs of memory loss or other difficulties associated with pre-Alzheimer's symptomatology, a family history of Alzheimer's Disease, genetic risk factors, age, sex, and other features found to predict high-risk for Alzheimer's Disease. Baseline scores on suitable metrics including the MMSE and the ADAS together with other metrics designed to evaluate a more normal population are collected. These patient populations are divided into suitable groups with placebo comparison against dosing alternatives with the agent. These patient populations are followed at intervals of about six months, and the endpoint for each patient is whether or not he or she converts to probable Alzheimer's Disease as defined by ADRDA criteria at the end of the observation.

Although the foregoing invention has been described in detail for purposes of clarity of understanding, it will be obvious that certain modifications may be practiced within the scope of the appended claims. All publications and patent documents cited herein, as well as text appearing in the figures and sequence listing, are hereby incorporated by reference in their entirety for all purposes to the same extent as if each were so individually denoted.

From the foregoing it will be apparent that the invention provides for a number of uses. For example, the invention provides for the use of any of the antibodies to Aβ described above in the treatment, prophylaxis or diagnosis of amyloidogenic disease, or in the manufacture of a medicament or diagnostic composition for use in the same.

We claim:

1. A humanized immunoglobulin which specifically binds beta amyloid peptide (Aβ), or antigen-binding fragment thereof, the humanized immunoglobulin comprising:

(i) a light chain comprising three complementarity determining regions (CDRs) from the 12B4 immunoglobulin light chain variable region sequence set forth as SEQ ID NO:2, and a variable framework region from a human acceptor immunoglobulin light chain; and (ii) a heavy chain comprising three complementarity determining regions (CDRs) from the 12B4 immunoglobulin heavy chain variable region sequence set forth as SEQ ID NO:4, and a variable framework region from a human acceptor immunoglobulin heavy chain, provided that at least one framework residue in the light or heavy chain is substituted with the corresponding amino acid residue from the mouse 12B4 light or heavy chain variable region sequence, wherein the framework residue is selected from the group consisting of:

(a) a residue that non-covalently binds antigen directly;
   (b) a residue adjacent to a CDR;
   (c) a CDR-interacting residue; and
   (d) a residue participating in the VL–VH interface.

2. A humanized immunoglobulin which specifically binds beta amyloid peptide (Aβ), or antigen-binding fragment thereof, the humanized immunoglobulin comprising:

(i) a light chain comprising three complementarity determining regions (CDRs) from the 12B4 immunoglobulin light chain variable region sequence set forth as SEQ ID NO:2, and a variable framework region from a human acceptor immunoglobulin light chain; and (ii) a heavy chain comprising three complementarity determining regions (CDRs) from the 12B4 immunoglobulin heavy chain variable region sequence set forth as SEQ ID NO:4, and a variable framework region from a human acceptor immunoglobulin heavy chain, provided that at least one framework residue in both the light and heavy chain is substituted with the corresponding amino acid residue from the mouse 12B4 light or heavy chain variable region sequence, wherein the framework residue is selected from the group consisting of:

(a) a residue that non-covalently binds antigen directly;
(b) a residue adjacent to a CDR;
(c) a CDR-interacting residue; and
(d) a residue participating in the VL–VH interface.

3. The humanized immunoglobulin or antigen-binding fragment of claim 1 or 2, wherein the framework residue is a CDR-interacting residue identified by modeling the 12B4 light chain based on the solved structure of a murine immunoglobulin light chain that shares at least 70% sequence identity with the 12B4 light chain.

4. The humanized immunoglobulin or antigen-binding fragment of claim 1 or 2, wherein the framework residue is a CDR-interacting residue identified by modeling the 12B4 light chain based on the solved structure of a murine immunoglobulin light chain that shares at least 80% sequence identity with the 12B4 light chain.

5. The humanized immunoglobulin or antigen-binding fragment of claim 1 or 2, wherein the framework residue is a CDR-interacting residue identified by modeling the 12B4 light chain based on the solved structure of a murine immunoglobulin light chain that shares at least 90% sequence identity with the 12B4 light chain.

6. The humanized immunoglobulin or antigen-binding fragment of claim 1 or 2, wherein the framework residue is a CDR-interacting residue identified by modeling the 12B4 heavy chain based on the solved structure of a murine immunoglobulin heavy chain that shares at least 70% sequence identity with the 12B4 heavy chain.

7. The humanized immunoglobulin or antigen-binding fragment of claim 1 or 2, wherein the framework residue is a CDR-interacting residue identified by modeling the 12B4 heavy chain based on the solved structure of a murine immunoglobulin heavy chain that shares at least 80% sequence identity with the 12B4 heavy chain.

8. The humanized immunoglobulin or antigen-binding fragment of claim 1 or 2, wherein the framework residue is a CDR-interacting residue identified by modeling the 12B4 heavy chain based on the solved structure of a murine immunoglobulin heavy chain that shares at least 90% sequence identity with the 12B4 heavy chain.

9. A humanized immunoglobulin which specifically binds beta amyloid peptide (Aβ), or antigen-binding fragment thereof, the humanized immunoglobulin comprising:
(i) a light chain comprising three complementarity determining regions (CDRs) from the 12B4 immunoglobulin light chain variable region sequence set forth as SEQ ID NO:2, and a variable framework region from a human acceptor immunoglobulin light chain sequence; and
(ii) a heavy chain comprising three complementarity determining regions (CDRs) from the 12B4 immunoglobulin heavy chain variable region sequence set forth as SEQ ID NO:4, and a variable framework region from a human acceptor immunoglobulin heavy chain sequence,
provided that at least one framework residue in the light or heavy chain is substituted with the corresponding amino acid residue from the mouse 12B4 light or heavy chain variable region sequence, wherein the framework residue is a residue capable of affecting the light or heavy chain variable region conformation or function as identified by analysis of a three-dimensional model of the variable region.

10. A humanized immunoglobulin which specifically binds beta amyloid peptide (Aβ), or antigen-binding fragment thereof, the humanized immunoglobulin comprising:
(i) a light chain comprising three complementarity determining regions (CDRs) from the 12B4 immunoglobulin light chain variable region sequence set forth as SEQ ID NO:2, and a variable framework region from a human acceptor immunoglobulin light chain sequence; and
(ii) a heavy chain comprising three complementarity determining regions (CDRs) from the 12B4 immunoglobulin heavy chain variable region sequence set forth as SEQ ID NO:4, and a variable framework region from a human acceptor immunoglobulin heavy chain sequence,
provided that at least one framework residue in both the light and heavy chain is substituted with the corresponding amino acid residue from the mouse 12B4 light or heavy chain variable region sequence, wherein the framework residue is a residue capable of affecting the light or heavy chain variable region conformation or function as identified by analysis of a three-dimensional model of the variable region.

11. The humanized immunoglobulin or antigen-binding fragment of claim 9 or 10, wherein the framework residue in the light chain is selected from the group consisting of a residue capable of interacting with antigen, a residue proximal to the antigen binding site, a residue capable of interacting with a CDR, a residue adjacent to a CDR, a residue within 6 Å of a CDR residue, a canonical residue, a vernier zone residue, an interchain packing residue, a rare residue, and a glycosylation site residue on the surface of the three-dimensional model.

12. The humanized immunoglobulin or antigen-binding fragment of claim 9 or 10, wherein the framework residue in the heavy chain is selected from the group consisting of a residue capable of interacting with antigen, a residue proximal to the antigen binding site, a residue capable of interacting with a CDR, a residue adjacent to a CDR, a residue within 6 Å of a CDR residue, a canonical residue, a vernier zone residue, an interchain packing residue, a rare residue, and a glycosylation site residue on the surface of the three-dimensional model.

13. The humanized immunoglobulin or antigen-binding fragment of claim 9 or 10, wherein the framework residue in the light chain is identified by modeling the 12B4 light chain based on the solved structure of a murine immunoglobulin light chain that shares at least 70% sequence identity with the 12B4 light chain.

14. The humanized immunoglobulin or antigen-binding fragment of claim 9 or 10, wherein the framework residue in the light chain is identified by modeling the 12B4 light chain based on the solved structure of a murine immunoglobulin light chain that shares at least 80% sequence identity with the 12B4 light chain.

15. The humanized immunoglobulin or antigen-binding fragment of claim 9 or 10, wherein the framework residue in the light chain is identified by modeling the 12B4 light chain based on the solved structure of a murine immunoglobulin light chain that shares at least 90% sequence identity with the 12B4 light chain.

16. The humanized immunoglobulin or antigen-binding fragment of claim 9 or 10, wherein the framework residue in the heavy chain is identified by modeling the 12B4 heavy chain based on the solved structure of a murine immunoglobulin heavy chain that shares at least 70% sequence identity with the 12B4 heavy chain.

17. The humanized immunoglobulin or antigen-binding fragment of claim 9 or 10, wherein the framework residue in the heavy chain is identified by modeling the 12B4 heavy chain based on the solved structure of a murine immunoglobulin heavy chain that shares at least 80% sequence identity with the 12B4 heavy chain.

18. The humanized immunoglobulin or antigen-binding fragment of claim 9 or 10, wherein the framework residue in the heavy chain is identified by modeling the 12B4 heavy chain based on the solved structure of a murine immunoglobulin heavy chain that shares at least 90% sequence identity with the 12B4 heavy chain.

19. A humanized immunoglobulin which specifically binds beta amyloid peptide (Aβ), or antigen-binding fragment thereof, the humanized immunoglobulin comprising a light chain comprising three complementarity determining regions (CDRs) from the monoclonal antibody 12B4 light chain variable region sequence set forth as SEQ ID NO:2 and variable region framework residue L2 (Kabat numbering convention) from the monoclonal antibody 12B4 light chain, wherein the remainder of the light chain is from a human immunoglobulin, and a heavy chain comprising three complementarity determining regions (CDRs) from the monoclonal antibody 12B4 heavy chain variable sequence set forth as SEQ ID NO:4.

20. A humanized immunoglobulin which specifically binds beta amyloid peptide (Aβ), or antigen-binding fragment thereof, the humanized immunoglobulin or antigen-binding fragment comprising a light chain comprising three complementarity determining regions (CDRs) from the monoclonal antibody 12B4 light chain variable region sequence set forth as SEQ ID NO:2, and a heavy chain comprising three complementarity determining regions (CDRs) from the monoclonal antibody 12B4 heavy chain variable region sequence and variable framework residues H2, H24, H27, H29, H48, H49, H67, H71, and H78 (Kabat numbering convention) from the mono clonal antibody 12B4 heavy chain variable region sequence set forth as SEQ ID NO:4, wherein the remainder of the heavy chain is from a human immunoglobulin.

21. A humanized immunoglobulin which specifically binds beta amyloid peptide (Aβ), or antigen-binding fragment thereof, the humanized immunoglobulin comprising a light chain comprising three complementarity determining regions (CDRs) from the monoclonal antibody 12B4 light chain variable region sequence set forth as SEQ ID NO:2, and a heavy chain comprising three complementarity determining regions (CDRs) from the monoclonal antibody 12B4 heavy chain variable region sequence set forth as SEQ ID NO:4 and variable framework residues H24, H27, H29 and H71 (Kabat numbering convention) from the monoclonal antibody 12B4 heavy chain variable region sequence set forth as SEQ ID NO:4, wherein the remainder of the heavy chain is from a human immunoglobulin.

22. A humanized immunoglobulin which specifically binds beta amyloid peptide (Aβ), or antigen-binding fragment thereof, the humanized immunoglobulin comprising a light chain comprising three complementarity determining regions (CDRs) from the monoclonal antibody 12B4 light chain variable region sequence set forth as SEQ ID NO:2, and a heavy chain comprising three complementarity
determining regions (CDRs) from the monoclonal antibody 12B4 heavy chain variable region sequence set forth as SEQ ID NO:4 and variable framework residues H24, H27, H29, H48, H71 and H78 (Kabat numbering convention) from the monoclonal antibody 12B4 heavy chain variable region sequence set forth as SEQ ID NO:4, wherein the remainder of the heavy chain is from a human immunoglobulin.

23. A humanized immunoglobulin which specifically binds beta amyloid peptide (Aβ), or antigen-binding fragment thereof, the humanized immunoglobulin comprising a light chain comprising three complementarity determining regions (CDRs) from the monoclonal antibody 12B4 light chain variable region sequence set forth as SEQ ID NO:2 and variable region framework residue L2 (Kabat numbering convention) from the monoclonal antibody 12B4 light chain, wherein the remainder of the light chain is from a human immunoglobulin, and a heavy chain selected from the group consisting of:
 (i) a heavy chain comprising three complementarity determining regions (CDRs) from the monoclonal antibody 12B4 heavy chain variable region sequence set forth as SEQ ID NO:4 and variable framework residues H2, H24, H27, H29, H48, H49, H67, H71, and H78 (Kabat numbering convention) from the monoclonal antibody 12B4 heavy chain variable region sequence set forth as SEQ ID NO:4, wherein the remainder of the heavy chain is from a human immunoglobulin,
 (ii) a heavy chain comprising three complementarity determining regions (CDRs) from the monoclonal antibody 12B4 heavy chain variable region sequence set forth as SEQ ID NO:4 and variable framework residues H24, H27, H29 and H71 (Kabat numbering convention) from the monoclonal antibody 12B4 heavy chain variable region sequence set forth as SEQ ID NO:4, wherein the remainder of the heavy chain is from a human immunoglobulin, and
 (iii) a heavy chain comprising three complementarity determining regions (CDRs) from the monoclonal antibody 12B4 heavy chain variable region sequence set forth as SEQ ID NO:4 and variable framework residues H24, H27, H29, H48, H71 and H78 (Kabat numbering convention) from the monoclonal antibody 12B4 heavy chain variable region sequence set forth as SEQ ID NO:4, wherein the remainder of the heavy chain is from a human immunoglobulin.

24. A humanized immunoglobulin which specifically binds amyloid beta peptide (Aβ), or antigen-binding fragment thereof, the humanized immunoglobulin comprising a light chain and a heavy chain, the light chain comprising the complementarity determining regions (CDR1, CDR2 and CDR3) of the 12B4 light chain variable region sequence set forth as SEQ ID NO:2, and the heavy chain comprising the complementarity determining regions (CDR1, CDR2 and CDR3) of the 12B4 heavy chain variable region sequence set forth as SEQ ID NO:4.

25. The humanized immunoglobulin or antigen binding fragment of any one of claims 1, 2, 9, 10, 19–23 and 24, which specifically binds to beta amyloid peptide (Aβ) with a binding affinity of at least $10^7 M^{-1}$.

26. The humanized immunoglobulin or antigen binding fragment of any one of claims 1, 2, 9, 10, 19–23 and 24, which specifically binds to beta amyloid peptide (Aβ) with a binding affinity of at least $10^8 M^{-1}$.

27. The humanized immunoglobulin or antigen binding fragment of any one of claims 1, 2, 9, 10, 19–23 and 24, which specifically binds to beta amyloid peptide (Aβ) with a binding affinity of at least $10^9 M^{-1}$.

28. The humanized immunoglobulin or antigen binding fragment of any one of claims 1, 2, 9, 10, 19–23 and 24, wherein the heavy chain isotype is gamma 1.

29. The humanized immunoglobulin or antigen binding fragment of any one of claims 1, 2, 9, 10, 19–23 and 24, which binds to soluble beta amyloid peptide (Aβ).

30. The humanized immunoglobulin or antigen binding fragment of any one of claims 1, 2, 9, 10, 19–23 and 24, which binds to aggregated beta amyloid peptide (Aβ).

31. The humanized immunoglobulin or antigen binding fragment of any one of claims 1, 2, 9, 10, 19–23 and 24, which binds to an epitope within residues 3–7 of beta amyloid peptide (Aβ).

32. The humanized immunoglobulin or antigen binding fragment of any one of claims 1, 2, 9, 10, 19–23 and 24, which mediates phagocytosis of beta amyloid peptide (Aβ).

33. The humanized immunoglobulin or antigen binding fragment of any one of claims 1, 2, 9, 10, 19–23 and 24, which crosses the blood-brain barrier in a subject.

34. The humanized immunoglobulin or antigen binding fragment of any one of claims 1, 2, 9, 10, 19–23 and 24, which reduces beta amyloid peptide (Aβ) plaque burden in a subject.

35. The antigen-binding fragment of any one of claims 1, 2, 9, 10, 19–23 and 24 which is a Fab fragment.

36. A chimeric immunoglobulin, which specifically binds beta amyloid peptide (Aβ) with a binding affinity of at least $10^7 M^{-1}$, comprising the light chain variable region sequence set forth in SEQ ID NO:2 and the heavy chain variable region sequence set forth in SEQ ID NO:4, and comprising constant region sequences from a human immunoglobulin.

37. A pharmaceutical composition comprising the humanized immunoglobulin or antigen-binding fragment of claim 1 and a pharmaceutical carrier.

38. The humanized immunoglobulin of any one of claims 1, 2, 9, 10, 19–23 and 24 which comprises an Fc region having altered binding to Fc receptors or complement proteins.

39. A therapeutic composition comprising the humanized immunoglobulin or antigen-binding fragment of any one of claims 1, 2, 9, 10, 19–23 and 24, wherein the humanized immunoglobulin is of the IgG1 isotype and is capable of reducing neuritic burden in a subject.

40. A therapeutic composition comprising the humanized immunoglobulin of any one of claims 1, 2, 9, 10, 19–23 and 24, wherein the humanized immunoglobulin is of the IgG1 isotype and binds to soluble beta amyloid peptide (Aβ), wherein the humanized immunoglobulin is capable of reducing neuritic burden in a subject.

41. A pharmaceutical composition comprising the humanized immunoglobulin or antigen-binding fragment of claim 2 and a pharmaceutical carrier.

42. A pharmaceutical composition comprising the humanized immunoglobulin or antigen-binding fragment of claim 9 and a pharmaceutical carrier.

43. A pharmaceutical composition comprising the humanized immunoglobulin or antigen-binding fragment of claim 10 and a pharmaceutical carrier.

44. A pharmaceutical composition comprising the humanized immunoglobulin or antigen-binding fragment of claim 19 and a pharmaceutical carrier.

45. A pharmaceutical composition comprising the humanized immunoglobulin or antigen-binding fragment of claim 20 and a pharmaceutical carrier.

46. A pharmaceutical composition comprising the humanized immunoglobulin or antigen-binding fragment of claim 21 and a pharmaceutical carrier.

47. A pharmaceutical composition comprising the humanized immunoglobulin or antigen-binding fragment of claim 22 and a pharmaceutical carrier.

48. A pharmaceutical composition comprising the humanized immunoglobulin or antigen-binding fragment of claim 23 and a pharmaceutical carrier.

49. A pharmaceutical composition comprising the humanized immunoglobulin or antigen-binding fragment of claim 24 and a pharmaceutical carrier.

50. An immunoglobulin which specifically binds to beta amyloid peptide (Aβ), or antigen-binding fragment thereof, comprising a heavy chain variable region sequence as set forth in residues 1–123 of SEQ ID NO:8 and a light chain variable region sequence as set forth in residues 1–112 of SEQ ID NO:6.

51. An immunoglobulin which specifically binds to beta amyloid peptide or antigen-binding fragment thereof, comprising a heavy chain variable region sequence as set forth in residues 1–123 of SEQ ID NO:10 and a light chain variable region sequence as set forth in residues 1–112 of SEQ ID NO:6.

52. An immunoglobulin which specifically binds to beta amyloid peptide (Aβ), or antigen-binding fragment thereof, comprising a heavy chain variable region sequence as set forth in residues 1–123 of SEQ ID NO:12 and a light chain variable region sequence as set forth in residues 1–112 of SEQ ID NO:6.

53. An immunoglobulin comprising a heavy chain variable region sequence as set forth in residues 1–123 of SEQ ID NO:8 and a light chain variable region sequence as set forth in residues 1–112 of SEQ ID NO:6.

54. An immunoglobulin comprising a heavy chain variable region sequence as set forth in residues 1–123 of SEQ ID NO:10 and a light chain variable region sequence as set forth in residues 1–112 of SEQ ID NO:6.

55. An immunoglobulin comprising a heavy chain variable region sequence as set forth in residues 1–123 of SEQ ID NO:12 and a light chain variable region sequence as set forth in residues 1–112 of SEQ ID NO:6.

* * * * *

SEQUENCE LISTING

```
<160> NUMBER OF SEQ ID NOS: 38

<210> SEQ ID NO 1
<211> LENGTH: 393
<212> TYPE: DNA
<213> ORGANISM: Mus musculus
<220> FEATURE:
<221> NAME/KEY: sig_peptide
<222> LOCATION: (1)...(57)
<220> FEATURE:
<221> NAME/KEY: CDS
<222> LOCATION: (1)...(393)

<400> SEQUENCE: 1 atg aag ttg cct gtt agg ctg ttg gtg ctg atg ttc tgg att cct gct      48
Met Lys Leu Pro Val Arg Leu Leu Val Leu Met Phe Trp Ile Pro Ala
            -15                 -10                 -5 tcc agc agt gat gtt ttg atg acc caa act cca ctc tcc ctg cct gtc      96
```

```
Ser Ser Ser Asp Val Leu Met Thr Gln Thr Pro Leu Ser Leu Pro Val
        1               5                  10 agt ctt gga gat caa gcc tcc atc tct tgc aga tct agt cag aac att      144
Ser Leu Gly Asp Gln Ala Ser Ile Ser Cys Arg Ser Ser Gln Asn Ile
    15                  20                  25 gtt cat agt aat gga aac acc tat tta gaa tgg tac ctg cag aaa cca      192
Val His Ser Asn Gly Asn Thr Tyr Leu Glu Trp Tyr Leu Gln Lys Pro
30                  35                  40                  45 ggc cag tct cca aag ctc ctg atc tac aaa gtt tcc aac cga ttt tct      240
Gly Gln Ser Pro Lys Leu Leu Ile Tyr Lys Val Ser Asn Arg Phe Ser
                50                  55                  60 ggg gtc cca gac agg ttc agt ggc agt gga tca ggg aca gat ttc aca      288
Gly Val Pro Asp Arg Phe Ser Gly Ser Gly Ser Gly Thr Asp Phe Thr
            65                  70                  75 ctc aag atc agc aga gtg gag gct gag gat ctg gga gtt tat tac tgc      336
Leu Lys Ile Ser Arg Val Glu Ala Glu Asp Leu Gly Val Tyr Tyr Cys
        80                  85                  90 ttt caa ggt tca cat gtt ccg ctc acg ttc ggt gct ggg acc aag ctg      384
Phe Gln Gly Ser His Val Pro Leu Thr Phe Gly Ala Gly Thr Lys Leu
    95                  100                 105 gag ctg aaa                                                          393
Glu Leu Lys
110

<210> SEQ ID NO 2
<211> LENGTH: 131
<212> TYPE: PRT
<213> ORGANISM: Mus musculus
<220> FEATURE:
<221> NAME/KEY: SIGNAL
<222> LOCATION: (1)...(19)

<400> SEQUENCE: 2

Met Lys Leu Pro Val Arg Leu Leu Val Leu Met Phe Trp Ile Pro Ala
                -15                 -10                 -5

Ser Ser Ser Asp Val Leu Met Thr Gln Thr Pro Leu Ser Leu Pro Val
        1               5                   10

Ser Leu Gly Asp Gln Ala Ser Ile Ser Cys Arg Ser Ser Gln Asn Ile
    15                  20                  25

Val His Ser Asn Gly Asn Thr Tyr Leu Glu Trp Tyr Leu Gln Lys Pro
30                  35                  40                  45

Gly Gln Ser Pro Lys Leu Leu Ile Tyr Lys Val Ser Asn Arg Phe Ser
                50                  55                  60

Gly Val Pro Asp Arg Phe Ser Gly Ser Gly Ser Gly Thr Asp Phe Thr
            65                  70                  75

Leu Lys Ile Ser Arg Val Glu Ala Glu Asp Leu Gly Val Tyr Tyr Cys
        80                  85                  90

Phe Gln Gly Ser His Val Pro Leu Thr Phe Gly Ala Gly Thr Lys Leu
    95                  100                 105

Glu Leu Lys
110

<210> SEQ ID NO 3
<211> LENGTH: 426
<212> TYPE: DNA
<213> ORGANISM: Mus musculus
<220> FEATURE:
<221> NAME/KEY: CDS
<222> LOCATION: (1)...(426)
<220> FEATURE:
<221> NAME/KEY: sig_peptide
```

<222> LOCATION: (1)...(57)

<400> SEQUENCE: 3

```
atg gac agg ctt act tcc tca ttc ctg ctg ctg att gtc cct gca tat      48
Met Asp Arg Leu Thr Ser Ser Phe Leu Leu Leu Ile Val Pro Ala Tyr
            -15                 -10                 -5 gtc ctg tcc cag gtt act ctg aaa gag tct ggc cct ggg ata ttg cag      96
Val Leu Ser Gln Val Thr Leu Lys Glu Ser Gly Pro Gly Ile Leu Gln
                1               5                   10 ccc tcc cag acc ctc agt ctg act tgt tct ttc tct ggg ttt tca ctg     144
Pro Ser Gln Thr Leu Ser Leu Thr Cys Ser Phe Ser Gly Phe Ser Leu
        15                  20                  25 agc act aat ggt atg ggt gtg agc tgg att cgt cag cct tca gga aag     192
Ser Thr Asn Gly Met Gly Val Ser Trp Ile Arg Gln Pro Ser Gly Lys
30                  35                  40                  45 ggt ctg gag tgg ctg gca cac att tac tgg gat gag gac aag cgc tat     240
Gly Leu Glu Trp Leu Ala His Ile Tyr Trp Asp Glu Asp Lys Arg Tyr
                50                  55                  60 aac cca tcc ctg aag agc cgg ctc aca atc tcc aag gat acc tct aac     288
Asn Pro Ser Leu Lys Ser Arg Leu Thr Ile Ser Lys Asp Thr Ser Asn
            65                  70                  75 aat cag gta ttc ctc aag atc acc aat gtg gac act gct gat act gcc     336
Asn Gln Val Phe Leu Lys Ile Thr Asn Val Asp Thr Ala Asp Thr Ala
        80                  85                  90 aca tac tac tgt gct cga agg agg atc atc tat gat gtt gag gac tac     384
Thr Tyr Tyr Cys Ala Arg Arg Arg Ile Ile Tyr Asp Val Glu Asp Tyr
    95                  100                 105 ttt gac tac tgg ggc caa ggc acc act ctc aca gtc tcc tca             426
Phe Asp Tyr Trp Gly Gln Gly Thr Thr Leu Thr Val Ser Ser
110                 115                 120
```

<210> SEQ ID NO 4
<211> LENGTH: 142
<212> TYPE: PRT
<213> ORGANISM: Mus musculus
<220> FEATURE:
<221> NAME/KEY: SIGNAL
<222> LOCATION: (1)...(19)

<400> SEQUENCE: 4

```
Met Asp Arg Leu Thr Ser Ser Phe Leu Leu Leu Ile Val Pro Ala Tyr
            -15                 -10                 -5

Val Leu Ser Gln Val Thr Leu Lys Glu Ser Gly Pro Gly Ile Leu Gln
                1               5                   10

Pro Ser Gln Thr Leu Ser Leu Thr Cys Ser Phe Ser Gly Phe Ser Leu
        15                  20                  25

Ser Thr Asn Gly Met Gly Val Ser Trp Ile Arg Gln Pro Ser Gly Lys
30                  35                  40                  45

Gly Leu Glu Trp Leu Ala His Ile Tyr Trp Asp Glu Asp Lys Arg Tyr
                50                  55                  60

Asn Pro Ser Leu Lys Ser Arg Leu Thr Ile Ser Lys Asp Thr Ser Asn
            65                  70                  75

Asn Gln Val Phe Leu Lys Ile Thr Asn Val Asp Thr Ala Asp Thr Ala
        80                  85                  90

Thr Tyr Tyr Cys Ala Arg Arg Arg Ile Ile Tyr Asp Val Glu Asp Tyr
    95                  100                 105

Phe Asp Tyr Trp Gly Gln Gly Thr Thr Leu Thr Val Ser Ser
110                 115                 120
```

<210> SEQ ID NO 5
<211> LENGTH: 396
<212> TYPE: DNA
<213> ORGANISM: Artificial Sequence
<220> FEATURE:
<223> OTHER INFORMATION: Description of Artificial Sequence: humanized 12B4VLv1
<220> FEATURE:
<221> NAME/KEY: CDS
<222> LOCATION: (1)...(396)
<220> FEATURE:
<221> NAME/KEY: sig_peptide
<222> LOCATION: (1)...(60)

<400> SEQUENCE: 5

```
atg agg ctc cct gct cag ctc ctg ggg ctg cta atg ctc tgg gtc tct      48
Met Arg Leu Pro Ala Gln Leu Leu Gly Leu Leu Met Leu Trp Val Ser
-20             -15                 -10                 -5 gga tcc agt ggg gat gtt gtg atg act cag tct cca ctc tcc ctg ccc      96
Gly Ser Ser Gly Asp Val Val Met Thr Gln Ser Pro Leu Ser Leu Pro
            1               5                   10 gtc acc cct gga gag ccg gcc tcc atc tcc tgc agg tct agt cag aac     144
Val Thr Pro Gly Glu Pro Ala Ser Ile Ser Cys Arg Ser Ser Gln Asn
        15                  20                  25 att gtt cat agt aat gga aac acc tat ttg gaa tgg tac ctg cag aag     192
Ile Val His Ser Asn Gly Asn Thr Tyr Leu Glu Trp Tyr Leu Gln Lys
    30                  35                  40 cca ggg cag tct cca cag ctc ctg atc tac aaa gtt tcc aac cga ttt     240
Pro Gly Gln Ser Pro Gln Leu Leu Ile Tyr Lys Val Ser Asn Arg Phe
45                  50                  55                  60 tct ggg gtc cct gac agg ttc agt ggc agt gga tca ggc aca gat ttt     288
Ser Gly Val Pro Asp Arg Phe Ser Gly Ser Gly Ser Gly Thr Asp Phe
                65                  70                  75 aca ctg aaa atc agc aga gtg gag gct gag gat gtt ggg gtt tat tac     336
Thr Leu Lys Ile Ser Arg Val Glu Ala Glu Asp Val Gly Val Tyr Tyr
            80                  85                  90 tgc ttt caa ggt tca cat gtt ccg ctc acg ttc ggt cag ggg acc aag     384
Cys Phe Gln Gly Ser His Val Pro Leu Thr Phe Gly Gln Gly Thr Lys
        95                  100                 105 ctg gag atc aaa                                                     396
Leu Glu Ile Lys
    110
```

<210> SEQ ID NO 6
<211> LENGTH: 132
<212> TYPE: PRT
<213> ORGANISM: Artificial Sequence
<220> FEATURE:
<223> OTHER INFORMATION: Description of Artificial Sequence: humanized 12B4VLv1
<220> FEATURE:
<221> NAME/KEY: SIGNAL
<222> LOCATION: (1)...(20)

<400> SEQUENCE: 6

```
Met Arg Leu Pro Ala Gln Leu Leu Gly Leu Leu Met Leu Trp Val Ser
-20             -15                 -10                 -5

Gly Ser Ser Gly Asp Val Val Met Thr Gln Ser Pro Leu Ser Leu Pro
            1               5                   10

Val Thr Pro Gly Glu Pro Ala Ser Ile Ser Cys Arg Ser Ser Gln Asn
        15                  20                  25

Ile Val His Ser Asn Gly Asn Thr Tyr Leu Glu Trp Tyr Leu Gln Lys
    30                  35                  40

Pro Gly Gln Ser Pro Gln Leu Leu Ile Tyr Lys Val Ser Asn Arg Phe
```

```
                     45                  50                  55                  60
Ser Gly Val Pro Asp Arg Phe Ser Gly Ser Gly Ser Gly Thr Asp Phe
                 65                  70                  75

Thr Leu Lys Ile Ser Arg Val Glu Ala Glu Asp Val Gly Val Tyr Tyr
                 80                  85                  90

Cys Phe Gln Gly Ser His Val Pro Leu Thr Phe Gly Gln Gly Thr Lys
                 95                 100                 105

Leu Glu Ile Lys
        110

<210> SEQ ID NO 7
<211> LENGTH: 426
<212> TYPE: DNA
<213> ORGANISM: Artificial Sequence
<220> FEATURE:
<223> OTHER INFORMATION: Description of Artificial Sequence: humanized
      12B4VHv1
<220> FEATURE:
<221> NAME/KEY: CDS
<222> LOCATION: (1)...(426)
<220> FEATURE:
<221> NAME/KEY: sig_peptide
<222> LOCATION: (1)...(57)

<400> SEQUENCE: 7 atg aag cac ctg tgg ttc ttc ctc ctg ctg gtg gca gct ccc aga tgg        48
Met Lys His Leu Trp Phe Phe Leu Leu Leu Val Ala Ala Pro Arg Trp
            -15                 -10                  -5 gtc ctg tcc cag gtg cag ctg cag gag tcg ggc cca gga ctg gtg aag        96
Val Leu Ser Gln Val Gln Leu Gln Glu Ser Gly Pro Gly Leu Val Lys
              1               5                  10 cct tcg gag acc ctg tcc ctc acc tgc act ttc tct ggt ttt tcc ctg       144
Pro Ser Glu Thr Leu Ser Leu Thr Cys Thr Phe Ser Gly Phe Ser Leu
         15                  20                  25 agc act aat ggt atg ggt gtg agc tgg atc cgg cag ccc cca ggg aag       192
Ser Thr Asn Gly Met Gly Val Ser Trp Ile Arg Gln Pro Pro Gly Lys
     30                  35                  40                  45 gga ctg gag tgg ctg gca cac atc tat tgg gat gag gac aag cgc tat       240
Gly Leu Glu Trp Leu Ala His Ile Tyr Trp Asp Glu Asp Lys Arg Tyr
                 50                  55                  60 aac cca tcc ctc aag agt cga ctc acc ata tca aag gac acg tcc aag       288
Asn Pro Ser Leu Lys Ser Arg Leu Thr Ile Ser Lys Asp Thr Ser Lys
                 65                  70                  75 aac cag gta tcc ctg aag ctg agc tct gtg acc gct gca gac acg gcc       336
Asn Gln Val Ser Leu Lys Leu Ser Ser Val Thr Ala Ala Asp Thr Ala
             80                  85                  90 gtg tat tac tgt gcg aga agg agg atc atc tat gat gtt gag gac tac       384
Val Tyr Tyr Cys Ala Arg Arg Arg Ile Ile Tyr Asp Val Glu Asp Tyr
         95                 100                 105 ttt gac tac tgg ggc caa ggg acc acg gtc acc gtc tcc tca               426
Phe Asp Tyr Trp Gly Gln Gly Thr Thr Val Thr Val Ser Ser
110                 115                 120

<210> SEQ ID NO 8
<211> LENGTH: 142
<212> TYPE: PRT
<213> ORGANISM: Artificial Sequence
<220> FEATURE:
<223> OTHER INFORMATION: Description of Artificial Sequence: humanized
      12B4VHv1
<220> FEATURE:
<221> NAME/KEY: SIGNAL
<222> LOCATION: (1)...(19)
```

```
<400> SEQUENCE: 8

Met Lys His Leu Trp Phe Phe Leu Leu Leu Val Ala Ala Pro Arg Trp
            -15                 -10                  -5

Val Leu Ser Gln Val Gln Leu Gln Glu Ser Gly Pro Gly Leu Val Lys
             1                   5                  10

Pro Ser Glu Thr Leu Ser Leu Thr Cys Thr Phe Ser Gly Phe Ser Leu
            15                  20                  25

Ser Thr Asn Gly Met Gly Val Ser Trp Ile Arg Gln Pro Pro Gly Lys
 30              35                  40                  45

Gly Leu Glu Trp Leu Ala His Ile Tyr Trp Asp Glu Asp Lys Arg Tyr
             50                  55                  60

Asn Pro Ser Leu Lys Ser Arg Leu Thr Ile Ser Lys Asp Thr Ser Lys
            65                  70                  75

Asn Gln Val Ser Leu Lys Leu Ser Ser Val Thr Ala Ala Asp Thr Ala
             80                  85                  90

Val Tyr Tyr Cys Ala Arg Arg Arg Ile Ile Tyr Asp Val Glu Asp Tyr
 95                 100                 105

Phe Asp Tyr Trp Gly Gln Gly Thr Thr Val Thr Val Ser Ser
110             115                 120

<210> SEQ ID NO 9
<211> LENGTH: 426
<212> TYPE: DNA
<213> ORGANISM: Artificial Sequence
<220> FEATURE:
<221> NAME/KEY: CDS
<222> LOCATION: (1)...(426)
<220> FEATURE:
<223> OTHER INFORMATION: Description of Artificial Sequence: humanized
      12B4VLv2
<220> FEATURE:
<221> NAME/KEY: sig_peptide
<222> LOCATION: (1)...(57)

<400> SEQUENCE: 9 atg aag cac ctg tgg ttc ttc ctc ctg ctg gtg gca gct ccc aga tgg      48
Met Lys His Leu Trp Phe Phe Leu Leu Leu Val Ala Ala Pro Arg Trp
            -15                 -10                  -5 gtc ctg tcc cag ctg cag ctg cag gag tcg ggc cca gga ctg gtg aag      96
Val Leu Ser Gln Leu Gln Leu Gln Glu Ser Gly Pro Gly Leu Val Lys
             1                   5                  10 cct tcg gag acc ctg tcc ctc acc tgc act ttc tct ggt ttt tcc ctg     144
Pro Ser Glu Thr Leu Ser Leu Thr Cys Thr Phe Ser Gly Phe Ser Leu
            15                  20                  25 agc act aat ggt atg ggt gtg agc tgg atc cgg cag ccc cca ggg aag     192
Ser Thr Asn Gly Met Gly Val Ser Trp Ile Arg Gln Pro Pro Gly Lys
 30              35                  40                  45 gga ctg gag tgg att ggg cac atc tat tgg gat gag gac aag cgc tat     240
Gly Leu Glu Trp Ile Gly His Ile Tyr Trp Asp Glu Asp Lys Arg Tyr
             50                  55                  60 aac cca tcc ctc aag agt cga gtc acc ata tca aag gac acg tcc aag     288
Asn Pro Ser Leu Lys Ser Arg Val Thr Ile Ser Lys Asp Thr Ser Lys
            65                  70                  75 aac cag ttc tcc ctg aag ctg agc tct gtg acc gct gca gac acg gcc     336
Asn Gln Phe Ser Leu Lys Leu Ser Ser Val Thr Ala Ala Asp Thr Ala
             80                  85                  90 gtg tat tac tgt gcg aga agg agg atc atc tat gat gtt gag gac tac     384
Val Tyr Tyr Cys Ala Arg Arg Arg Ile Ile Tyr Asp Val Glu Asp Tyr
 95                 100                 105 ttt gac tac tgg ggc caa ggg acc acg gtc acc gtc tcc tca             426
Phe Asp Tyr Trp Gly Gln Gly Thr Thr Val Thr Val Ser Ser
```

```
Phe Asp Tyr Trp Gly Gln Gly Thr Thr Val Thr Val Ser Ser
110                 115                 120
```

```
<210> SEQ ID NO 10
<211> LENGTH: 142
<212> TYPE: PRT
<213> ORGANISM: Artificial Sequence
<220> FEATURE:
<223> OTHER INFORMATION: Description of Artificial Sequence: humanized
      12B4VLv2
<220> FEATURE:
<221> NAME/KEY: SIGNAL
<222> LOCATION: (1)...(19)

<400> SEQUENCE: 10
```

```
Met Lys His Leu Trp Phe Phe Leu Leu Leu Val Ala Ala Pro Arg Trp
                -15                 -10                 -5

Val Leu Ser Gln Leu Gln Leu Gln Glu Ser Gly Pro Gly Leu Val Lys
                 1               5                  10

Pro Ser Glu Thr Leu Ser Leu Thr Cys Thr Phe Ser Gly Phe Ser Leu
         15                  20                  25

Ser Thr Asn Gly Met Gly Val Ser Trp Ile Arg Gln Pro Pro Gly Lys
 30                  35                  40                  45

Gly Leu Glu Trp Ile Gly His Ile Tyr Trp Asp Glu Asp Lys Arg Tyr
                 50                  55                  60

Asn Pro Ser Leu Lys Ser Arg Val Thr Ile Ser Lys Asp Thr Ser Lys
                 65                  70                  75

Asn Gln Phe Ser Leu Lys Leu Ser Ser Val Thr Ala Ala Asp Thr Ala
         80                  85                  90

Val Tyr Tyr Cys Ala Arg Arg Ile Ile Tyr Asp Val Glu Asp Tyr
     95                  100                 105

Phe Asp Tyr Trp Gly Gln Gly Thr Thr Val Thr Val Ser Ser
110                 115                 120
```

```
<210> SEQ ID NO 11
<211> LENGTH: 426
<212> TYPE: DNA
<213> ORGANISM: Artificial Sequence
<220> FEATURE:
<223> OTHER INFORMATION: Description of Artificial Sequence: humanized
      12B4VLv3
<220> FEATURE:
<221> NAME/KEY: CDS
<222> LOCATION: (1)...(426)
<220> FEATURE:
<221> NAME/KEY: sig_peptide
<222> LOCATION: (1)...(57)

<400> SEQUENCE: 11
```

```
atg aag cac ctg tgg ttc ttc ctc ctg ctg gtg gca gct ccc aga tgg      48
Met Lys His Leu Trp Phe Phe Leu Leu Leu Val Ala Ala Pro Arg Trp
                -15                 -10                 -5 gtc ctg tcc cag ctg cag ctg cag gag tcg ggc cca gga ctg gtg aag      96
Val Leu Ser Gln Leu Gln Leu Gln Glu Ser Gly Pro Gly Leu Val Lys
                 1               5                  10 cct tcg gag acc ctg tcc ctc acc tgc act ttc tct ggt ttt tcc ctg     144
Pro Ser Glu Thr Leu Ser Leu Thr Cys Thr Phe Ser Gly Phe Ser Leu
         15                  20                  25 agc act aat ggt atg ggt gtg agc tgg atc cgg cag ccc cca ggg aag     192
Ser Thr Asn Gly Met Gly Val Ser Trp Ile Arg Gln Pro Pro Gly Lys
 30                  35                  40                  45 gga ctg gag tgg ctg ggg cac atc tat tgg gat gag gac aag cgc tat     240
Gly Leu Glu Trp Leu Gly His Ile Tyr Trp Asp Glu Asp Lys Arg Tyr
```

```
                50                  55                   60
aac cca tcc ctc aag agt cga gtc acc ata tca aag gac acg tcc aag      288
Asn Pro Ser Leu Lys Ser Arg Val Thr Ile Ser Lys Asp Thr Ser Lys
             65                  70                  75 aac cag gta tcc ctg aag ctg agc tct gtg acc gct gca gac acg gcc      336
Asn Gln Val Ser Leu Lys Leu Ser Ser Val Thr Ala Ala Asp Thr Ala
         80                  85                  90 gtg tat tac tgt gcg aga agg agg atc atc tat gat gtt gag gac tac      384
Val Tyr Tyr Cys Ala Arg Arg Arg Ile Ile Tyr Asp Val Glu Asp Tyr
     95                 100                 105 ttt gac tac tgg ggc caa ggg acc acg gtc acc gtc tcc tca              426
Phe Asp Tyr Trp Gly Gln Gly Thr Thr Val Thr Val Ser Ser
110                 115                 120

<210> SEQ ID NO 12
<211> LENGTH: 142
<212> TYPE: PRT
<213> ORGANISM: Artificial Sequence
<220> FEATURE:
<223> OTHER INFORMATION: Description of Artificial Sequence: humanized
      12B4VLv3
<220> FEATURE:
<221> NAME/KEY: SIGNAL
<222> LOCATION: (1)...(19)

<400> SEQUENCE: 12

Met Lys His Leu Trp Phe Phe Leu Leu Leu Val Ala Ala Pro Arg Trp
                -15                 -10                  -5

Val Leu Ser Gln Leu Gln Leu Gln Glu Ser Gly Pro Gly Leu Val Lys
              1               5                  10

Pro Ser Glu Thr Leu Ser Leu Thr Cys Thr Phe Ser Gly Phe Ser Leu
         15                  20                  25

Ser Thr Asn Gly Met Gly Val Ser Trp Ile Arg Gln Pro Pro Gly Lys
 30                  35                  40                  45

Gly Leu Glu Trp Leu Gly His Ile Tyr Trp Asp Glu Asp Lys Arg Tyr
                 50                  55                  60

Asn Pro Ser Leu Lys Ser Arg Val Thr Ile Ser Lys Asp Thr Ser Lys
             65                  70                  75

Asn Gln Val Ser Leu Lys Leu Ser Ser Val Thr Ala Ala Asp Thr Ala
         80                  85                  90

Val Tyr Tyr Cys Ala Arg Arg Arg Ile Ile Tyr Asp Val Glu Asp Tyr
     95                 100                 105

Phe Asp Tyr Trp Gly Gln Gly Thr Thr Val Thr Val Ser Ser
110                 115                 120

<210> SEQ ID NO 13
<211> LENGTH: 135
<212> TYPE: DNA
<213> ORGANISM: Artificial Sequence
<220> FEATURE:
<223> OTHER INFORMATION: primer

<400> SEQUENCE: 13
gagattaagc ttgccgccac catgaggctc cctgctcagc tcctggggct gctaatgctc      60
tgggtctctg gatccagtgg ggatgttgtg atgactcagt ctccactctc cctgcccgtc     120 accccctggag agccg                                                    135

<210> SEQ ID NO 14
<211> LENGTH: 131
<212> TYPE: DNA
```

-continued

```
<213> ORGANISM: Artificial Sequence
<220> FEATURE:
<223> OTHER INFORMATION: primer

<400> SEQUENCE: 14
aggagctgtg gagactgccc tggcttctgc aggtaccatt ccaaataggt gtttccatta      60
ctatgaacaa tgttctgact agacctgcag gagatggagg ccggctctcc agggtgacg     120 ggcagggaga g                                                          131

<210> SEQ ID NO 15
<211> LENGTH: 132
<212> TYPE: DNA
<213> ORGANISM: Artificial Sequence
<220> FEATURE:
<223> OTHER INFORMATION: primer

<400> SEQUENCE: 15
tgcagaagcc agggcagtct ccacagctcc tgatctacaa agtttccaac cgattttctg      60
gggtccctga caggttcagt ggcagtggat caggcacaga ttttacactg aaaatcagca    120
gagtggaggc tg                                                         132

<210> SEQ ID NO 16
<211> LENGTH: 130
<212> TYPE: DNA
<213> ORGANISM: Artificial Sequence
<220> FEATURE:
<223> OTHER INFORMATION: primer

<400> SEQUENCE: 16
tgatatggat ccactcacgt ttgatctcca gcttggtccc ctgaccgaac gtgagcggaa      60
catgtgaacc ttgaaagcag taataaaccc aacatcctc agcctccact ctgctgattt    120
tcagtgtaaa                                                            130

<210> SEQ ID NO 17
<211> LENGTH: 143
<212> TYPE: DNA
<213> ORGANISM: Artificial Sequence
<220> FEATURE:
<223> OTHER INFORMATION: primer

<400> SEQUENCE: 17
gagataaagc ttgccgccac catgaagcac ctgtggttct tcctcctgct ggtggcagct      60
cccagatggg tcctgtccca ggtgcagctg caggagtcgg gcccaggact ggtgaagcct    120
tcggagaccc tgtccctcac ctg                                             143

<210> SEQ ID NO 18
<211> LENGTH: 137
<212> TYPE: DNA
<213> ORGANISM: Artificial Sequence
<220> FEATURE:
<223> OTHER INFORMATION: primer

<400> SEQUENCE: 18
tcctcatccc aatagatgtg tgccagccac tccagtccct tccctggggg ctgccggatc      60
cagctcacac ccataccatt agtgctcagg gaaaaaccag agaaagtgca ggtgagggac    120
agggtctccg aaggctt                                                    137

<210> SEQ ID NO 19
<211> LENGTH: 138
```

<212> TYPE: DNA
<213> ORGANISM: Artificial Sequence
<220> FEATURE:
<223> OTHER INFORMATION: primer

<400> SEQUENCE: 19
gtggctggca cacatctatt gggatgagga caagcgctat aacccatccc tcaagagtcg     60
actcaccata tcaaaggaca cgtccaagaa ccaggtatcc ctgaagctga gctctgtgac    120
cgctgcagac acggccgt                                                  138

<210> SEQ ID NO 20
<211> LENGTH: 139
<212> TYPE: DNA
<213> ORGANISM: Artificial Sequence
<220> FEATURE:
<223> OTHER INFORMATION: primer

<400> SEQUENCE: 20
tcatatggat ccactcacct gaggagacgg tgaccgtggt cccttggccc cagtagtcaa     60
agtagtcctc aacatcatag atgatcctcc ttctcgcaca gtaatacacg gccgtgtctg    120
cagcggtcac agagctcag                                                 139

<210> SEQ ID NO 21
<211> LENGTH: 22
<212> TYPE: DNA
<213> ORGANISM: Artificial Sequence
<220> FEATURE:
<223> OTHER INFORMATION: primer

<400> SEQUENCE: 21
gagattaagc ttgccgccac ca                                              22

<210> SEQ ID NO 22
<211> LENGTH: 21
<212> TYPE: DNA
<213> ORGANISM: Artificial Sequence
<220> FEATURE:
<223> OTHER INFORMATION: primer

<400> SEQUENCE: 22
aggagctgtg gagactgccc t                                               21

<210> SEQ ID NO 23
<211> LENGTH: 20
<212> TYPE: DNA
<213> ORGANISM: Artificial Sequence
<220> FEATURE:
<223> OTHER INFORMATION: primer

<400> SEQUENCE: 23
tgcagaagcc agggcagtct                                                 20

<210> SEQ ID NO 24
<211> LENGTH: 28
<212> TYPE: DNA
<213> ORGANISM: Artificial Sequence
<220> FEATURE:
<223> OTHER INFORMATION: primer

<400> SEQUENCE: 24
tgatatggat ccactcacgt ttgatctc                                        28

<210> SEQ ID NO 25

```
<211> LENGTH: 23
<212> TYPE: DNA
<213> ORGANISM: Artificial Sequence
<220> FEATURE:
<223> OTHER INFORMATION: primer

<400> SEQUENCE: 25
gagataaagc ttgccgccac cat                                              23

<210> SEQ ID NO 26
<211> LENGTH: 24
<212> TYPE: DNA
<213> ORGANISM: Artificial Sequence
<220> FEATURE:
<223> OTHER INFORMATION: primer

<400> SEQUENCE: 26
tcctcatccc aatagatgtg tgcc                                             24

<210> SEQ ID NO 27
<211> LENGTH: 22
<212> TYPE: DNA
<213> ORGANISM: Artificial Sequence
<220> FEATURE:
<223> OTHER INFORMATION: primer

<400> SEQUENCE: 27
gtggctggca cacatctatt gg                                               22

<210> SEQ ID NO 28
<211> LENGTH: 24
<212> TYPE: DNA
<213> ORGANISM: Artificial Sequence
<220> FEATURE:
<223> OTHER INFORMATION: primer

<400> SEQUENCE: 28
tcatatggat ccactcacct gagg                                             24

<210> SEQ ID NO 29
<211> LENGTH: 360
<212> TYPE: DNA
<213> ORGANISM: Homo sapiens
<220> FEATURE:
<221> NAME/KEY: CDS
<222> LOCATION: (1)...(360)
<220> FEATURE:
<221> NAME/KEY: sig_peptide
<222> LOCATION: (1)...(60)

<400> SEQUENCE: 29 atg agg ctc cct gct cag ctc ctg ggg ctg cta atg ctc tgg gtc tct       48
Met Arg Leu Pro Ala Gln Leu Leu Gly Leu Leu Met Leu Trp Val Ser
-20             -15                 -10                 -5 gga tcc agt ggg gat att gtg atg act cag tct cca ctc tcc ctg ccc       96
Gly Ser Ser Gly Asp Ile Val Met Thr Gln Ser Pro Leu Ser Leu Pro
             1               5                  10 gtc acc cct gga gag ccg gcc tcc atc tcc tgc agg tct agt cag agc      144
Val Thr Pro Gly Glu Pro Ala Ser Ile Ser Cys Arg Ser Ser Gln Ser
        15                  20                  25 ctc ctg cat agt aat gga tac aac tat ttg gat tgg tac ctg cag aag      192
Leu Leu His Ser Asn Gly Tyr Asn Tyr Leu Asp Trp Tyr Leu Gln Lys
    30                  35                  40 cca ggg cag tct cca cag ctc ctg atc tat ttg ggt tct aat cgg gcc      240
Pro Gly Gln Ser Pro Gln Leu Leu Ile Tyr Leu Gly Ser Asn Arg Ala
45                  50                  55                  60
```

```
tcc ggg gtc cct gac agg ttc agt ggc agt gga tca ggc aca gat ttt      288
Ser Gly Val Pro Asp Arg Phe Ser Gly Ser Gly Ser Gly Thr Asp Phe
                65                  70                  75 aca ctg aaa atc agc aga gtg gag gct gag gat gtt ggg gtt tat tac      336
Thr Leu Lys Ile Ser Arg Val Glu Ala Glu Asp Val Gly Val Tyr Tyr
            80                  85                  90 tgc atg caa gct cta caa act cct                                      360
Cys Met Gln Ala Leu Gln Thr Pro
        95                  100
```

<210> SEQ ID NO 30
<211> LENGTH: 120
<212> TYPE: PRT
<213> ORGANISM: Homo sapiens
<220> FEATURE:
<221> NAME/KEY: SIGNAL
<222> LOCATION: (1)...(20)

<400> SEQUENCE: 30

```
Met Arg Leu Pro Ala Gln Leu Leu Gly Leu Leu Met Leu Trp Val Ser
-20             -15                 -10                 -5

Gly Ser Ser Gly Asp Ile Val Met Thr Gln Ser Pro Leu Ser Leu Pro
                1               5                   10

Val Thr Pro Gly Glu Pro Ala Ser Ile Ser Cys Arg Ser Ser Gln Ser
            15                  20                  25

Leu Leu His Ser Asn Gly Tyr Asn Tyr Leu Asp Trp Tyr Leu Gln Lys
        30                  35                  40

Pro Gly Gln Ser Pro Gln Leu Leu Ile Tyr Leu Gly Ser Asn Arg Ala
45                  50                  55                  60

Ser Gly Val Pro Asp Arg Phe Ser Gly Ser Gly Ser Gly Thr Asp Phe
                65                  70                  75

Thr Leu Lys Ile Ser Arg Val Glu Ala Glu Asp Val Gly Val Tyr Tyr
            80                  85                  90

Cys Met Gln Ala Leu Gln Thr Pro
        95                  100
```

<210> SEQ ID NO 31
<211> LENGTH: 300
<212> TYPE: DNA
<213> ORGANISM: Homo sapiens
<220> FEATURE:
<221> NAME/KEY: CDS
<222> LOCATION: (1)...(300)

<400> SEQUENCE: 31

```
gat att gtg atg act cag tct cca ctc tcc ctg ccc gtc acc cct gga       48
Asp Ile Val Met Thr Gln Ser Pro Leu Ser Leu Pro Val Thr Pro Gly
1               5                   10                  15 gag ccg gcc tcc atc tcc tgc agg tct agt cag agc ctc ctg cat cgt       96
Glu Pro Ala Ser Ile Ser Cys Arg Ser Ser Gln Ser Leu Leu His Arg
                20                  25                  30 tat gga tac aac tat ttg gat tgg tac ctg cag aag cca ggg cag tct      144
Tyr Gly Tyr Asn Tyr Leu Asp Trp Tyr Leu Gln Lys Pro Gly Gln Ser
        35                  40                  45 cca cag ctc ctg atc tat ttg ggt tct aat cgg gcc tcc ggg gtc cct      192
Pro Gln Leu Leu Ile Tyr Leu Gly Ser Asn Arg Ala Ser Gly Val Pro
    50                  55                  60 gac agg ttc agt ggc agt gga tca ggc aca gat ttt aca ctg aaa atc      240
Asp Arg Phe Ser Gly Ser Gly Ser Gly Thr Asp Phe Thr Leu Lys Ile
65                  70                  75                  80
```

```
agc aga gtg gag gct gag gat gtt ggg gtt tat tac tgc atg caa gct         288
Ser Arg Val Glu Ala Glu Asp Val Gly Val Tyr Tyr Cys Met Gln Ala
             85                  90                  95 cta caa act ccg                                                          300
Leu Gln Thr Pro
        100
```

<210> SEQ ID NO 32
<211> LENGTH: 100
<212> TYPE: PRT
<213> ORGANISM: Homo sapiens

<400> SEQUENCE: 32

```
Asp Ile Val Met Thr Gln Ser Pro Leu Ser Leu Pro Val Thr Pro Gly
 1               5                  10                  15

Glu Pro Ala Ser Ile Ser Cys Arg Ser Gln Ser Leu Leu His Arg
             20                  25                  30

Tyr Gly Tyr Asn Tyr Leu Asp Trp Tyr Leu Gln Lys Pro Gly Gln Ser
             35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro
        100
```

<210> SEQ ID NO 33
<211> LENGTH: 407
<212> TYPE: DNA
<213> ORGANISM: Homo sapiens
<220> FEATURE:
<221> NAME/KEY: CDS
<222> LOCATION: (3)...(407)
<220> FEATURE:
<221> NAME/KEY: sig_peptide
<222> LOCATION: (3)...(38)

<400> SEQUENCE: 33

```
tc ctc ctg ctg gtg gcg gct ccc aga tgg gtc ctg tcc cag ctg cag          47
   Leu Leu Leu Val Ala Ala Pro Arg Trp Val Leu Ser Gln Leu Gln
           -10                  -5                   1 ctg cag gag tcg ggc cca gga ctg gtg aag cct tcg gag acc ctg tcc         95
Leu Gln Glu Ser Gly Pro Gly Leu Val Lys Pro Ser Glu Thr Leu Ser
  5                  10                  15 ctc acc tgc act gtc tct ggt ggc tcc atc agc aga ggt agt cac tac        143
Leu Thr Cys Thr Val Ser Gly Gly Ser Ile Ser Arg Gly Ser His Tyr
 20                  25                  30                  35 tgg ggc tgg atc cgc cag ccc cca ggg aag ggg ctg gag tgg att ggg        191
Trp Gly Trp Ile Arg Gln Pro Pro Gly Lys Gly Leu Glu Trp Ile Gly
             40                  45                  50 agt atc tat tat agt ggg aac acc tac ttt aac ccg tcc ctc aag agt        239
Ser Ile Tyr Tyr Ser Gly Asn Thr Tyr Phe Asn Pro Ser Leu Lys Ser
         55                  60                  65 cga gtc acc ata tct gta gac acg tcc aag aac cag ttc tcc ctg aag        287
Arg Val Thr Ile Ser Val Asp Thr Ser Lys Asn Gln Phe Ser Leu Lys
     70                  75                  80 ctg agc tct gtg acc gcc gca gac acg gct gtg tat tac tgt gcg aga        335
Leu Ser Ser Val Thr Ala Ala Asp Thr Ala Val Tyr Tyr Cys Ala Arg
 85                  90                  95
```

-continued

```
ctc ggc cct gat gac tat acc ctt gac ggt atg gac gtc tgg ggc caa     383
Leu Gly Pro Asp Asp Tyr Thr Leu Asp Gly Met Asp Val Trp Gly Gln
100                 105                 110                 115 ggg acc acg gtc acc gtc tcc tca                                     407
Gly Thr Thr Val Thr Val Ser Ser
            120
```

<210> SEQ ID NO 34
<211> LENGTH: 135
<212> TYPE: PRT
<213> ORGANISM: Homo sapiens
<220> FEATURE:
<221> NAME/KEY: SIGNAL
<222> LOCATION: (1)...(12)

<400> SEQUENCE: 34

```
Leu Leu Leu Val Ala Ala Pro Arg Trp Val Leu Ser Gln Leu Gln Leu
            -10                 -5                   1

Gln Glu Ser Gly Pro Gly Leu Val Lys Pro Ser Glu Thr Leu Ser Leu
 5                  10                  15                  20

Thr Cys Thr Val Ser Gly Gly Ser Ile Ser Arg Gly Ser His Tyr Trp
                    25                  30                  35

Gly Trp Ile Arg Gln Pro Pro Gly Lys Gly Leu Glu Trp Ile Gly Ser
                40                  45                  50

Ile Tyr Tyr Ser Gly Asn Thr Tyr Phe Asn Pro Ser Leu Lys Ser Arg
        55                  60                  65

Val Thr Ile Ser Val Asp Thr Ser Lys Asn Gln Phe Ser Leu Lys Leu
    70                  75                  80

Ser Ser Val Thr Ala Ala Asp Thr Ala Val Tyr Tyr Cys Ala Arg Leu
85                  90                  95                  100

Gly Pro Asp Asp Tyr Thr Leu Asp Gly Met Asp Val Trp Gly Gln Gly
                105                 110                 115

Thr Thr Val Thr Val Ser Ser
            120
```

<210> SEQ ID NO 35
<211> LENGTH: 356
<212> TYPE: DNA
<213> ORGANISM: Homo sapiens
<220> FEATURE:
<221> NAME/KEY: CDS
<222> LOCATION: (1)...(356)
<220> FEATURE:
<221> NAME/KEY: sig_peptide
<222> LOCATION: (1)...(57)

<400> SEQUENCE: 35

```
atg aaa cac ctg tgg ttc ttc ctc ctc ctg gtg gca gct ccc aga tgg     48
Met Lys His Leu Trp Phe Phe Leu Leu Leu Val Ala Ala Pro Arg Trp
            -15                 -10                 -5 gtc ctg tcc cag gtg cag ctg cag gag tcg ggc cca gga ctg gtg aag     96
Val Leu Ser Gln Val Gln Leu Gln Glu Ser Gly Pro Gly Leu Val Lys
 1                  5                   10 cct tcg gag acc ctg tcc ctc acc tgc act gtc tct ggt ggc tcc gtc    144
Pro Ser Glu Thr Leu Ser Leu Thr Cys Thr Val Ser Gly Gly Ser Val
            15                  20                  25 agc agt ggt ggt tac tac tgg agc tgg atc cgg cag ccc cca ggg aag    192
Ser Ser Gly Gly Tyr Tyr Trp Ser Trp Ile Arg Gln Pro Pro Gly Lys
30                  35                  40                  45 gga ctg gag tgg att ggg tat atc tat tac agt ggg agc acc aac tac    240
Gly Leu Glu Trp Ile Gly Tyr Ile Tyr Tyr Ser Gly Ser Thr Asn Tyr
                50                  55                  60
```

```
aac ccc tcc ctc aag agt cga gtc acc ata tca gta gac acg tcc aag      288
Asn Pro Ser Leu Lys Ser Arg Val Thr Ile Ser Val Asp Thr Ser Lys
            65                  70                  75 aac cag ttc tcc ctg aag ctg agc tct gtg acc gct gcg gac acg gcc      336
Asn Gln Phe Ser Leu Lys Leu Ser Ser Val Thr Ala Ala Asp Thr Ala
        80                  85                  90 gtg tat tac tgt gcg aga ga                                           356
Val Tyr Tyr Cys Ala Arg
    95

<210> SEQ ID NO 36
<211> LENGTH: 118
<212> TYPE: PRT
<213> ORGANISM: Homo sapiens
<220> FEATURE:
<221> NAME/KEY: SIGNAL
<222> LOCATION: (1)...(19)

<400> SEQUENCE: 36

Met Lys His Leu Trp Phe Phe Leu Leu Leu Val Ala Ala Pro Arg Trp
                -15                 -10                 -5

Val Leu Ser Gln Val Gln Leu Gln Glu Ser Gly Pro Gly Leu Val Lys
                1               5                   10

Pro Ser Glu Thr Leu Ser Leu Thr Cys Thr Val Ser Gly Gly Ser Val
        15                  20                  25

Ser Ser Gly Gly Tyr Tyr Trp Ser Trp Ile Arg Gln Pro Pro Gly Lys
30                  35                  40                  45

Gly Leu Glu Trp Ile Gly Tyr Ile Tyr Tyr Ser Gly Ser Thr Asn Tyr
                50                  55                  60

Asn Pro Ser Leu Lys Ser Arg Val Thr Ile Ser Val Asp Thr Ser Lys
            65                  70                  75

Asn Gln Phe Ser Leu Lys Leu Ser Ser Val Thr Ala Ala Asp Thr Ala
        80                  85                  90

Val Tyr Tyr Cys Ala Arg
    95

<210> SEQ ID NO 37
<211> LENGTH: 356
<212> TYPE: DNA
<213> ORGANISM: Homo sapiens
<220> FEATURE:
<221> NAME/KEY: CDS
<222> LOCATION: (1)...(356)
<220> FEATURE:
<221> NAME/KEY: sig_peptide
<222> LOCATION: (1)...(57)

<400> SEQUENCE: 37 atg aag cac ctg tgg ttc ttc ctc ctg ctg gtg gcg gct ccc aga tgg      48
Met Lys His Leu Trp Phe Phe Leu Leu Leu Val Ala Ala Pro Arg Trp
                -15                 -10                 -5 gtc ctg tcc cag ctg cag ctg cag gag tcg ggc cca gga ctg gtg aag      96
Val Leu Ser Gln Leu Gln Leu Gln Glu Ser Gly Pro Gly Leu Val Lys
                1               5                   10 cct tcg gag acc ctg tcc ctc acc tgc act gtc tct ggt ggc tcc atc      144
Pro Ser Glu Thr Leu Ser Leu Thr Cys Thr Val Ser Gly Gly Ser Ile
        15                  20                  25 agc agt agt agt tac tac tgg ggc tgg atc cgc cag ccc cca ggg aag      192
Ser Ser Ser Ser Tyr Tyr Trp Gly Trp Ile Arg Gln Pro Pro Gly Lys
30                  35                  40                  45 ggg ctg gag tgg att ggg agt atc tat tat agt ggg agc acc tac tac      240
```

```
                                    -continued

Gly Leu Glu Trp Ile Gly Ser Ile Tyr Tyr Ser Gly Ser Thr Tyr Tyr
                50              55              60 aac ccg tcc ctc aag agt cga gtc acc ata tcc gta gac acg tcc aag     288
Asn Pro Ser Leu Lys Ser Arg Val Thr Ile Ser Val Asp Thr Ser Lys
                65              70              75 aac cag ttc tcc ctg aag ctg agc tct gtg acc gcc gca gac acg gct     336
Asn Gln Phe Ser Leu Lys Leu Ser Ser Val Thr Ala Ala Asp Thr Ala
        80              85              90 gtg tat tac tgt gcg aga ca                                          356
Val Tyr Tyr Cys Ala Arg
    95

<210> SEQ ID NO 38
<211> LENGTH: 118
<212> TYPE: PRT
<213> ORGANISM: Homo sapiens
<220> FEATURE:
<221> NAME/KEY: SIGNAL
<222> LOCATION: (1)...(19)

<400> SEQUENCE: 38

Met Lys His Leu Trp Phe Phe Leu Leu Leu Val Ala Ala Pro Arg Trp
                -15             -10             -5

Val Leu Ser Gln Leu Gln Leu Gln Glu Ser Gly Pro Gly Leu Val Lys
            1               5               10

Pro Ser Glu Thr Leu Ser Leu Thr Cys Thr Val Ser Gly Gly Ser Ile
    15              20              25

Ser Ser Ser Ser Tyr Tyr Trp Gly Trp Ile Arg Gln Pro Pro Gly Lys
30              35              40              45

Gly Leu Glu Trp Ile Gly Ser Ile Tyr Tyr Ser Gly Ser Thr Tyr Tyr
                50              55              60

Asn Pro Ser Leu Lys Ser Arg Val Thr Ile Ser Val Asp Thr Ser Lys
                65              70              75

Asn Gln Phe Ser Leu Lys Leu Ser Ser Val Thr Ala Ala Asp Thr Ala
        80              85              90

Val Tyr Tyr Cys Ala Arg
    95
```